United States Patent
Kim et al.

(10) Patent No.: US 9,908,089 B2
(45) Date of Patent: Mar. 6, 2018

(54) DEVICE FOR PRODUCING MICROBUBBLE WATER BY USING ULTRASONIC VIBRATOR, CELL CULTURE MEDIUM CONTAINING MICROBUBBLE WATER, CELL CULTURING METHOD USING SAME, HIGH EFFICIENCY MIXED FUEL USING MICROBUBBLES, AND METHOD FOR MANUFACTURING SAME

(71) Applicant: CHUNG-ANG UNIVERSITY INDUSTRY-ACADEMY COOPERATION FOUNDATION, Seoul (KR)

(72) Inventors: Jong Min Kim, Seoul (KR); Seung Hoon Oh, Seoul (KR)

(73) Assignee: CHUNG-ANG UNIVERSITY INDUSTRY-ACADEMY COOPERATION FOUNDATION, Seoul (KR)

( * ) Notice: Subject to any disclaimer, the term of this patent is extended or adjusted under 35 U.S.C. 154(b) by 94 days.

(21) Appl. No.: 14/649,401

(22) PCT Filed: Nov. 18, 2013

(86) PCT No.: PCT/KR2013/010476
§ 371 (c)(1),
(2) Date: Aug. 13, 2015

(87) PCT Pub. No.: WO2014/088242
PCT Pub. Date: Jun. 12, 2014

(65) Prior Publication Data
US 2015/0343399 A1    Dec. 3, 2015

(30) Foreign Application Priority Data

Dec. 4, 2012 (KR) .................. 10-2012-0139663
Apr. 8, 2013 (KR) .................. 10-2013-0038064
(Continued)

(51) Int. Cl.
*C10L 1/00* (2006.01)
*B01F 3/04* (2006.01)
(Continued)

(52) U.S. Cl.
CPC ...... *B01F 3/04255* (2013.01); *B01F 3/04262* (2013.01); *B01F 3/04978* (2013.01);
(Continued)

(58) Field of Classification Search
CPC .............. C10L 1/12; C10L 2290/34; C10L 2200/0423; C10L 1/1208; C10L 1/125; C10L 1/328; C10L 2250/084
See application file for complete search history.

(56) References Cited

U.S. PATENT DOCUMENTS

| 6,382,601 B1 | 5/2002 | Ohnari | |
|---|---|---|---|
| 7,775,196 B2 * | 8/2010 | Suzuki | .................. F02M 27/08 123/1 A |
| 7,789,047 B2 * | 9/2010 | Kuroki | ...................... C01B 3/02 123/1 A |

FOREIGN PATENT DOCUMENTS

| CN | 2477967 Y | 2/2002 |
|---|---|---|
| CN | 101180462 B | 3/2011 |

(Continued)

OTHER PUBLICATIONS

Asada "Antitumor effects of nano-bubble hydrogen-dissolved water are enhanced by coexistent platinum colloid and the combined hyperthermia with apoptosis-like cell death" Oncology Reports, 24, 1463-1470.*

(Continued)

*Primary Examiner* — Cephia D Toomer
(74) *Attorney, Agent, or Firm* — Brundidge & Stanger, P.C.

(57) ABSTRACT

The present disclosure relates to a device for producing microbubble water by using a ultrasonic vibrator having a maximized amount of dissolved bubbles, a microbubble discharge unit, cell culture medium containing microbubble water and cell culturing method using the same, a high-
(Continued)

efficiency mixed fuel using microbubble and apparatus for manufacturing the same.

4 Claims, 33 Drawing Sheets

(30) Foreign Application Priority Data

| Apr. 26, 2013 | (KR) | 10-2013-0047000 |
|---|---|---|
| Nov. 18, 2013 | (KR) | 10-2013-0140180 |
| Nov. 18, 2013 | (KR) | 10-2013-0140181 |

(51) Int. Cl.

| *B01F 15/02* | (2006.01) |
|---|---|
| *C10L 1/12* | (2006.01) |
| *B01F 15/06* | (2006.01) |
| *C12N 5/00* | (2006.01) |
| *B01F 11/02* | (2006.01) |
| *C12M 1/00* | (2006.01) |
| *C10L 1/32* | (2006.01) |

(52) U.S. Cl.
CPC ...... *B01F 11/0258* (2013.01); *B01F 15/0261* (2013.01); *B01F 15/06* (2013.01); *C10L 1/12* (2013.01); *C10L 1/125* (2013.01); *C10L 1/328* (2013.01); *C12M 29/06* (2013.01); *C12N 5/0018* (2013.01); *B01F 2003/04319* (2013.01); *B01F 2003/04361* (2013.01); *B01F 2215/0073* (2013.01); *B01F 2215/0086* (2013.01); *C10L 1/1208* (2013.01); *C10L 2200/0423* (2013.01); *C10L 2250/084* (2013.01); *C10L 2290/34* (2013.01); *C12N 2500/02* (2013.01); *C12N 2527/00* (2013.01)

(56) References Cited

FOREIGN PATENT DOCUMENTS

| CN | 202073656 U | 12/2011 |
|---|---|---|
| JP | 2008-019359 A | 1/2008 |
| JP | 2008-074936 A | 4/2008 |
| JP | 2010075180 A | 4/2010 |
| KR | 10-0394430 B1 | 8/2003 |
| KR | 10-2011-0002295 A | 1/2011 |
| KR | 10-1071461 B1 | 10/2011 |
| KR | 10-2012-0084134 A | 7/2012 |

OTHER PUBLICATIONS

International Search Report of PCT/KR2013/010476 dated Apr. 28, 2014.

Kosaku Kurata et al., "Development of a Compact Microbubble Generator and Its Usefulness for Three-Dimensional Osteoblastic Cell Culture", Journal of Biomechanical Science and Engineering, 2007, vol. 2, No. 4, pp. 166-177.

H. Nagata et al., "The Culture Medium Including Oxygen Nano Bubbles Is Presented to Improve the Viability of Islet Cells From Non-Heart Beating Donor Pancreas", Poster Board No. P2-142, Transplantation, Jul. 27, 2008., vol. 86, No. 2S, p. 453.

* cited by examiner

PARTICLE SIZE/CONCENTRATION

PARTICLE SIZE/RELATIVE INTENSITY 3D PLOT

FIG. 4B

| BIN CENTRE (NM) | CONCENTRATION (E.g. PARTICLE/mL) | PERCENTILE UNDERSIZE |
|---|---|---|
| 10 | 0.000 | 0.00% |
| 30 | 4.875 | 0.86% |
| 50 | 22.764 | 5.42% |
| 70 | 54.205 | 23.54% |
| 90 | 76.467 | 60.57% |
| 110 | 30.692 | 84.03% |
| 130 | 13.164 | 93.33% |
| 150 | 4.781 | 96.45% |
| 170 | 4.427 | 98.83% |
| 190 | 0.891 | 99.92% |
| 210 | 0.024 | 100.00% |
| 230 | 0.000 | 100.00% |
| 250 | 0.000 | 100.00% |
| 270 | 0.000 | 100.00% |
| 290 | 0.000 | 100.00% |
| 310 | 0.000 | 100.00% |
| 330 | 0.000 | 100.00% |
| 350 | 0.000 | 100.00% |
| 370 | 0.000 | 100.00% |
| 390 | 0.000 | 100.00% |
| 410 | 0.000 | 100.00% |
| 430 | 0.000 | 100.00% |
| 450 | 0.000 | 100.00% |
| 470 | 0.000 | 100.00% |
| 490 | 0.000 | 100.00% |
| 510 | 0.000 | 100.00% |

| BIN CENTRE (NM) | CONCENTRATION (E.g. PARTICLE/mL) | PERCENTILE UNDERSIZE |
|---|---|---|
| 530 | 0.000 | 100.00% |
| 550 | 0.000 | 100.00% |
| 570 | 0.000 | 100.00% |
| 590 | 0.000 | 100.00% |
| 610 | 0.000 | 100.00% |
| 630 | 0.000 | 100.00% |
| 650 | 0.000 | 100.00% |
| 670 | 0.000 | 100.00% |
| 690 | 0.000 | 100.00% |
| 710 | 0.000 | 100.00% |
| 730 | 0.000 | 100.00% |
| 750 | 0.000 | 100.00% |
| 770 | 0.000 | 100.00% |
| 790 | 0.000 | 100.00% |
| 810 | 0.000 | 100.00% |
| 830 | 0.000 | 100.00% |
| 850 | 0.000 | 100.00% |
| 870 | 0.000 | 100.00% |
| 890 | 0.000 | 100.00% |
| 910 | 0.000 | 100.00% |
| 930 | 0.000 | 100.00% |
| 950 | 0.000 | 100.00% |
| 970 | 0.000 | 100.00% |
| 990 | 0.000 | 100.00% |
| 1000-2000 | 0.000 | 100.00% |

RESULTS
MEAN : 87 nm
MODE : 85 nm
SD : 27 nm
D10 : 54 nm
D50 : 84 nm
D90 : 121 nm
USER LINES : 0, 0 nm
CONCENTRATION: 2.12 × 10$^8$ PARTICLE/mL

MEASUREMENT CONDITIONS
TEMPERATURE : 28.50°C
VISCOSITY : 0.82 cP
FRAMES PER SECOND : 24.73
MEASUREMENT TIME: 30 SEC
DRIFT VELOCITY : 1122 nm/s

ANALYSIS CONDITION
BRIGHTNESS : -0
GAIN : 1.00
BLUR : 5×5
DETECTION THRESHOLD: AUTO
MAXIMUM BLOB SIZE (PIXEL AREA) : 3000
MINIMUM TRACK LENGTH: AUTOMATIC
MINIMUM EXPECTATED SIZE: 50 nm

PARTICLE SIZE/CONCENTRATION

PARTICLE SIZE/RELATIVE INTENSITY 3D PLOT

FIG. 5B

| BIN CENTRE (NM) | CONCENTRATION (E.g. PARTICLE/mL) | PERCENTILE UNDERSIZE |
|---|---|---|
| 10 | 0.169 | 0.00% |
| 30 | 12.921 | 1.30% |
| 50 | 53.746 | 15.47% |
| 70 | 60.781 | 38.94% |
| 90 | 41.520 | 56.63% |
| 110 | 48.327 | 75.77% |
| 130 | 23.047 | 89.28% |
| 150 | 8.227 | 93.55% |
| 170 | 7.410 | 96.88% |
| 190 | 2.617 | 98.51% |
| 210 | 1.952 | 99.30% |
| 230 | 0.891 | 99.86% |
| 250 | 0.116 | 99.99% |
| 270 | 0.003 | 100.00% |
| 290 | 0.000 | 100.00% |
| 310 | 0.000 | 100.00% |
| 330 | 0.000 | 100.00% |
| 350 | 0.000 | 100.00% |
| 370 | 0.000 | 100.00% |
| 390 | 0.000 | 100.00% |
| 410 | 0.000 | 100.00% |
| 430 | 0.000 | 100.00% |
| 450 | 0.000 | 100.00% |
| 470 | 0.000 | 100.00% |
| 490 | 0.000 | 100.00% |
| 510 | 0.000 | 100.00% |

| BIN CENTRE (NM) | CONCENTRATION (E.g. PARTICLE/mL) | PERCENTILE UNDERSIZE |
|---|---|---|
| 530 | 0.000 | 100.00% |
| 550 | 0.000 | 100.00% |
| 570 | 0.000 | 100.00% |
| 590 | 0.000 | 100.00% |
| 610 | 0.000 | 100.00% |
| 630 | 0.000 | 100.00% |
| 650 | 0.000 | 100.00% |
| 670 | 0.000 | 100.00% |
| 690 | 0.000 | 100.00% |
| 710 | 0.000 | 100.00% |
| 730 | 0.000 | 100.00% |
| 750 | 0.000 | 100.00% |
| 770 | 0.000 | 100.00% |
| 790 | 0.000 | 100.00% |
| 810 | 0.000 | 100.00% |
| 830 | 0.000 | 100.00% |
| 850 | 0.000 | 100.00% |
| 870 | 0.000 | 100.00% |
| 890 | 0.000 | 100.00% |
| 910 | 0.000 | 100.00% |
| 930 | 0.000 | 100.00% |
| 950 | 0.000 | 100.00% |
| 970 | 0.000 | 100.00% |
| 990 | 0.000 | 100.00% |
| 1000-2000 | 0.000 | 100.00% |

RESULTS
MEAN : 87 nm
MODE : 62 nm
SD : 36 nm
D10 : 44 nm
D50 : 80 nm
D90 : 131 nm
USER LINES : 0, 0 nm
CONCENTRATION: $2.62 \times 10^8$ PARTICLE/mL MEASUREMENT CONDITIONS
TEMPERATURE : 29.20°C
VISCOSITY : 0.81 cP
FRAMES PER SECOND : 22.95
MEASUREMENT TIME : 30 SEC
DRIFT VELOCITY : 450 nm/s ANALYSIS CONDITION
BRIGHTNESS : -0
GAIN : 1.00
BLUR : 5x5
DETECTION THRESHOLD: AUTO
MAXIMUM BLOB SIZE (PIXEL AREA): 3000
MINIMUM TRACK LENGTH: AUTOMATIC
MINIMUM EXPECTATED SIZE: 50 nm

| CLASSIFICATION | TIME | |
| --- | --- | --- |
| | 0 | 72 HOURS |
| CONTROL |  |  |
| H₂ BUBBLE WATER (10%) |  |  |
| O₂ BUBBLE WATER (20%) |  |  |

| CLASSIFICATION | TIME | |
| --- | --- | --- |
| | 0 | 72 HOURS |
| CONTROL |  |  |
| H₂ BUBBLE WATER (5%) |  |  |
| O₂ BUBBLE WATER (20%) |  |  |

| CLASSIFICATION | TIME | |
|---|---|---|
| | 0 | 72 HOURS |
| CONTROL |  |  |
| $H_2$ BUBBLE WATER (10%) |  |  |
| $O_2$ BUBBLE WATER (20%) |  |  |

| CLASSIFICATION | TIME | |
| --- | --- | --- |
| | 0 | 72 HOURS |
| CONTROL |  |  |
| H₂ BUBBLE WATER (10%) |  |  |
| O₂ BUBBLE WATER (5%) |  |  |

| CLASSIFICATION | TIME | |
| --- | --- | --- |
| | 0 | 72 HOURS |
| CONTROL |  |  |
| H₂ BUBBLE WATER (10%) |  |  |
| O₂ BUBBLE WATER (5%) |  |  |

DEVICE FOR PRODUCING MICROBUBBLE WATER BY USING ULTRASONIC VIBRATOR, CELL CULTURE MEDIUM CONTAINING MICROBUBBLE WATER, CELL CULTURING METHOD USING SAME, HIGH EFFICIENCY MIXED FUEL USING MICROBUBBLES, AND METHOD FOR MANUFACTURING SAME

TECHNICAL FIELD

The invention relates to a device for producing microbubble water using a ultrasonic vibrator capable of mass-producing bubble water having the maximized amount of dissolved gases, a microbubble discharge unit, a cell culture medium containing the microbubble water and satisfying both of economical efficiency and safety, a cell culturing method using the cell culture medium, a high-efficiency mixed fuel using microbubbles, and an apparatus for manufacturing the same.

BACKGROUND

In recent years, water having a higher dissolved gas content than general water has been produced. By way of example, oxygen (gas) water having a high dissolved oxygen content has been mainly used for purifying wastewater from a stock farm or supplying oxygen (gas) to fish in a fish farm. If an animal or a human drinks the oxygen water, the oxygen water is quickly absorbed into the body and activates metabolism and makes the body resistant to various insect pests and diseases. Therefore, such oxygen water has been often used not only in stock farms but also in water purifiers of family homes or companies. Further, as for plants, oxygen water improves the soil environment and directly supplies oxygen to leaves or roots, and thus, helps the plants grow stronger and makes the plants resistant to insect pests and diseases, resulting in an increase in production. For the above-described reasons, various methods and apparatuses have been provided in order to produce oxygen (gas, bubble) water. Conventionally, the methods and apparatuses for producing gas water using a motor to mix water at a high speed while increasing the dissolved gas content. However, according to such a method, it is difficult to obtain a desirable dissolved gas content in a short time and also difficult to generate microbubbles. Further, there has been provided a method for producing oxygen (gas) water by electrolysis or freezing. In this case, the system is very expensive, and mixed oxygen (gas) is present in the form of bubbles in water. Therefore, the dissolved oxygen content rapidly decreases depending on time and a size of a bubble cannot be controlled. Furthermore, according to a method for producing oxygen (gas) water by supplying micro-air-bubbles, it is possible to produce high-concentration oxygen (gas) water, but it is necessary to continuously generate and supply nanobubbles under a high pressure condition in order to supply nanobubbles. Also, in this case, a considerable amount of oxygen (gas) is present in the form of bubbles in water and the dissolved oxygen content rapidly decreases depending on time.

A serum is a composite product in which various materials are mixed, and is used as an additive to a basic cell culture medium in a cell incubation room, and the serum for cell culture includes growth factors, hormones, components that stimulates cells, etc. and is variously used according to the kind of a cell. In general, however, fetal bovine serum (FBS) is the most widely used serum. The FBS is a serum which is isolated from the blood of a cow during pregnancy, and in particular, is used as a raw material in developing vaccines, protein medical supplies, and therapeutic antibodies of which technology development is being accelerated around the world for recent several years, as well as in culturing animal cells, which is a basic step in biotechnology related experiments. However, recently, the supply of the FBS has been restricted following the outbreak of bovine spongiform encephalopathy, and the price thereof has risen sharply. Further, a target product can be infected with bovine spongiform encephalopathy, and thus, the safety thereof cannot be sufficiently guaranteed. The Korean FBS market is worth about 20 billion won, and the world market for FBS is worth about 2 trillion won. American FBS accounts for about 85% and Australian and New Zealand FBS accounts for about 15%. Korean FBS has not been produced or has not been commercialized on sale. Accordingly, once the FBS import is banned, there are few available countermeasures. Therefore, the need for development of other serums as alternatives to the FBS or components of a culture medium has been greatly increased. Korean Patent No. 10-0394430 describes a method for culturing a human cell comprising a human serum in a medium used for culturing a human cell. However, according to the above-described patent, the medium can be infected with human viruses such as AIDS and the supply thereof is restricted. Further, it is not very effective in culturing other animal cells, and even when culturing a human cell, it is much less effective than a medium using FBS. Therefore, it cannot be a complete alternative to FBS. It may help a slight reduction in the use of FBS, but its economical efficiency is very low. Therefore, development of other serums as alternatives to the FBS or other components of a culture medium which can reduce the use of FBS and also promote cell growth has been demanded. In this regard, the use of high-priced FBS has been reduced by using nanobubble water as a component for cell culture.

Meanwhile, fossil fuels have been mainly used as energy sources on earth, and such fossil fuels are limited in their respective reserves. Therefore, they need to be efficiently used. Middle Eastern crude oil prices have been continuously increased every year. According to the IEA (International Energy Agency) 2010 data, Middle Eastern crude oil prices are expected to reach about $243.8/BL in 2035. The average oil consumption per day in 2010 was about 80.740 million BL, and an increase in oil consumption and an increase in oil prices have emerged as a major issue. Attention to development of a next-generation fuel has been demanded. Although studies for developing fuel cells or hydrogen fuels as alternative energy sources have been carried out, development of a high-efficiency energy source is needed in order to suppress oil consumption. Korean Patent No. 10-1071461 relates to a microbubble generation apparatus, and describes a microbubble generation apparatus that converts a mixed oil including water and fuel into an emulsion state by stirring. However, according to the above-described method, the mixed oil converted into an emulsion state may be unstable in a certain period of time, and the water and the fuel may separate. In order to solve this problem, development of a high-efficiency fuel which is stable and in which separation does not occur is demanded.

DETAILED DESCRIPTION

Problems Solved

In view of the foregoing problems, one purpose of the present disclosure is to provide a device for producing microbubble water using a ultrasonic vibrator. In the device, a porous pipe body received ultrasonic vibrations propagated from the ultrasonic vibrator and thus, the porous pipe body is vibrated so that discharge a gas in the form of microbubbles is vibrated. When microbubbles are generated from the porous pipe body, aggregation of the microbubbles and detachment of the microbubbles from the porous pipe body easily occur. Further, it is not necessary to inject a high-pressure gas in order to generate microbubbles. Therefore, it is possible to mass-produce microbubbles by a relatively simple system, resulting in a significant reduction in production cost. The porous pipe body discharges relatively uniform microbubbles, and thus, it is possible to mass-produce bubble water of high quality in a relatively short time.

Another purpose of the present disclosure is also to provide a microbubble discharge unit which facilitates detachment of microbubbles generated by the porous pipe body when ultrasonic vibrations are applied from the ultrasonic vibrator to the porous pipe body.

Another purpose of the present disclosure is to provide a cell culture medium containing the microbubble water both satisfying safety and economical efficiency by reducing the use of high-priced FBS, and a cell culturing method using the same.

Another purpose of the present disclosure is to provide a high-efficiency mixed fuel using microbubbles and an apparatus for manufacturing the same.

However, problems to be solved by the example embodiments of the present disclosure are not limited to the above-described problems. Although not described herein, other problems to be solved by the present disclosure can be clearly understood by those skilled in the art from the following descriptions.

Means for Solving Problems

In a first aspect of the present disclosure, there is provided a device for producing microbubble water using a ultrasonic vibrator, comprising: a liquid tank to accommodates a liquid; a liquid circulation line unit to forcibly circulate the liquid accommodated in the liquid tank; a gas supply line unit to supply a gas into the liquid tank; and, a plurality of microbubble discharge units which are provided in the liquid tank and connected to the gas supply line unit, being vibrated by a ultrasonic wave to detach microbubbles so that the microbubbles are not to aggregated with another when a gas supplied from the gas supply line unit is discharged in the form of microbubbles.

In a second aspect of the present disclosure, there is provided a microbubble discharge unit using a ultrasonic vibrator comprising: a body unit provided to be connected to one side of a porous pipe body and configured to generate vibrations by a ultrasonic vibrator provided therein; and, a vibration transfer unit attached to the one side of the porous pipe body and configured to transfer ultrasonic vibrations generated by the body unit to the porous pipe body, wherein the ultrasonic vibrations are applied to the porous pipe body via the vibration transfer unit so as to detach microbubbles generated by the porous pipe body.

In a third aspect of the present disclosure, there is provided a cell culture medium comprising: a serum and an antibiotic, wherein the cell culture medium contains microbubble water, and 1 mL of the microbubble water contains from $10^3$ to $10^{18}$ of microbubbles having an average diameter of from 1 nm to 1,000 μm.

In a fourth aspect of the present disclosure, there is provided a cell culturing method comprising: culturing a cell in a culture medium in a confluent manner; and, replacing the cell culture medium with a culture medium including microbubble water, wherein 1 mL of the microbubble water contains from $10^3$ to $10^{18}$ of microbubbles having an average diameter of from 1 nm to 1,000 μm.

In a fifth aspect of the present disclosure, there is provided a high-efficiency mixed fuel comprising: a fuel; and, microbubbles formed in the fuel.

In a sixth aspect of the present disclosure, there is provided an apparatus for manufacturing a high-efficiency mixed fuel, comprising: a liquid tank into which a liquid is injected; a gas supply line unit configured to supply a gas into the liquid tank; and, a porous pipe body provided in the liquid tank.

Effect

In a device for producing microbubble water using a ultrasonic vibrator according to the present disclosure, firstly, through a porous pipe body configured to discharge a low-pressure gas supplied from the outside in the form of microbubbles is vibrated when receiving ultrasonic vibrations propagated from the ultrasonic vibrator, and thus, the microbubbles are detached from the porous pipe body before the microbubbles attach to a surface of the porous pipe body or aggregated with another, so that it is possible to produce bubble water having the maximized amount of dissolved bubbles in a liquid accommodated in a liquid tank. Further, since it is not necessary to inject a high-pressure gas in order to generate microbubbles, it is possible to mass-produce of high-quality bubble water by a relatively simple system, resulting in a significant reduction in production cost for producing high-quality bubble water. Secondly, since a residual gas which is not mixed with a liquid is allowed to remain in the liquid tank and the atmosphere within the liquid tank is maintained in a gas-saturated state, it is possible to maximize the dissolved gas content of bubble water and also possible to produce bubble water maintaining a sufficient dissolved gas content even after time passes. Thirdly, since the generated microbubbles are very small and relatively uniform in size, the microbubbles can be efficiently dissolved in the liquid (water) and a predetermined dissolved gas ratio of the bubble water can be achieved in a relatively short time. Fourthly, it is possible to generate microbubbles small and uniform in size within a high-viscosity material. Fifthly, it is possible to produce high-efficiency clean energy containing microbubbles.

A microbubble discharge unit according to the present disclosure can facilitate detachment of microbubbles generated by the porous pipe body when ultrasonic vibrations are applied from the ultrasonic vibrator to the porous pipe body.

A cell culture medium according to the present disclosure contains microbubble water, and thus, can reduce the use of high-priced FBS while having a cell growth-promoting effect equivalent to or higher than that of a FBS-containing culture medium. Further, since the microbubble water itself is safe, it is possible to economically and safely culture a cell.

In a high-efficiency mixed fuel and an apparatus for manufacturing the high-efficiency mixed fuel according to the present disclosure, microbubbles are generated in a conventional fuel, so that fuel combustion and fuel efficiency can be improved and further energy consumption and harmful emissions can be reduced. To be specific, the microbubbles contained in the fuel reduces a frictional force generated between an inner surface of a pipe passage and the fuel when the fuel passes through the pipe passage, and thus, can improve the efficiency of the fuel and also reduce a amount of harmful emissions generated after combustion of the fuel to a significant level.

BRIEF DESCRIPTION OF THE DRAWINGS

FIG. 4A and FIG. 4B are test charts showing the measured sizes and concentrations of bubbles in hydrogen microbubble water in accordance with an example of the present disclosure.

FIG. 5A and FIG. 5B are test charts showing the measured sizes and concentrations of bubbles in oxygen microbubble water in accordance with an example of the present disclosure.

BEST MODE

Figure 1:
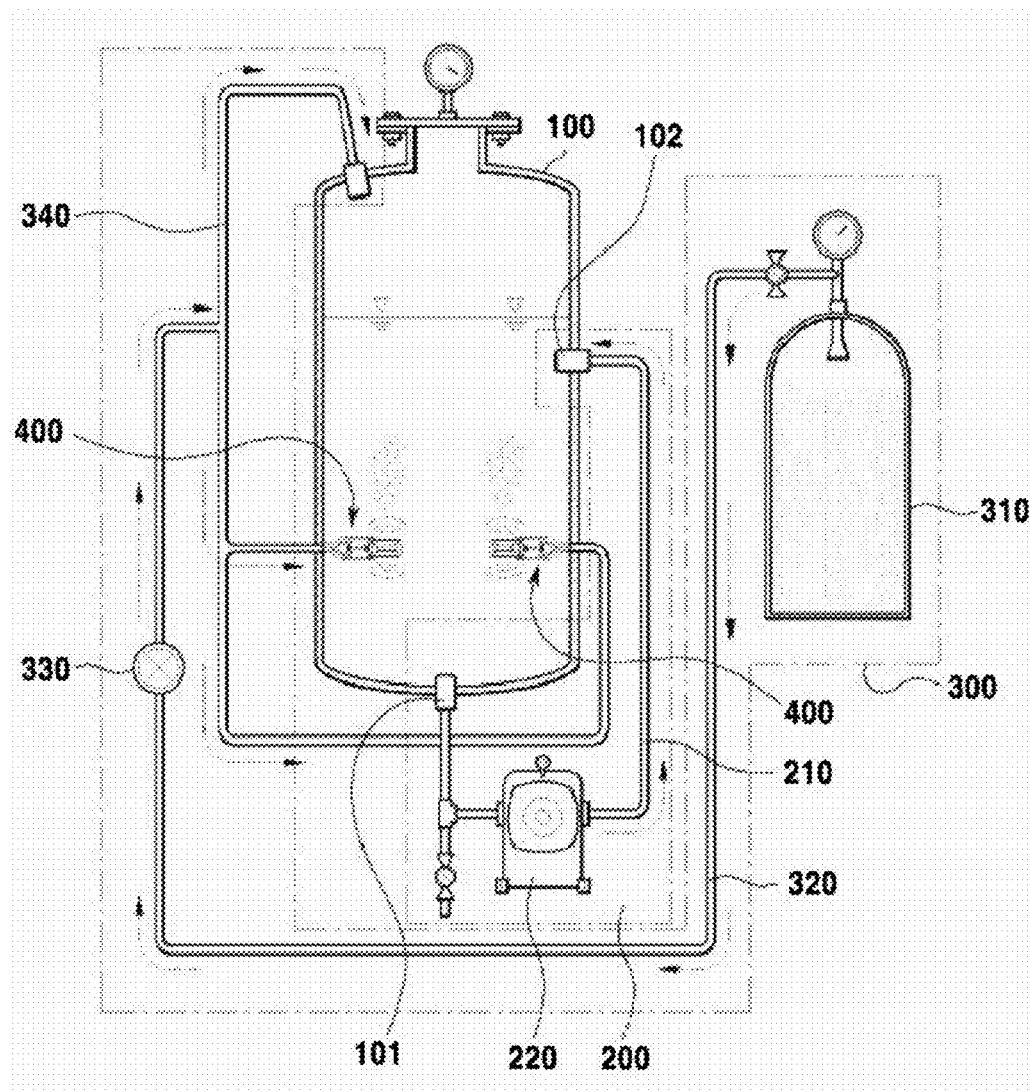
FIG. 1 shows a device for producing microbubble water in accordance with an example of the present disclosure.

Hereinafter, examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for the simplicity of explanation, and like reference numerals denote like parts through the whole document of the present disclosure.

Through the whole document of the present disclosure, the term "connected to" or "coupled to" that is used to designate a connection or coupling of one element to another element includes both a case that an element is "directly connected or coupled to" another element and a case that an element is "electronically connected or coupled to" another element via still another element.

Through the whole document of the present disclosure, the term "on" that is used to designate a position of one element with respect to another element includes both a case that the one element is adjacent to the another element and a case that any other element exists between these two elements.

Through the whole document of the present disclosure, the term "comprises or includes" and/or "comprising or including" used in the document means that one or more other components, steps, operation and/or existence or addition of elements are not excluded in addition to the described components, steps, operation and/or elements unless context dictates otherwise. The term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document of the present disclosure, the term "combinations of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document of the present disclosure, a phrase in the form "A and/or B" means "A or B, or A and B".

Through the whole document of the present disclosure, the term "microbubbles" include micrometer-sized microbubbles and/or nanometer-sized nanobubbles. The microbubbles may have an average diameter of from about 1 nm to about 1,000 μm, but may not be limited thereto. By way of example, the microbubbles may have an average diameter of from about 1 μm to about 1,000 μm, and the nanobubbles may have an average diameter of from about 1 nm to about 1,000 nm.

Through the whole document of the present disclosure, a gas used for generating microbubbles may include a gas selected from the group consisting of hydrogen, oxygen, carbon dioxide, carbon monoxide, nitrogen, xenon, argon, neon, air, ozone, krypton, helium, a nitrogen-containing compound gas, a carbon-containing compound gas, and combinations thereof, but may not be limited thereto. The nitrogen-containing compound gas is not particularly limited as long as it is a compound containing nitrogen in the form of a gas, and may include, for example, but not limited to, ammonia, nitrogen oxides, and the like. The carbon-containing compound gas is not particularly limited as long as it is a compound containing carbon in the form of a gas, and may include, for example, but not limited to, hydrocarbon compound gases (methane, ethane, propane, butane, etc.) having 1 to 4 carbon atoms.

Hereinafter, the present disclosure will be explained in more detail.

In a first aspect of the present disclosure, there is provided a device for producing microbubble water using a ultrasonic vibrator, comprising: a liquid tank to accommodates a liquid; a liquid circulation line unit to forcibly circulate the liquid accommodated in the liquid tank; a gas supply line unit to supply a gas into the liquid tank; and a plurality of microbubble discharge unit which are provided in the liquid tank and connected to the gas supply line unit, and being vibrated by a ultrasonic waves to detach microbubbles so that the microbubbles are not to aggregated with another when a gas supplied from the gas supply line unit is discharged in the form of microbubbles.

In accordance with an embodiment of the present disclosure, the liquid may include a member selected from the group consisting of water, high-viscosity materials, and combinations thereof, but may not be limited thereto. By way of example, the high-viscosity material may include a member selected from the group consisting of polymers, fuels, and combinations thereof, but may not be limited thereto. By way of example, the high-viscosity material may include a member selected from the group consisting of polymers, fossil fuels, bio fuels, and combinations thereof, and may include, for example, a member selected from the group consisting of lubricating oil, gasoline, diesel, bunker oil, bio ethanol, bio methanol, bio diesel, and combinations thereof, but may not be limited thereto.

In accordance with an embodiment of the present disclosure, in the device for producing microbubble water using a ultrasonic vibrator, the liquid tank 100 has a predetermined space therein to accommodate a predetermined amount of liquid as illustrated in FIG. 1, and may include a see-through window (not illustrated), through which the inside can be seen, at an upper part thereof, but may not be limited thereto. A check valve (not illustrated) configured to check an internal pressure of the liquid tank 100 and regulates the internal pressure of the liquid tank 100 may be further provided at an upper surface of the liquid tank 100, but may not be limited thereto. Further, a discharge port 101 for discharging the liquid accommodated in the liquid tank 100 and an inlet port 102 for introducing the liquid into the liquid tank 100 may be formed, but may not be limited thereto. By way of example, the discharge port 101 may be formed at a position lower than a water level of the liquid accommodated in the liquid tank 100 and may be formed at a lower part of the liquid tank 100, but may not be limited thereto. By way of example, the inlet port 102 may be formed at an upper part or a lower part of the liquid tank 100, but may not be limited thereto. In addition, a gas injection unit configured to introduce a gas may be further provided at an upper part of the liquid tank 100, but may not be limited thereto. The gas injection unit may include injecting a gas into the liquid tank 100 and to maintain the atmosphere in a gas-saturated state in the liquid tank 100 and generate a pressure in the liquid tank 100, but may not be limited thereto.

In accordance with an embodiment of the present disclosure, the liquid circulation line unit 200 is configured to circulate the liquid accommodated in the liquid tank 100, and may include a circulation pipe 210 and a circulation motor 220, but may not be limited thereto. The circulation pipe 210 is configured to connect the discharge port 101 and the inlet port 102 of the liquid tank 100, and the liquid in the liquid tank 100 is discharged through the discharge port 101 and then reintroduced into the liquid tank 100 through the inlet port 102 and circulated therein, but may not be limited thereto. Further, the circulation pipe 210 includes the circulation motor 220, and the circulation motor 220 is selectively operated in response to a control signal applied from the outside and forcibly circulate the liquid in the liquid tank 100 to be discharged through the discharge port 101, circulated along the circulation pipe 210, and reintroduced into the liquid tank 100 through the inlet port 102, but may not be limited thereto. Therefore, in the liquid circulation line unit 200, the circulation pipe 210 is configured to connect the discharge port 101 and the inlet port 102 of the liquid tank 100 and the circulation motor 220 included in the circulation pipe 210 is configured to be operated in response to a control signal applied from the outside such that the liquid in the liquid tank 100 is discharged through the discharge port 101, circulated along the circulation pipe 210, and reintroduced into the liquid tank 100 through the inlet port 102, but may not be limited thereto.

In accordance with an embodiment of the present disclosure, the gas supply line unit 300 is configured to supply a gas into the liquid tank 100, and may include a gas bomb 310, a supply pipe 320, a pressure control valve 330, and a distribution pipe 340, but may not be limited thereto. The gas may include a gas selected from the group consisting of hydrogen, oxygen, carbon dioxide, carbon monoxide, nitrogen, xenon, argon, neon, air, ozone, krypton, helium, a nitrogen-containing compound gas, a carbon-containing compound gas, and combinations thereof, but may not be limited thereto. The gas bomb 310 of the gas supply line unit 300 is filled with a gas to be dissolved in the liquid tank 100 and may be supplied by an internal pressure of the bomb generated in a gas-filled state, but may not be limited thereto. The gas bomb 310 may also include a pressure gauge for checking a pressure and an opening/closing valve, but may not be limited thereto. The opening/closing valve (not illustrated) of the gas bomb 310 is connected to the supply pipe 320, so that the gas supplied from the gas bomb 310 is flowed, but may not be limited thereto. The supply pipe 320 is connected to the pressure control valve 330, and a pressure of the gas flowed and supplied through the supply pipe 320 by the pressure control valve 330 selectively decrease or increase in the pressure, so that the gas can be controlled to supply at a predetermined uniform pressure, but may not be limited thereto. Further, the distribution pipe 340 may be configured to distribute and supply the gas decreased or increased in the pressure by the pressure control valve 330, but may not be limited thereto. The gas may be injected through the distribution pipe 340 into the liquid tank 100 by the gas injection unit provided at the upper part of the liquid tank 100, or the gas may be supplied through the distribution pipe 340 into the microbubble discharge unit 400 provided within the liquid tank 100, but may not be limited thereto. Therefore, in the gas supply line unit 300, the gas filled within the gas bomb 310 is supplied by an internal pressure of the bomb, flowed through the supply pipe 320, and distributed by the distribution pipe 340 as being maintained at a predetermined uniform pressure by the pressure control valve 330, and the gas in the gas bomb 310 may be supplied to the gas injection unit and the microbubble discharge unit 400, but may not be limited thereto.

Figure 2:
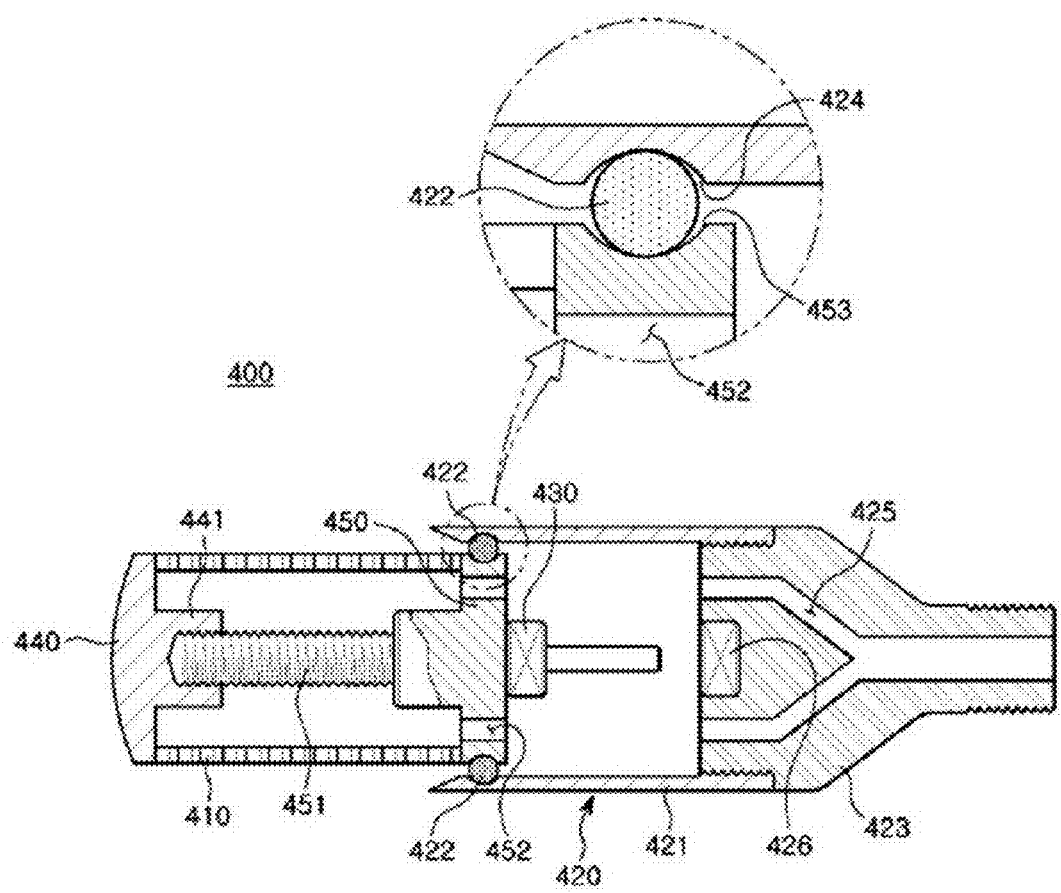
FIG. 2 is a cross-sectional view showing a microbubble discharge unit in accordance with an example of the present disclosure.
Figure 3:
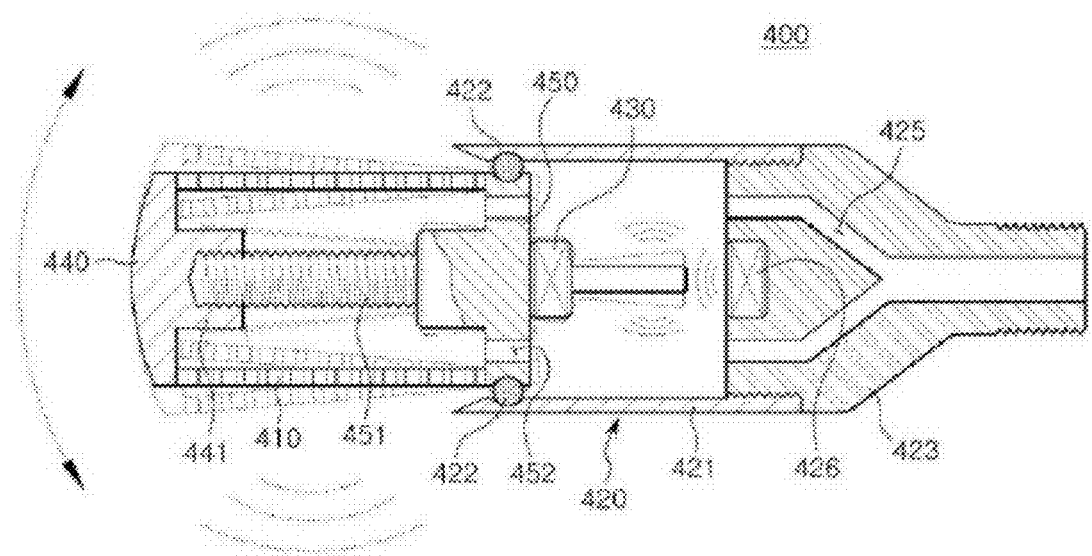
FIG. 3 is an exemplary diagram showing an operation status of a microbubble discharge unit in accordance with an example of the present disclosure.

Referring to FIG. 2 and FIG. 3, the a plurality of microbubble discharge unit 400 may be provided at a lower part within the liquid tank 100 as being connected to the gas supply line unit 300 and configured to discharge the gas injected through the distribution pipe 340 in the form of microbubbles, but may not be limited thereto. Herein, desirably, the microbubble discharge unit 400 may be provided at a position lower than a water level of the liquid accommodated in the liquid tank 100.

In accordance with an embodiment of the present disclosure, the microbubbles discharged through the microbubble discharge unit 400 may have an average diameter of from about 1 nm to about 1,000 μm, but may not be limited thereto. By way of example, the microbubbles may have an average diameter of from about 1 nm to about 1,000 μm, from about 10 nm to about 1,000 μm, from about 100 nm to about 1,000 μm, from about 300 nm to about 1,000 μm, from about 500 nm to about 1,000 μm, from about 700 nm to about 1,000 μm, from about 900 nm to about 1,000 μm, from about 1 μm to about 1,000 μm, from about 10 μm to about 1,000 μm, from about 100 μm to about 1,000 μm, from about 300 μm to about 1,000 μm, from about 500 μm to about 1,000 μm, from about 700 μm to about 1,000 μm, from about 900 μm to about 1,000 μm, from about 1 nm to about 900 μm, from about 10 nm to about 900 μm, from about 100 nm to about 900 μm, from about 300 nm to about 900 μm, from about 500 nm to about 900 μm, from about 700 nm to about 900 μm, from about 900 nm to about 900 μm, from about 1 μm to about 900 μm, from about 10 μm to about 900 μm, from about 100 μm to about 900 μm, from about 300 μm to about 900 μm, from about 500 μm to about 900 μm, from about 700 μm to about 900 μm, from about 1 nm to about 700 μm, from about 10 nm to about 700 μm, from about 100 nm to about 700 μm, from about 300 nm to about 700 μm, from about 500 nm to about 700 μm, from about 700 nm to about 700 μm, from about 900 nm to about 700 μm, from about 1 μm to about 700 μm, from about 10 μm to about 700 μm, from about 100 μm to about 700 μm, from about 300 μm to about 700 μm, from about 500 μm to about 700 μm, from about 1 nm to about 500 μm, from about 10 nm to about 500 μm, from about 100 nm to about 500 μm, from about 300 nm to about 500 μm, from about 500 nm to about 500 μm, from about 700 nm to about 500 μm, from about 900 nm to about 500 μm, from about 1 μm to about 500 μm, from about 10 μm to about 500 μm, from about 100 μm to about 500 μm, from about 300 μm to about 500 μm, from about 1 nm to about 300 μm, from about 10 nm to about 300 μm, from about 100 nm to about 300 μm, from about 300 nm to about 300 μm, from about 500 nm to about 300 μm, from about 700 nm to about 300 μm, from about 900 nm to about 300 μm, from about 1 μm to about 300 μm, from about 10 μm to about 300 μm, from about 100 μm to about 300 μm, from about 1 nm to about 100 μm, from about 10 nm to about 100 μm, from about 100 nm to about 100 μm, from about 300 nm to about 100 μm, from about 500 nm to about 100 μm, from about 700 nm to about 100 μm, from about 900 nm to about 100 μm, from about 1 μm to about 100 μm, from about 10 μm to about 100 μm, from about 1 nm to about 10 μm, from about 10 nm to about 10 μm, from about 100 nm to about 10 μm, from about 300 nm to about 10 μm, from about 500 nm to about 10 μm, from about 700 nm to about 10 μm, from about 900 nm to about 10 μm, from about 1 μm to about 10 μm, from about 1 nm to about 1 μm, from about 10 nm to about 1 μm, from about 100 nm to about 1 μm, from about 300 nm to about 1 μm, from about 500 nm to about 1 μm, from about 700 nm to about 1 μm, from about 900 nm to about 1 μm, from about 1 nm to about 900 nm, from about 10 nm to about 900 nm, from about 100 nm to about 900 nm, from about 300 nm to about 900 nm, from about 500 nm to about 900 nm, from about 700 nm to about 900 nm, from about 1 nm to about 700 nm, from about 10 nm to about 700 nm, from about 100 nm to about 700 nm, from about 300 nm to about 700 nm, from about 500 nm to about 700 nm, from about 1 nm to about 500 nm, from about 10 nm to about 500 nm, from about 100 nm to about 500 nm, from about 300 nm to about 500 nm, from about 1 nm to about 300 nm, from about 10 nm to about 300 nm, from about 100 nm to about 300 nm, from about 1 nm to about 100 nm, from about 10 nm to about 100 nm, or from about 1 nm to about 10 nm, but may not be limited thereto.

In accordance with an embodiment of the present disclosure, the microbubble discharge unit 400 may include a porous pipe body 410 in which micropores are formed, communicating with the inside to allow the gas injected through the distribution pipe 340 to be discharged in the form of microbubbles, a body unit 420 provided to be connected to one side of the porous pipe body 410 and configured to generate vibrations by a ultrasonic vibrator 426 provided therein are propagated, and a vibration transfer unit 430 attached to the one side of the porous pipe body 410 and configured to transfer the ultrasonic vibrations propagated from the body unit 420 to the porous pipe body 410, but may not be limited thereto.

In accordance with an embodiment of the present disclosure, the porous pipe body 410 including micro pores may have holes each having a size of from about 1 nm to about 1 mm, but may not be limited thereto. By way of example, the porous pipe body may have holes each having a size of from about 1 nm to about 1 mm, from about 10 nm to about 1 mm, from about 100 nm to about 1 mm, from about 300 nm to about 1 mm, from about 500 nm to about 1 mm, from about 700 nm to about 1 mm, from about 900 nm to about 1 mm, from about 1 μm to about 1 mm, from about 10 μm to about 1 mm, from about 100 μm to about 1 mm, from about 300 μm to about 1 mm, from about 500 μm to about 1 mm, from about 700 μm to about 1 mm, from about 900 μm to about 1 mm, from about 1 nm to about 900 μm, from about 10 nm to about 900 μm, from about 100 nm to about 900 μm, from about 300 nm to about 900 μm, from about 500 nm to about 900 μm, from about 700 nm to about 900 μm, from about 900 nm to about 900 μm, from about 1 μm to about 900 μm, from about 10 μm to about 900 μm, from about 100 μm to about 900 μm, from about 300 μm to about 900 μm, from about 500 μm to about 900 μm, from about 700 μm to about 900 μm, from about 1 nm to about 700 μm, from about 10 nm to about 700 μm, from about 100 nm to about 700 μm, from about 300 nm to about 700 μm, from about 500 nm to about 700 μm, from about 700 nm to about 700 μm, from about 900 nm to about 700 μm, from about 1 μm to about 700 μm, from about 10 μm to about 700 μm, from about 100 μm to about 700 μm, from about 300 μm to about 700 μm, from about 500 μm to about 700 μm, from about 1 nm to about 500 μm, from about 10 nm to about 500 μm, from about 100 nm to about 500 μm, from about 300 nm to about 500 μm, from about 500 nm to about 500 μm, from about 700 nm to about 500 μm, from about 900 nm to about 500 μm, from about 1 μm to about 500 μm, from about 10 μm to about 500 μm, from about 100 μm to about 500 μm, from about 300 μm to about 500 μm, from about 1 nm to about 300 μm, from about 10 nm to about 300 μm, from about 100 nm to about 300 μm, from about 300 nm to about 300 μm, from about 500 nm to about 300 μm, from about 700 nm to about 300 μm, from about 900 nm to about 300 μm, from about 1 μm to about 300 μm, from about 10 μm to about 300 μm, from about 100 μm to about 300 μm, from about 1 nm to about 100 μm, from about 10 nm to about 100 μm, from about 100 nm to about 100 μm, from about 300 nm to about 100 μm, from about 500 nm to about 100 μm, from about 700 nm to about 100 μm, from about 900 nm to about 100 μm, from about 1 μm to about 100 μm, from about 10 μm to about 100 μm, from about 1 nm to about 10 μm, from about 10 nm to about 10 μm, from about 100 nm to about 10 μm, from about 300 nm to about 10 μm, from about 500 nm to about 10 μm, from about 700 nm to about 10 μm, from about 900 nm to about 10 μm, from about 1 μm to about 10 μm, from about 1 nm to about 1 μm, from about 10 nm to about 1 μm, from about 100 nm to about 1 μm, from about 300 nm to about 1 μm, from about 500 nm to about 1 μm, from about 700 nm to about 1 μm, from about 900 nm to about 1 μm, from about 1 nm to about 900 nm, from about 10 nm to about 900 nm, from about 100 nm to about 900 nm, from about 300 nm to about 900 nm, from about 500 nm to about 900 nm, from about 700 nm to about 900 nm, from about 1 nm to about 700 nm, from about 10 nm to about 700 nm, from about 100 nm to about 700 nm, from about 300 nm to about 700 nm, from about 500 nm to about 700 nm, from about 1 nm to about 500 nm, from about 10 nm to about 500 nm, from about 100 nm to about 500 nm, from about 300 nm to about 500 nm, from about 1 nm to about 300 nm, from about 10 nm to about 300 nm, from about 100 nm to about 300 nm, from about 1 nm to about 100 nm, from about 10 nm to about 100 nm, or from about 1 nm to about 10 nm, but may not be limited thereto.

In accordance with an embodiment of the present disclosure, the porous pipe body 410 may further include a front closing cap 440 and a rear closing cap 450, but may not be limited thereto. A coupling nut unit 441 is formed on one side of the front closing cap 440 and coupled to a front end of the porous pipe body 410 such that the coupling nut unit 441 can be accommodated on the front end side within the porous pipe body 410. In this case, the porous pipe body 410 and the front closing cap 440 may be coupled in a state where a sealing ring (not illustrated) is provided therebetween in order to maintain airtightness, but may not be limited thereto. A bolt unit 451 is provided on one side of the rear closing cap 450 and coupled to a rear end side of the porous pipe body 410 such that the bolt unit 451 can be intruded from the rear end side to the inside of the porous pipe body 410 so as to be clamped to the coupling nut unit 441 of the front closing cap 440, but may not be limited thereto. In this case, desirably, the porous pipe body 410 and the rear closing cap 450 may also be coupled in a state where a sealing ring (not illustrated) is provided therebetween in order to maintain airtightness. The rear closing cap 450 may include a plurality of gas through-holes 452 around the bolt unit 451, and a gas introduced through the gas through-holes 452 may pass through the inside of the porous pipe body 410 and then may be discharged in the form of microbubbles through the pores of the porous pipe body 410, but may not be limited thereto. Further, a curved recess groove 453 is formed along an outer peripheral surface of the rear closing cap 450, and the rear closing cap 450 including the curved recess groove 453 may be connected to a front end of the body unit 420, but may not be limited thereto. The vibration transfer unit 430 is attached to an outer side of the rear closing cap 450 of the porous pipe body 410 and configured to transfer ultrasonic vibrations generated from the body unit 420 to the porous pipe body 410, but may not be limited thereto. By way of example, the vibration transfer unit 430 may include a vibration pin to be vibrated by ultrasonic waves in an outward direction to the ultrasonic vibrator 426, and ultrasonic vibrations may be transferred to the porous pipe body 410 by the vibration pin, but may not be limited thereto.

In accordance with an embodiment of the present disclosure, the body unit 420 may include a main body pipe 421, an elastic fixing ring 422, and a connection pipe body 423, but may not be limited thereto. The main body pipe 421 may be formed in pipe shape having a predetermined diameter, and a curved coupling groove 424 is formed on its inner peripheral surface of a front end. When the rear end of the porous pipe body 410 is connected to the front end of the body unit 420, the curved recess groove 453 of the rear closing cap 450 may be confronted with the curved coupling groove 424 of the main body pipe 421, but may not be limited thereto. In this case, the elastic fixing ring 422 may be provided and located between the curved recess groove 453 of the rear closing cap 450 and the curved coupling groove 424 of the main body pipe 421 confronted with each other, so that the porous pipe body 410 is movably fixed to the body unit 420, but may not be limited thereto. The elastic fixing ring 422 fixes the porous pipe body 410 and the body unit 420, and also maintains airtightness between the porous pipe body 410 and the body unit 420. Further, a rear end of the main body pipe 421 is screw-coupled to the connection pipe body 423, and the ultrasonic vibrator 426 is provided at the center of the connection pipe body 423. A gas inlet hole 425 connected to the distribution pipe 340 of the gas supply line unit 300 may be formed around the ultrasonic vibrator 426, but may not be limited thereto.

The ultrasonic vibrator 426 is the same as a typical ultrasonic vibrator, and thus, detailed explanation thereof will be omitted herein. The ultrasonic vibrator 426 may be selectively operated by external control, but may not be limited thereto. By way of example, the ultrasonic vibrator may have a frequency of from about 1 Hz to about 300 MHz, but may not be limited thereto. By way of example, the ultrasonic vibrator may have a frequency of from about 1 Hz to about 300 MHz, from about 10 Hz to about 300 MHz, from about 100 Hz to about 300 MHz, from about 300 Hz to about 300 MHz, from about 500 Hz to about 300 MHz, from about 700 Hz to about 300 MHz, from about 900 Hz to about 300 MHz, from about 1 kHz to about 300 MHz, from about 10 kHz to about 300 MHz, from about 100 kHz to about 300 MHz, from about 300 kHz to about 300 MHz, from about 500 kHz to about 300 MHz, from about 700 kHz to about 300 MHz, from about 900 kHz to about 300 MHz, from about 1 MHz to about 300 MHz, from about 10 MHz to about 300 MHz, from about 100 MHz to about 300 MHz, from about 1 Hz to about 100 MHz, from about 10 Hz to about 100 MHz, from about 100 Hz to about 100 MHz, from about 300 Hz to about 100 MHz, from about 500 Hz to about 100 MHz, from about 700 Hz to about 100 MHz, from about 900 Hz to about 100 MHz, from about 1 kHz to about 100 MHz, from about 10 kHz to about 100 MHz, from about 100 kHz to about 100 MHz, from about 300 kHz to about 100 MHz, from about 500 kHz to about 100 MHz, from about 700 kHz to about 100 MHz, from about 900 kHz to about 100 MHz, from about 1 MHz to about 100 MHz, from about 10 MHz to about 100 MHz, from about 1 Hz to about 10 MHz, from about 10 Hz to about 10 MHz, from about 100 Hz to about 10 MHz, from about 300 Hz to about 10 MHz, from about 500 Hz to about 10 MHz, from about 700 Hz to about 10 MHz, from about 900 Hz to about 10 MHz, from about 1 kHz to about 10 MHz, from about 10 kHz to about 10 MHz, from about 100 kHz to about 10 MHz, from about 300 kHz to about 10 MHz, from about 500 kHz to about 10 MHz, from about 700 kHz to about 10 MHz, from about 900 kHz to about 10 MHz, from about 1 MHz to about 10 MHz, from about 1 Hz to about 1 MHz, from about 10 Hz to about 1 MHz, from about 100 Hz to about 1 MHz, from about 300 Hz to about 1 MHz, from about 500 Hz to about 1 MHz, from about 700 Hz to about 1 MHz, from about 900 Hz to about 1 MHz, from about 1 kHz to about 1 MHz, from about 10 kHz to about 1 MHz, from about 100 kHz to about 1 MHz, from about 300 kHz to about 1 MHz, from about 500 kHz to about 1 MHz, from about 700 kHz to about 1 MHz, from about 900 kHz to about 1 MHz, from about 1 Hz to about 900 kHz, from about 10 Hz to about 900 kHz, from about 100 Hz to about 900 kHz, from about 300 Hz to about 900 kHz, from about 500 Hz to about 900 kHz, from about 700 Hz to about 900 kHz, from about 900 Hz to about 900 kHz, from about 1 kHz to about 900 kHz, from about 10 kHz to about 900 kHz, from about 100 kHz to about 900 kHz, from about 300 kHz to about 900 kHz, from about 500 kHz to about 900 kHz, from about 700 kHz to about 900 kHz, from about 1 Hz to about 700 kHz, from about 10 Hz to about 700 kHz, from about 100 Hz to about 700 kHz, from about 300 Hz to about 700 kHz, from about 500 Hz to about 700 kHz, from about 700 Hz to about 700 kHz, from about 900 Hz to about 700 kHz, from about 1 kHz to about 700 kHz, from about 10 kHz to about 700 kHz, from about 100 kHz to about 700 kHz, from about 300 kHz to about 700 kHz, from about 500 kHz to about 700 kHz, from about 1 Hz to about 500 kHz, from about 10 Hz to about 500 kHz, from about 100 Hz to about 500 kHz, from about 300 Hz to about 500 kHz, from about 500 Hz to about 500 kHz, from about 700 Hz to about 500 kHz, from about 900 Hz to about 500 kHz, from about 1 kHz to about 500 kHz, from about 10 kHz to about 500 kHz, from about 100 kHz to about 500 kHz, from about 300 kHz to about 500 kHz, from about 1 Hz to about 300 kHz, from about 10 Hz to about 300 kHz, from about 100 Hz to about 300 kHz, from about 300 Hz to about 300 kHz, from about 500 Hz to about 300 kHz, from about 700 Hz to about 300 kHz, from about 900 Hz to about 300 kHz, from about 1 kHz to about 300 kHz, from about 10 kHz to about 300 kHz, from about 100 kHz to about 300 kHz, from about 1 Hz to about 100 kHz, from about 10 Hz to about 100 kHz, from about 100 Hz to about 100 kHz, from about 300 Hz to about 100 kHz, from about 500 Hz to about 100 kHz, from about 700 Hz to about 100 kHz, from about 900 Hz to about 100 kHz, from about 1 kHz to about 100 kHz, from about 10 kHz to about 100 kHz, from about 1 Hz to about 10 kHz, from about 10 Hz to about 10 kHz, from about 100 Hz to about 10 kHz, from about 300 Hz to about 10 kHz, from about 500 Hz to about 10 kHz, from about 700 Hz to about 10 kHz, from about 900 Hz to about 10 kHz, from about 1 kHz to about 10 kHz, from about 1 Hz to about 1 kHz, from about 10 Hz to about 1 kHz, from about 100 Hz to about 1 kHz, from about 300 Hz to about 1 kHz, from about 500 Hz to about 1 kHz, from about 700 Hz to about 1 kHz, from about 900 Hz to about 1 kHz, from about 1 Hz to about 900 Hz, from about 10 Hz to about 900 Hz, from about 100 Hz to about 900 Hz, from about 300 Hz to about 900 Hz, from about 500 Hz to about 900 Hz, from about 700 Hz to about 900 Hz, from about 1 Hz to about 700 Hz, from about 10 Hz to about 700 Hz, from about 100 Hz to about 700 Hz, from about 300 Hz to about 700 Hz, from about 500 Hz to about 700 Hz, from about 1 Hz to about 500 Hz, from about 10 Hz to about 500 Hz, from about 100 Hz to about 500 Hz, from about 300 Hz to about 500 Hz, from about 1 Hz to about 300 Hz, from about 10 Hz to about 300 Hz, from about 100 Hz to about 300 Hz, from about 1 Hz to about 100 Hz, from about 10 Hz to about 100 Hz, or from about 1 Hz to about 10 Hz, but may not be limited thereto.

In accordance with an embodiment of the present disclosure, the liquid tank 100 may further comprise a heating device or a cooling device, but may not be limited thereto. The heating device or the cooling device may be provided inside or outside of the liquid tank 100, but may not be limited thereto.

If the liquid tank 100 further includes the heating device, for example, when microbubbles are generated, it may be difficult for a high-viscosity material to form microbubbles due to its viscosity. In this case, since the liquid tank 100 further includes the heating device, the viscosity of the high-viscosity material can be lowered to an appropriate level by adjusting a temperature, so that microbubbles can be generated. By way of example, the heating device may include a heating coil using a resistance heat and provided on the outside of the liquid tank and allow a current to flow to heat the high-viscosity material at an appropriate temperature, but may not be limited thereto. The high-viscosity material may include a member selected from the group consisting of fossil fuels, bio fuels, polymers, and combinations thereof, but may not be limited thereto. By way of example, the high-viscosity material may include a member selected from the group consisting of lubricating oil, polymers, gasoline, diesel, bunker oil, bio ethanol, bio methanol, bio diesel, and combinations thereof, but may not be limited thereto. By way of example, as for the lubricating oil, microbubbles are generated within the lubricating oil, so that a lubrication property can be improved. Conventionally, there has been used a method of lowering a viscosity of the lubricating oil by adjusting a temperature of the lubricating oil in order to improve the lubrication property. However, the above-described method has a bad influence on formation of an oil film by the lubricating oil and thus reduces the lubrication property. If a microbubble is generated within the lubricating oil, a solid surface in contact with a polar solvent is negatively charged due to an electric double layer effect, and thus, a liquid around the solid surface is positively charged. Since a surface of the microbubble is negatively charged, the microbubble attaches itself to a solid wall by an electrical attractive force. Thus, a gas phase is formed around a surface of the solid wall and causes a wall slip phenomenon between the solid wall and a liquid surface. The liquid in which the microbubble is formed moves along the gas phase. Therefore, lubricating oil in which the microbubbles are generated can smoothly move as compared with lubricating oil without microbubbles and thus can reduce friction. Such a friction reduction property causes a reduction in abrasion of a surface and generation of heat. Therefore, it is possible to obtain a better lubrication property. Further, as generally known in the art, a liquid including microbubbles has the same viscosity as a liquid without microbubbles, and thus, lubricating oil including microbubbles can obtain the lubricating oil improved in electrical resistance, mechanical strength, insulating property, and lubrication property as compared with conventional lubricating oil by using a wall slip phenomenon while maintaining a viscosity required for forming an oil film.

If the liquid tank 100 further includes the cooling device, for example, when microbubbles are generated in order to improve efficiency of a fuel, the fuel may be continuously evaporated due to its volatility while the microbubbles are generated. In order to lower the volatility of the fuel, the cooling device may be provide at the liquid tank, or microbubbles may be generated in the fuel and then an additive may be mixed therein, but may not be limited thereto. The fuel may include a member selected from the group consisting of fossil fuels, bio fuels, and combinations thereof, but may not be limited thereto. By way of example, the fossil fuel may include a member selected from the group consisting of gasoline, diesel, lubricating oil, bunker oil, and combinations thereof, but may not be limited thereto. By way of example, the bio fuel may include a member selected from the group consisting of bio ethanol, bio methanol, bio diesel, and combinations thereof, but may not be limited thereto. If the cooling device is provided at the liquid tank 100, for example, the cooling device may be provided inside or outside of the liquid tank, but may not be limited thereto. The cooling device may be cooled by coolant circulated through a cooling channel. The coolant may be a air-cooling using cold air, but may not be limited thereto. Further, the volatility of the fuel may be lowered by generating microbubbles in the fuel and then mixing an additive therein, but may not be limited thereto. The volatility of the fuel may be determined by the additive added to the fuel as well as a property of the fuel. By way of example, if the fuel is gasoline, the volatility may be determined by mixing of butane which is dissolved in the gasoline and contributing to regulation of a steam pressure of the gasoline and improvement of an octane number. Therefore, microbubbles may be generated before butane is mixed, and then, the butane may be dissolved in the fuel, so that the problem caused by the volatility of the fuel may be suppressed, but may not be limited thereto.

According to the configuration of the present disclosure as described above, the porous pipe body 410 configured to discharge a gas supplied from the outside in the form of microbubbles may be vibrated when receiving ultrasonic vibrations propagated from the ultrasonic vibrator 426, and thus, the microbubbles are detached from the porous pipe body 410 before the microbubbles attach themselves to a surface of the porous pipe body 410 or aggregated with another, so that it is possible to produce bubble water having the maximized amount of dissolved bubbles in the liquid accommodated in the liquid tank 100. Further, since it is not necessary to inject a high-pressure gas in order to generate microbubbles, it is possible to mass-produce bubble water by a relatively simple system, resulting in a significant reduction in production cost. Since a residual gas which is not mixed with the liquid is allowed to remain in the liquid tank 100 and the atmosphere within the liquid tank 100 is maintained in a gas-saturated state, it is possible to maximize the dissolved gas content of bubble water and also possible to maintain a sufficient dissolved gas content even after time passes. Further, since the generated microbubbles are very small and relatively uniform in size, the microbubbles can be efficiently dissolved in the liquid and a dissolved gas ratio of the bubble water can be achieved in a relatively short time. Meanwhile, since a cooling device or a heating device is further provided at the device for producing microbubbles, by generating microbubbles within a high-viscosity material and a fuel, it is possible to enhance properties of the high-viscosity material such as electrical resistance, mechanical strength, insulating property, lubrication property, etc. and improve energy efficiency of the fuel.

In a second aspect of the present disclosure, there is provided a microbubble discharge unit using a ultrasonic vibrator including: a body unit provided to be connected to one side of a porous pipe body and configured to generate vibrations by a ultrasonic vibrator provided therein; and a vibration transfer unit attached to the one side of the porous pipe body and configured to transfer ultrasonic vibrations generated by the body unit to the porous pipe body, and the ultrasonic vibrations are applied to the porous pipe body via the vibration transfer unit so as to detach microbubbles generated by the porous pipe body.

In accordance with an embodiment of the present disclosure, the porous pipe body may have holes each having a size of from about 1 nm to about 1 mm, but may not be limited thereto. By way of example, the porous pipe body may have holes each having a size of from about 1 nm to about 1 mm, from about 10 nm to about 1 mm, from about 100 nm to about 1 mm, from about 300 nm to about 1 mm, from about 500 nm to about 1 mm, from about 700 nm to about 1 mm, from about 900 nm to about 1 mm, from about 1 µm to about 1 mm, from about 10 µm to about 1 mm, from about 100 µm to about 1 mm, from about 300 µm to about 1 mm, from about 500 µm to about 1 mm, from about 700 µm to about 1 mm, from about 900 µm to about 1 mm, from about 1 nm to about 900 µm, from about 10 nm to about 900 µm, from about 100 nm to about 900 µm, from about 300 nm to about 900 µm, from about 500 nm to about 900 µm, from about 700 nm to about 900 µm, from about 900 nm to about 900 µm, from about 1 µm to about 900 µm, from about 10 µm to about 900 µm, from about 100 µm to about 900 µm, from about 300 µm to about 900 µm, from about 500 µm to about 900 µm, from about 700 µm to about 900 µm, from about 1 nm to about 700 µm, from about 10 nm to about 700 µm, from about 100 nm to about 700 µm, from about 300 nm to about 700 µm, from about 500 nm to about 700 µm, from about 700 nm to about 700 µm, from about 900 nm to about 700 µm, from about 1 µm to about 700 µm, from about 10 µm to about 700 µm, from about 100 µm to about 700 µm, from about 300 µm to about 700 µm, from about 500 µm to about 700 µm, from about 1 nm to about 500 µm, from about 10 nm to about 500 µm, from about 100 nm to about 500 µm, from about 300 nm to about 500 µm, from about 500 nm to about 500 µm, from about 700 nm to about 500 µm, from about 900 nm to about 500 µm, from about 1 µm to about 500 µm, from about 10 µm to about 500 µm, from about 100 µm to about 500 µm, from about 300 µm to about 500 µm, from about 1 nm to about 300 µm, from about 10 nm to about 300 µm, from about 100 nm to about 300 µm, from about 300 nm to about 300 µm, from about 500 nm to about 300 µm, from about 700 nm to about 300 µm, from about 900 nm to about 300 µm, from about 1 µm to about 300 µm, from about 10 µm to about 300 µm, from about 100 µm to about 300 µm, from about 1 nm to about 100 µm, from about 10 nm to about 100 µm, from about 100 nm to about 100 µm, from about 300 nm to about 100 µm, from about 500 nm to about 100 µm, from about 700 nm to about 100 µm, from about 900 nm to about 100 µm, from about 1 µm to about 100 µm, from about 10 µm to about 100 µm, from about 1 nm to about 10 µm, from about 10 nm to about 10 µm, from about 100 nm to about 10 µm, from about 300 nm to about 10 µm, from about 500 nm to about 10 µm, from about 700 nm to about 10 µm, from about 900 nm to about 10 µm, from about 1 µm to about 10 µm, from about 1 nm to about 1 µm, from about 10 nm to about 1 µm, from about 100 nm to about 1 µm, from about 300 nm to about 1 µm, from about 500 nm to about 1 µm, from about 700 nm to about 1 µm, from about 900 nm to about 1 µm, from about 1 nm to about 900 nm, from about 10 nm to about 900 nm, from about 100 nm to about 900 nm, from about 300 nm to about 900 nm, from about 500 nm to about 900 nm, from about 700 nm to about 900 nm, from about 1 nm to about 700 nm, from about 10 nm to about 700 nm, from about 100 nm to about 700 nm, from about 300 nm to about 700 nm, from about 500 nm to about 700 nm, from about 1 nm to about 500 nm, from about 10 nm to about 500 nm, from about 100 nm to about 500 nm, from about 300 nm to about 500 nm, from about 1 nm to about 300 nm, from about 10 nm to about 300 nm, from about 100 nm to about 300 nm, from about 1 nm to about 100 nm, from about 10 nm to about 100 nm, or from about 1 nm to about 10 nm, but may not be limited thereto.

In accordance with an embodiment of the present disclosure, the porous pipe body may include a front closing cap in which a coupling nut unit formed on one side of the front closing cap is coupled to be accommodated in a front end side of the porous pipe body; and a rear closing cap in which a bolt unit formed on one side of the rear closing cap is intruded from a rear end side to the inside of the porous pipe body, so as to be clamped to the coupling nut unit of the front closing cap, a plurality of gas through-holes are formed around the bolt unit, and a curved recess groove is formed along an outer peripheral surface of the rear closing cap, but may not be limited thereto. By way of example, the coupling nut unit may be provided on one side of the front closing cap and coupled to the front end of the porous pipe body such that the coupling nut unit can be accommodated in the front end side of the porous pipe body. In this case, the porous pipe body and the front closing cap may be coupled in a state where a sealing ring is provided therebetween in order to maintain airtightness, but may not be limited thereto. By way of example, the bolt unit may be provided on one side of the rear closing cap and coupled to a rear end side of the porous pipe body such that the bolt unit can be intruded from the rear end side to the inside of the porous pipe body, so as to be clamped to the coupling nut unit of the front closing cap, but may not be limited thereto. In this case, desirably, the porous pipe body and the rear closing cap may also be coupled in a state where a sealing ring is provided therebetween in order to maintain airtightness. The rear closing cap may include a plurality of gas through-holes around the bolt unit, and a gas introduced through the gas through-holes may pass through the inside of the porous pipe body and then may be discharged in the form of microbubbles through the pores of the porous pipe body, but may not be limited thereto. By way of example, the gas may include a gas selected from the group consisting of hydrogen, oxygen, carbon dioxide, carbon monoxide, nitrogen, xenon, argon, neon, air, ozone, krypton, helium, a nitrogen-containing compound gas, a carbon-containing compound gas, and combinations thereof, but may not be limited thereto. Further, the curved recess groove may be formed along the outer peripheral surface of the rear closing cap, and the rear closing cap including the curved recess groove may be connected to the front end of the body unit, but may not be limited thereto. The vibration transfer unit may be attached to an outer side of the rear closing cap of the porous pipe body and configured to transfer ultrasonic vibrations generated from the body unit to the porous pipe body, but may not be limited thereto. By way of example, in the vibration transfer unit may include a vibration pin to be vibrated by ultrasonic waves in an outward direction to the ultrasonic vibrator, and ultrasonic vibrations may be transferred to the porous pipe body by the vibration pin, but may not be limited thereto.

In accordance with an embodiment of the present disclosure, the body unit may include: a main body pipe which is formed in a pipe shape and a curved coupling groove is formed on a front side along its inner peripheral surface, and the rear end of the porous pipe body is inserted into and fixed to the front side on which the curved coupling groove is formed; an elastic fixing ring which is movably located between the curved coupling groove of the main body pipe and the curved recess groove of the rear closing cap so as to fix the porous pipe body to the main body pipe; and a connection pipe body which is screw-coupled to a rear end of the main body pipe and in which a ultrasonic vibrator is provided at the center and a gas inlet hole connected to the gas supply line is formed around the ultrasonic vibrator, but may not be limited thereto. The main body pipe may be formed in a pipe shape having a predetermined diameter, and the curved coupling groove may be formed on the inner peripheral surface of the front end. When the rear end of the porous pipe body is connected to the front end of the body unit, the curved recess groove of the rear closing cap may be confronted with the curved coupling groove of the main body pipe, but may not be limited thereto. In this case, the elastic fixing ring may be provided and located between the curved recess groove of the rear closing cap and the curved coupling groove of the main body pipe confronted with each other, so that the porous pipe body is movably fixed to the body unit, but may not be limited thereto. The elastic fixing ring may fix the porous pipe body and the body unit, and also maintain airtightness between the porous pipe body and the body unit. Further, the rear end of the main body pipe may be screw-coupled to the connection pipe body, and the ultrasonic vibrator may be provided at the center of the connection pipe body, but may not be limited thereto.

In accordance with an embodiment of the present disclosure, the ultrasonic vibrator is the same as a typical ultrasonic vibrator, and thus, detailed explanation thereof will be omitted herein. The ultrasonic vibrator may be selectively operated by external control, but may not be limited thereto. By way of example, the ultrasonic vibrator may have a frequency of from about 1 Hz to about 300 MHz, but may not be limited thereto. By way of example, the ultrasonic vibrator may have a frequency of from about 1 Hz to about 300 MHz, from about 10 Hz to about 300 MHz, from about 100 Hz to about 300 MHz, from about 300 Hz to about 300 MHz, from about 500 Hz to about 300 MHz, from about 700 Hz to about 300 MHz, from about 900 Hz to about 300 MHz, from about 1 kHz to about 300 MHz, from about 10 kHz to about 300 MHz, from about 100 kHz to about 300 MHz, from about 300 kHz to about 300 MHz, from about 500 kHz to about 300 MHz, from about 700 kHz to about 300 MHz, from about 900 kHz to about 300 MHz, from about 1 MHz to about 300 MHz, from about 10 MHz to about 300 MHz, from about 100 MHz to about 300 MHz, from about 1 Hz to about 100 MHz, from about 10 Hz to about 100 MHz, from about 100 Hz to about 100 MHz, from about 300 Hz to about 100 MHz, from about 500 Hz to about 100 MHz, from about 700 Hz to about 100 MHz, from about 900 Hz to about 100 MHz, from about 1 kHz to about 100 MHz, from about 10 kHz to about 100 MHz, from about 100 kHz to about 100 MHz, from about 300 kHz to about 100 MHz, from about 500 kHz to about 100 MHz, from about 700 kHz to about 100 MHz, from about 900 kHz to about 100 MHz, from about 1 MHz to about 100 MHz, from about 10 MHz to about 100 MHz, from about 1 Hz to about 10 MHz, from about 10 Hz to about 10 MHz, from about 100 Hz to about 10 MHz, from about 300 Hz to about 10 MHz, from about 500 Hz to about 10 MHz, from about 700 Hz to about 10 MHz, from about 900 Hz to about 10 MHz, from about 1 kHz to about 10 MHz, from about 10 kHz to about 10 MHz, from about 100 kHz to about 10 MHz, from about 300 kHz to about 10 MHz, from about 500 kHz to about 10 MHz, from about 700 kHz to about 10 MHz, from about 900 kHz to about 10 MHz, from about 1 MHz to about 10 MHz, from about 1 Hz to about 1 MHz, from about 10 Hz to about 1 MHz, from about 100 Hz to about 1 MHz, from about 300 Hz to about 1 MHz, from about 500 Hz to about 1 MHz, from about 700 Hz to about 1 MHz, from about 900 Hz to about 1 MHz, from about 1 kHz to about 1 MHz, from about 10 kHz to about 1 MHz, from about 100 kHz to about 1 MHz, from about 300 kHz to about 1 MHz, from about 500 kHz to about 1 MHz, from about 700 kHz to about 1 MHz, from about 900 kHz to about 1 MHz, from about 1 Hz to about 900 kHz, from about 10 Hz to about 900 kHz, from about 100 Hz to about 900 kHz, from about 300 Hz to about 900 kHz, from about 500 Hz to about 900 kHz, from about 700 Hz to about 900 kHz, from about 900 Hz to about 900 kHz, from about 1 kHz to about 900 kHz, from about 10 kHz to about 900 kHz, from about 100 kHz to about 900 kHz, from about 300 kHz to about 900 kHz, from about 500 kHz to about 900 kHz, from about 700 kHz to about 900 kHz, from about 1 Hz to about 700 kHz, from about 10 Hz to about 700 kHz, from about 100 Hz to about 700 kHz, from about 300 Hz to about 700 kHz, from about 500 Hz to about 700 kHz, from about 700 Hz to about 700 kHz, from about 900 Hz to about 700 kHz, from about 1 kHz to about 700 kHz, from about 10 kHz to about 700 kHz, from about 100 kHz to about 700 kHz, from about 300 kHz to about 700 kHz, from about 500 kHz to about 700 kHz, from about 1 Hz to about 500 kHz, from about 10 Hz to about 500 kHz, from about 100 Hz to about 500 kHz, from about 300 Hz to about 500 kHz, from about 500 Hz to about 500 kHz, from about 700 Hz to about 500 kHz, from about 900 Hz to about 500 kHz, from about 1 kHz to about 500 kHz, from about 10 kHz to about 500 kHz, from about 100 kHz to about 500 kHz, from about 300 kHz to about 500 kHz, from about 1 Hz to about 300 kHz, from about 10 Hz to about 300 kHz, from about 100 Hz to about 300 kHz, from about 300 Hz to about 300 kHz, from about 500 Hz to about 300 kHz, from about 700 Hz to about 300 kHz, from about 900 Hz to about 300 kHz, from about 1 kHz to about 300 kHz, from about 10 kHz to about 300 kHz, from about 100 kHz to about 300 kHz, from about 1 Hz to about 100 kHz, from about 10 Hz to about 100 kHz, from about 100 Hz to about 100 kHz, from about 300 Hz to about 100 kHz, from about 500 Hz to about 100 kHz, from about 700 Hz to about 100 kHz, from about 900 Hz to about 100 kHz, from about 1 kHz to about 100 kHz, from about 10 kHz to about 100 kHz, from about 1 Hz to about 10 kHz, from about 10 Hz to about 10 kHz, from about 100 Hz to about 10 kHz, from about 300 Hz to about 10 kHz, from about 500 Hz to about 10 kHz, from about 700 Hz to about 10 kHz, from about 900 Hz to about 10 kHz, from about 1 kHz to about 10 kHz, from about 1 Hz to about 1 kHz, from about 10 Hz to about 1 kHz, from about 100 Hz to about 1 kHz, from about 300 Hz to about 1 kHz, from about 500 Hz to about 1 kHz, from about 700 Hz to about 1 kHz, from about 900 Hz to about 1 kHz, from about 1 Hz to about 900 Hz, from about 10 Hz to about 900 Hz, from about 100 Hz to about 900 Hz, from about 300 Hz to about 900 Hz, from about 500 Hz to about 900 Hz, from about 700 Hz to about 900 Hz, from about 1 Hz to about 700 Hz, from about 10 Hz to about 700 Hz, from about 100 Hz to about 700 Hz, from about 300 Hz to about 700 Hz, from about 500 Hz to about 700 Hz, from about 1 Hz to about 500 Hz, from about 10 Hz to about 500 Hz, from about 100 Hz to about 500 Hz, from about 300 Hz to about 500 Hz, from about 1 Hz to about 300 Hz, from about 10 Hz to about 300 Hz, from about 100 Hz to about 300 Hz, from about 1 Hz to about 100 Hz, from about 10 Hz to about 100 Hz, or from about 1 Hz to about 10 Hz, but may not be limited thereto.

In accordance with an embodiment of the present disclosure, microbubbles generated from the porous pipe body may have an average diameter of from about 1 nm to about 1,000 μm, but may not be limited thereto. By way of example, the microbubbles may have an average diameter of from about 1 nm to about 1,000 μm, from about 10 nm to about 1,000 μm, from about 100 nm to about 1,000 μm, from about 300 nm to about 1,000 μm, from about 500 nm to about 1,000 μm, from about 700 nm to about 1,000 μm, from about 900 nm to about 1,000 μm, from about 1 μm to about 1,000 μm, from about 10 μm to about 1,000 μm, from about 100 μm to about 1,000 μm, from about 300 μm to about 1,000 μm, from about 500 μm to about 1,000 μm, from about 700 μm to about 1,000 μm, from about 900 μm to about 1,000 μm, from about 1 nm to about 900 μm, from about 10 nm to about 900 μm, from about 100 nm to about 900 μm, from about 300 nm to about 900 μm, from about 500 nm to about 900 μm, from about 700 nm to about 900 μm, from about 900 nm to about 900 μm, from about 1 μm to about 900 μm, from about 10 μm to about 900 μm, from about 100 μm to about 900 μm, from about 300 μm to about 900 μm, from about 500 μm to about 900 μm, from about 700 μm to about 900 μm, from about 1 nm to about 700 μm, from about 10 nm to about 700 μm, from about 100 nm to about 700 μm, from about 300 nm to about 700 μm, from about 500 nm to about 700 μm, from about 700 nm to about 700 μm, from about 900 nm to about 700 μm, from about 1 μm to about 700 μm, from about 10 μm to about 700 μm, from about 100 μm to about 700 μm, from about 300 μm to about 700 μm, from about 500 μm to about 700 μm, from about 1 nm to about 500 μm, from about 10 nm to about 500 μm, from about 100 nm to about 500 μm, from about 300 nm to about 500 μm, from about 500 nm to about 500 μm, from about 700 nm to about 500 μm, from about 900 nm to about 500 μm, from about 1 μm to about 500 μm, from about 10 μm to about 500 μm, from about 100 μm to about 500 μm, from about 300 μm to about 500 μm, from about 1 nm to about 300 μm, from about 10 nm to about 300 μm, from about 100 nm to about 300 µm, from about 300 nm to about 300 µm, from about 500 nm to about 300 µm, from about 700 nm to about 300 µm, from about 900 nm to about 300 µm, from about 1 µm to about 300 µm, from about 10 µm to about 300 µm, from about 100 µm to about 300 µm, from about 1 nm to about 100 µm, from about 10 nm to about 100 µm, from about 100 nm to about 100 µm, from about 300 nm to about 100 µm, from about 500 nm to about 100 µm, from about 700 nm to about 100 µm, from about 900 nm to about 100 µm, from about 1 µm to about 100 µm, from about 10 µm to about 100 µm, from about 1 nm to about 10 µm, from about 10 nm to about 10 µm, from about 100 nm to about 10 µm, from about 300 nm to about 10 µm, from about 500 nm to about 10 µm, from about 700 nm to about 10 µm, from about 900 nm to about 10 µm, from about 1 µm to about 10 µm, from about 1 nm to about 1 µm, from about 10 nm to about 1 µm, from about 100 nm to about 1 µm, from about 300 nm to about 1 µm, from about 500 nm to about 1 µm, from about 700 nm to about 1 µm, from about 900 nm to about 1 µm, from about 1 nm to about 900 nm, from about 10 nm to about 900 nm, from about 100 nm to about 900 nm, from about 300 nm to about 900 nm, from about 500 nm to about 900 nm, from about 700 nm to about 900 nm, from about 1 nm to about 700 nm, from about 10 nm to about 700 nm, from about 100 nm to about 700 nm, from about 300 nm to about 700 nm, from about 500 nm to about 700 nm, from about 1 nm to about 500 nm, from about 10 nm to about 500 nm, from about 100 nm to about 500 nm, from about 300 nm to about 500 nm, from about 1 nm to about 300 nm, from about 10 nm to about 300 nm, from about 100 nm to about 300 nm, from about 1 nm to about 100 nm, from about 10 nm to about 100 nm, or from about 1 nm to about 10 nm, but may not be limited thereto.

In a third aspect of the present disclosure, there is provided a cell culture medium including a serum and an antibiotic, and the cell culture medium contains microbubble water, and about 1 mL of the microbubble water contains from about $10^3$ to about $10^{18}$ of microbubbles having an average diameter of from about 1 nm to about 1,000 µm.

The microbubble water may be produced by a pressure dissolving type method, a swirling liquid flow type method, a static mixer type method, an ejector type method, a venturi type method, a fine pore type method, a rotating type method, a ultrasonic type method, a steam condensation type method, an electrolysis type method, and the like.

The microbubble water may contain microbubbles having an average diameter of from about 1 nm to about 1,000 µm, and about 1 mL of the microbubble water may contain from about $10^3$ to about $10^{18}$ of microbubbles, but may not be limited thereto. By way of example, the microbubbles contained in the microbubble water may have an average diameter of from about 1 nm to about 1,000 µm, from about 10 nm to about 1,000 µm, from about 100 nm to about 1,000 µm, from about 300 nm to about 1,000 µm, from about 500 nm to about 1,000 µm, from about 700 nm to about 1,000 µm, from about 900 nm to about 1,000 µm, from about 1 µm to about 1,000 µm, from about 10 µm to about 1,000 µm, from about 100 µm to about 1,000 µm, from about 300 µm to about 1,000 µm, from about 500 µm to about 1,000 µm, from about 700 µm to about 1,000 µm, from about 900 µm to about 1,000 µm, from about 1 nm to about 900 µm, from about 10 nm to about 900 µm, from about 100 nm to about 900 µm, from about 300 nm to about 900 µm, from about 500 nm to about 900 µm, from about 700 nm to about 900 µm, from about 900 nm to about 900 µm, from about 1 µm to about 900 µm, from about 10 µm to about 900 µm, from about 100 µm to about 900 µm, from about 300 µm to about 900 µm, from about 500 µm to about 900 µm, from about 700 µm to about 900 µm, from about 1 nm to about 700 µm, from about 10 nm to about 700 µm, from about 100 nm to about 700 µm, from about 300 nm to about 700 µm, from about 500 nm to about 700 µm, from about 700 nm to about 700 µm, from about 900 nm to about 700 µm, from about 1 µm to about 700 µm, from about 10 µm to about 700 µm, from about 100 µm to about 700 µm, from about 300 µm to about 700 µm, from about 500 µm to about 700 µm, from about 1 nm to about 500 µm, from about 10 nm to about 500 µm, from about 100 nm to about 500 µm, from about 300 nm to about 500 µm, from about 500 nm to about 500 µm, from about 700 nm to about 500 µm, from about 900 nm to about 500 µm, from about 1 µm to about 500 µm, from about 10 µm to about 500 µm, from about 100 µm to about 500 µm, from about 300 µm to about 500 µm, from about 1 nm to about 300 µm, from about 10 nm to about 300 µm, from about 100 nm to about 300 µm, from about 300 nm to about 300 µm, from about 500 nm to about 300 µm, from about 700 nm to about 300 µm, from about 900 nm to about 300 µm, from about 1 µm to about 300 µm, from about 10 µm to about 300 µm, from about 100 µm to about 300 µm, from about 1 nm to about 100 µm, from about 10 nm to about 100 µm, from about 100 nm to about 100 µm, from about 300 nm to about 100 µm, from about 500 nm to about 100 µm, from about 700 nm to about 100 µm, from about 900 nm to about 100 µm, from about 1 µm to about 100 µm, from about 10 µm to about 100 µm, from about 1 nm to about 10 µm, from about 10 nm to about 10 µm, from about 100 nm to about 10 µm, from about 300 nm to about 10 µm, from about 500 nm to about 10 µm, from about 700 nm to about 10 µm, from about 900 nm to about 10 µm, from about 1 µm to about 10 µm, from about 1 nm to about 1 µm, from about 10 nm to about 1 µm, from about 100 nm to about 1 µm, from about 300 nm to about 1 µm, from about 500 nm to about 1 µm, from about 700 nm to about 1 µm, from about 900 nm to about 1 µm, from about 1 nm to about 900 nm, from about 10 nm to about 900 nm, from about 100 nm to about 900 nm, from about 300 nm to about 900 nm, from about 500 nm to about 900 nm, from about 700 nm to about 900 nm, from about 1 nm to about 700 nm, from about 10 nm to about 700 nm, from about 100 nm to about 700 nm, from about 300 nm to about 700 nm, from about 500 nm to about 700 nm, from about 1 nm to about 500 nm, from about 10 nm to about 500 nm, from about 100 nm to about 500 nm, from about 300 nm to about 500 nm, from about 1 nm to about 300 nm, from about 10 nm to about 300 nm, from about 100 nm to about 300 nm, from about 1 nm to about 100 nm, from about 10 nm to about 100 nm, or from about 1 nm to about 10 nm, but may not be limited thereto. By way of example, 1 mL of the microbubble water may contain from about $10^3$ to about $10^{18}$, from about $10^4$ to about $10^{18}$, from about $10^5$ to about $10^{18}$, from about $10^6$ to about $10^{18}$, from about $10^7$ to about $10^{18}$, from about $10^8$ to about $10^{18}$, from about $10^9$ to about $10^{18}$, from about $10^{10}$ to about $10^{18}$, from about $10^{11}$ to about $10^{18}$, from about $10^{12}$ to about $10^{18}$, from about $10^{13}$ to about $10^{18}$, from about $10^{14}$ to about $10^{18}$, from about $10^{15}$ to about $10^{18}$, from about $10^{16}$ to about $10^{18}$, from about $10^{17}$ to about $10^{18}$, from about $10^3$ to about $10^{17}$, from about $10^4$ to about $10^{17}$, from about $10^5$ to about $10^{17}$, from about $10^6$ to about $10^{17}$, from about $10^7$ to about $10^{17}$, from about $10^8$ to about $10^{17}$, from about $10^9$ to about $10^{17}$, from about $10^{10}$ to about $10^{17}$, from about $10^{11}$ to about $10^{17}$, from about $10^{12}$ to about $10^{17}$, from about $10^{13}$ to about $10^{17}$, from about $10^{14}$ to about $10^{17}$, from about $10^{15}$ to about $10^{17}$, from about $10^{16}$ to about $10^{17}$, from about $10^3$ to about $10^{16}$, from about $10^4$ to about $10^{16}$, from about $10^5$ to about $10^{16}$, from about $10^6$ to about $10^{16}$, from about $10^7$ to about $10^{16}$, from about $10^8$ to about $10^{16}$, from about $10^9$ to about $10^{16}$, from about $10^{10}$ to about $10^{16}$, from about $10^{11}$ to about $10^{16}$, from about $10^{12}$ to about $10^{16}$, from about $10^{13}$ to about $10^{16}$, from about $10^{14}$ to about $10^{16}$, from about $10^{15}$ to about $10^{16}$, from about $10^3$ to about $10^{15}$, from about $10^4$ to about $10^{15}$, from about $10^5$ to about $10^{15}$, from about $10^6$ to about $10^{15}$, from about $10^7$ to about $10^{15}$, from about $10^8$ to about $10^{15}$, from about $10^9$ to about $10^{15}$, from about $10^{10}$ to about $10^{15}$, from about $10^{11}$ to about $10^{15}$, from about $10^{12}$ to about $10^{15}$, from about $10^{13}$ to about $10^{15}$, from about $10^{14}$ to about $10^{15}$, from about $10^3$ to about $10^{14}$, from about $10^4$ to about $10^{14}$, from about $10^5$ to about $10^{14}$, from about $10^6$ to about $10^{14}$, from about $10^7$ to about $10^{14}$, from about $10^8$ to about $10^{14}$, from about $10^9$ to about $10^{14}$, from about $10^{10}$ to about $10^{14}$, from about $10^{11}$ to about $10^{14}$, from about $10^{12}$ to about $10^{14}$, from about $10^{13}$ to about $10^{14}$, from about $10^3$ to about $10^{13}$, from about $10^4$ to about $10^{13}$, from about $10^5$ to about $10^{13}$, from about $10^6$ to about $10^{13}$, from about $10^7$ to about $10^{13}$, from about $10^8$ to about $10^{13}$, from about $10^9$ to about $10^{13}$, from about $10^{10}$ to about $10^{13}$, from about $10^{11}$ to about $10^{13}$, from about $10^{12}$ to about $10^{13}$, from about $10^3$ to about $10^{12}$, from about $10^4$ to about $10^{12}$, from about $10^5$ to about $10^{12}$, from about $10^6$ to about $10^{12}$, from about $10^7$ to about $10^{12}$, from about $10^8$ to about $10^{12}$, from about $10^9$ to about $10^{12}$, from about $10^{10}$ to about $10^{12}$, from about $10^{11}$ to about $10^{12}$, from about $10^3$ to about $10^{11}$, from about $10^4$ to about $10^{11}$, from about $10^5$ to about $10^{11}$, from about $10^6$ to about $10^{11}$, from about $10^7$ to about $10^{11}$, from about $10^8$ to about $10^{11}$, from about $10^9$ to about $10^{11}$, from about $10^{10}$ to about $10^{11}$, from about $10^3$ to about $10^{10}$, from about $10^4$ to about $10^{10}$, from about $10^5$ to about $10^{10}$, from about $10^6$ to about $10^{10}$, from about $10^7$ to about $10^{10}$, from about $10^8$ to about $10^{10}$, from about $10^9$ to about $10^{10}$, from about $10^3$ to about $10^9$, from about $10^4$ to about $10^9$, from about $10^5$ to about $10^9$, from about $10^6$ to about $10^9$, from about $10^7$ to about $10^9$, from about $10^8$ to about $10^9$, from about $10^3$ to about $10^8$, from about $10^4$ to about $10^8$, from about $10^5$ to about $10^8$, from about $10^6$ to about $10^8$, from about $10^7$ to about $10^8$, from about $10^3$ to about $10^7$, from about $10^4$ to about $10^7$, from about $10^5$ to about $10^7$, from about $10^6$ to about $10^7$, from about $10^3$ to about $10^6$, from about $10^4$ to about $10^6$, from about $10^5$ to about $10^6$, from about $10^3$ to about $10^5$, from about $10^4$ to about $10^5$, or from about $10^3$ to about $10^4$ of microbubbles, but may not be limited thereto. The microbubbles may be present in water for a long time since the microbubbles are stabilized due to a self-pressurization effect of the microbubbles. However, if the microbubbles have an average diameter greater than the above-describe range, a time for the microbubbles to be present in water is reduced due to a buoyancy effect of the bubbles, resulting in a reduction in the amount of dissolved microbubbles in water. Further, if the number of the microbubbles per about 1 mL of the microbubble water is out of the above-described range and less than about $10^3$, there may be problems with the solubility with respect to water, a sterilizing action and a surface activity action of the microbubbles, the uniformity in number of uniform microbubbles in microbubble water due to the dissipated number of microbubbles caused by the self-pressurization effect of the microbubbles.

In accordance with an embodiment of the present disclosure, the microbubble water may be contained from about 1 part by volume to about 50 parts by volume, desirably from about 1 part by volume to about 20 parts by volume, with respect to total 100 parts by volume of the cell culture medium, but may not be limited thereto. By way of example, if the microbubble water is contained less than about 1 part by volume, the number of microbubbles required for cell growth may be reduced. If the microbubble water is contained more than about 50 parts by volume, a reduction in cell growth may be caused by a reduction in nutrient of the cell culture medium for cell growth.

In accordance with an embodiment of the present disclosure, the microbubble water may be applied with various gases depending on a function thereof, and for example, the microbubble water may include a gas selected from the group consisting of hydrogen, oxygen, carbon dioxide, carbon monoxide, nitrogen, xenon, argon, neon, air, ozone, krypton, helium, a nitrogen-containing compound gas, a carbon-containing compound gas, and combinations thereof, but may not be limited thereto. The microbubble water may include the gas, but may not be limited thereto.

In accordance with an embodiment of the present disclosure, the cell to which the culture medium can be applied may include a member selected from a cancer cell selected from the group consisting of a lung cancer call, a prostate cancer cell, a stomach cancer cell, a breast cancer cell, a pancreatic cancer cell, a colorectal cancer cell, and combinations thereof; a cell selected from the group consisting of an osteoblast, a kidney cell, a fibroblast, a cartilage cell, a liver cell, a nerve cell, a muscular cell, a stem cell, and combinations thereof, but may not be limited thereto.

In accordance with an embodiment of the present disclosure, the serum may include a member selected from the group consisting of a fetal bovine serum (FBS), a fetal calf serum (FCS), and combinations thereof, but may not be limited thereto.

In a fourth aspect of the present disclosure, there is provided a cell culturing method including: culturing a cell in a culture medium in a confluent manner; and replacing the cell culture medium with a culture medium including microbubble water, and about 1 mL of the microbubble water contains from about $10^3$ to about $10^{18}$ of microbubbles having an average diameter of from about 1 nm to about 1,000 μm.

In accordance with an embodiment of the present disclosure, the microbubble water may be contained from about 1 part by volume to about 50 parts by volume, desirably from about 1 part by volume to about 20 parts by volume with respect to total 100 parts by volume of the cell culture medium, and the microbubble water may be sterilized under UV light before being added to the cell culture medium, but may not be limited thereto.

In accordance with an embodiment of the present disclosure, the cell may include a member selected from a cancer cell selected from the group consisting of a lung cancer call, a prostate cancer cell, a stomach cancer cell, a breast cancer cell, a pancreatic cancer cell, a colorectal cancer cell, and combinations thereof; a cell selected from the group an osteoblast, a kidney cell, a fibroblast, a cartilage cell, a liver cell, a nerve cell, a muscular cell, a stem cell, and combinations thereof, but may not be limited thereto.

In accordance with an embodiment of the present disclosure, the serum may include a member selected from the group consisting of a fetal bovine serum (FBS), a fetal calf serum (FCS), and combinations thereof, but may not be limited thereto.

In an example of the present disclosure, as illustrated in FIG. 6 to FIG. 15, according to the result of culturing each of lung cancer cells A549 and A549D9K, osteoblast MC3T3, fibroblast NIH3T3, and kidney cell HEK293 by using a cell culture medium containing microbubble water, it was confirmed that cell growth was promoted, as compared with a control group in which a cell was cultured by using a medium which does not contain microbubble water.

Figure 16:
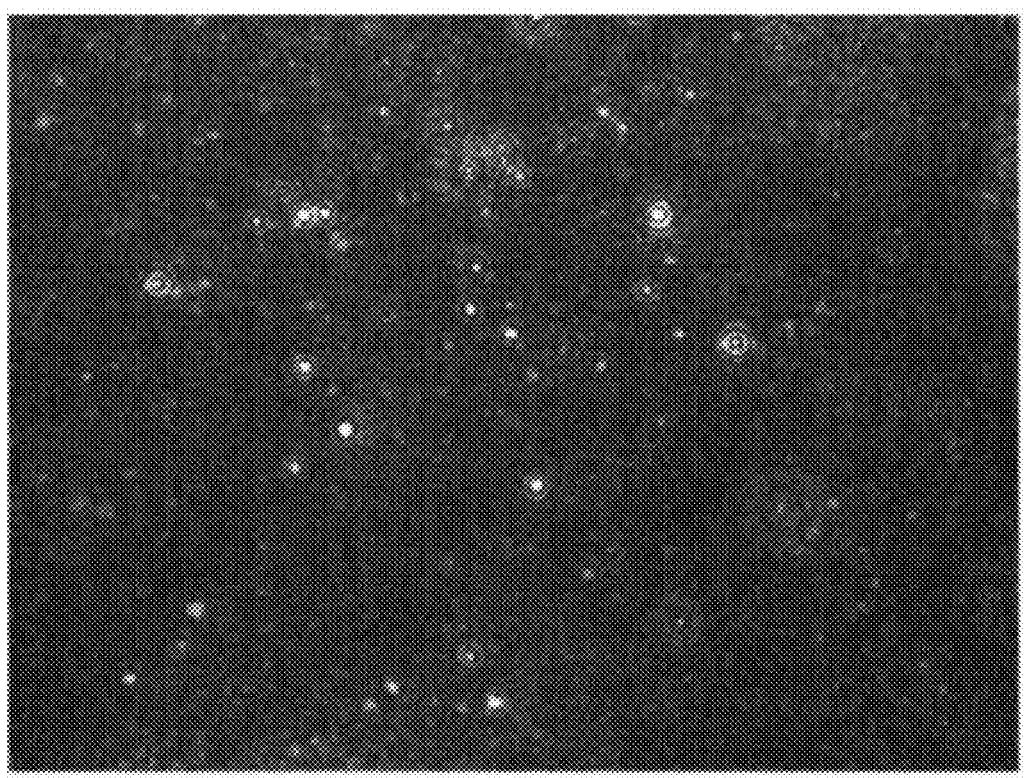
FIG. 16 is an image of microbubbles captured by using a NanoSight LM10-HS, a high-sensitivity CCD (charge coupled device) camera including an LM14 equipped with a 405 nm laser, and an ×20 microscope objective lens 121 days after the microbubbles are generated in gasoline in accordance with an example of the present disclosure.

In a fifth aspect of the present disclosure, there is provided a high-efficiency mixed fuel including: a fuel; and microbubbles formed in the fuel. In this regard, FIG. 16 is an image of microbubbles captured by using a NanoSight LM10-HS, a high-sensitivity CCD (charge coupled device) camera including an LM14 equipped with a 405 nm laser, and an ×20 microscope objective lens after the microbubbles are generated in the fuel, and specifically, an image of a high-efficiency mixed fuel produced in accordance with an example of the present disclosure. In accordance with an embodiment of the present disclosure, the fuel may include a member selected from the group consisting of fossil fuels, bio fuels, and combinations thereof, but may not be limited thereto. By way of example, the fossil fuel may include a member selected from the group consisting of gasoline, diesel, lubricating oil, bunker oil, and combinations thereof, but may not be limited thereto. By way of example, the bio fuel may include a member selected from the group consisting of bio ethanol, bio methanol, bio diesel, and combinations thereof, but may not be limited thereto. By way of example, the gasoline refers to liquid state of petroleum fractions having volatility, and may need to have a high calorific value, a high flowability, a high velocity of combustion, and a high self-ignition temperature, and less generation of harmful compounds after combustion, but may not be limited thereto. By way of example, the diesel may need to have an excellent ignitionability caused by a high cetane number, no impurity, and a high calorific value, but may not be limited thereto. The cetane number refers to a quantitative value of ignitionability of diesel. As the cetane number increases, it may be difficult to cause a diesel knock phenomenon, but may not be limited thereto. The microbubble is a very small cavity formed in a liquid and filled with a gas. If the microbubbles are used as a fuel, generation of gases, such as carbon monoxide, carbon dioxide, and nitrogen compounds, that cause a greenhouse effect can be remarkably reduced, and also, they can be easily transported in the form of a gas or a liquid and thus suitable for mass storage. By way of example, the gas may include a gas selected from the group consisting of hydrogen, oxygen, carbon dioxide, carbon monoxide, nitrogen, xenon, argon, neon, air, ozone, krypton, helium, a nitrogen-containing compound gas, a carbon-containing compound gas, and combinations thereof, but may not be limited thereto. By way of example, if hydrogen is used as the gas, the hydrogen can be prepared using water as a source and can be recycled as water after use, and thus, has many advantages in terms of efficiency, but may not be limited thereto.

FIG. 17A to FIG. 17D show concentrations and diameters of the microbubbles formed in the fuel. By way of example, the concentration of the microbubbles may increase depending on time due to self-dissociation of the formed microbubbles, as can be seen from FIG. 17A. By way of example, about 1 mL of the fuel may include from about $10^3$ to about $10^{18}$ of microbubbles, but may not be limited thereto. By way of example, about 1 mL of the fuel may include from about $10^3$ to about $10^{18}$, from about $10^4$ to about $10^{18}$, from about $10^5$ to about $10^{18}$, from about $10^6$ to about $10^{18}$, from about $10^7$ to about $10^{18}$, from about $10^8$ to about $10^{18}$, from about $10^9$ to about $10^{18}$, from about $10^{10}$ to about $10^{18}$, from about $10^{11}$ to about $10^{18}$, from about $10^{12}$ to about $10^{18}$, from about $10^{13}$ to about $10^{18}$, from about $10^{14}$ to about $10^{18}$, from about $10^{15}$ to about $10^{18}$, from about $10^{16}$ to about $10^{18}$, from about $10^{17}$ to about $10^{18}$, from about $10^3$ to about $10^{17}$, from about $10^4$ to about $10^{17}$, from about $10^5$ to about $10^{17}$, from about $10^6$ to about $10^{17}$, from about $10^7$ to about $10^{17}$, from about $10^8$ to about $10^{17}$, from about $10^9$ to about $10^{17}$, from about $10^{10}$ to about $10^{17}$, from about $10^{11}$ to about $10^{17}$, from about $10^{12}$ to about $10^{17}$, from about $10^{13}$ to about $10^{17}$, from about $10^{14}$ to about $10^{17}$, from about $10^{15}$ to about $10^{17}$, from about $10^{16}$ to about $10^{17}$, from about $10^3$ to about $10^{16}$, from about $10^4$ to about $10^{16}$, from about $10^5$ to about $10^{16}$, from about $10^6$ to about $10^{16}$, from about $10^7$ to about $10^{16}$, from about $10^8$ to about $10^{16}$, from about $10^9$ to about $10^{16}$, from about $10^{10}$ to about $10^{16}$, from about $10^{11}$ to about $10^{16}$, from about $10^{12}$ to about $10^{16}$, from about $10^{13}$ to about $10^{16}$, from about $10^{14}$ to about $10^{16}$, from about $10^{15}$ to about $10^{16}$, from about $10^3$ to about $10^{15}$, from about $10^4$ to about $10^{15}$, from about $10^5$ to about $10^{15}$, from about $10^6$ to about $10^{15}$, from about $10^7$ to about $10^{15}$, from about $10^8$ to about $10^{15}$, from about $10^9$ to about $10^{15}$, from about $10^{10}$ to about $10^{15}$, from about $10^{11}$ to about $10^{15}$, from about $10^{12}$ to about $10^{15}$, from about $10^{13}$ to about $10^{15}$, from about $10^{14}$ to about $10^{15}$, from about $10^3$ to about $10^{14}$, from about $10^4$ to about $10^{14}$, from about $10^5$ to about $10^{14}$, from about $10^6$ to about $10^{14}$, from about $10^7$ to about $10^{14}$, from about $10^8$ to about $10^{14}$, from about $10^9$ to about $10^{14}$, from about $10^{10}$ to about $10^{14}$, from about $10^{11}$ to about $10^{14}$, from about $10^{12}$ to about $10^{14}$, from about $10^{13}$ to about $10^{14}$, from about $10^3$ to about $10^{13}$, from about $10^4$ to about $10^{13}$, from about $10^5$ to about $10^{13}$, from about $10^6$ to about $10^{13}$, from about $10^7$ to about $10^{13}$, from about $10^8$ to about $10^{13}$, from about $10^9$ to about $10^{13}$, from about $10^{10}$ to about $10^{13}$, from about $10^{11}$ to about $10^{13}$, from about $10^{12}$ to about $10^{13}$, from about $10^3$ to about $10^{12}$, from about $10^4$ to about $10^{12}$, from about $10^5$ to about $10^{12}$, from about $10^6$ to about $10^{12}$, from about $10^7$ to about $10^{12}$, from about $10^8$ to about $10^{12}$, from about $10^9$ to about $10^{12}$, from about $10^{10}$ to about $10^{12}$, from about $10^{11}$ to about $10^{12}$, from about $10^3$ to about $10^{11}$, from about $10^4$ to about $10^{11}$, from about $10^5$ to about $10^{11}$, from about $10^6$ to about $10^{11}$, from about $10^7$ to about $10^{11}$, from about $10^8$ to about $10^{11}$, from about $10^9$ to about $10^{11}$, from about $10^{10}$ to about $10^{11}$, from about $10^3$ to about $10^{10}$, from about $10^4$ to about $10^{10}$, from about $10^5$ to about $10^{10}$, from about $10^6$ to about $10^{10}$, from about $10^7$ to about $10^{10}$, from about $10^8$ to about $10^{10}$, from about $10^9$ to about $10^{10}$, from about $10^3$ to about $10^9$, from about $10^4$ to about $10^9$, from about $10^5$ to about $10^9$, from about $10^6$ to about $10^9$, from about $10^7$ to about $10^9$, from about $10^8$ to about $10^9$, from about $10^3$ to about $10^8$, from about $10^4$ to about $10^8$, from about $10^5$ to about $10^8$, from about $10^6$ to about $10^8$, from about $10^7$ to about $10^8$, from about $10^3$ to about $10^7$, from about $10^4$ to about $10^7$, from about $10^5$ to about $10^7$, from about $10^6$ to about $10^7$, from about $10^3$ to about $10^6$, from about $10^4$ to about $10^6$, from about $10^5$ to about $10^6$, from about $10^3$ to about $10^5$, from about $10^4$ to about $10^5$, or from about $10^3$ to about $10^4$ of microbubbles, but may not be limited thereto.

Figure 17A:
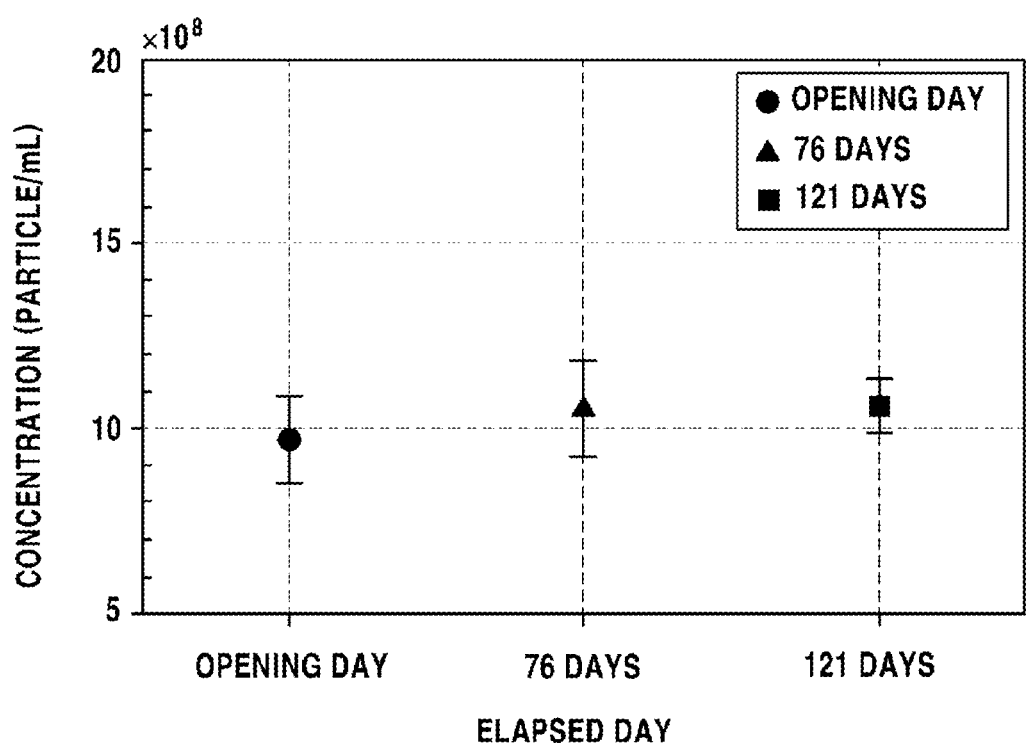
FIG. 17A shows a change in number of microbubbles in gasoline with time in accordance with an example of the present disclosure.
Figure 17B:
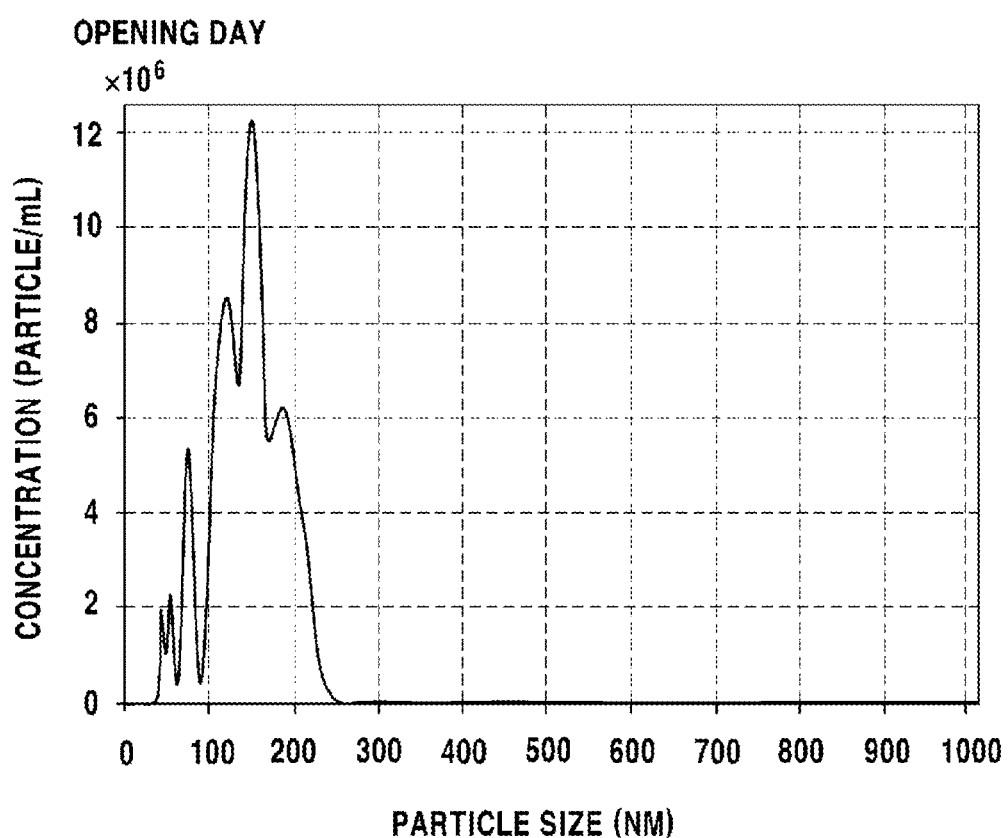
FIG. 17B to FIG. 17D show the size distributions of microbubbles right after the microbubbles are generated in gasoline, after 76 days, and after 121 days, respectively.
Figure 17C:
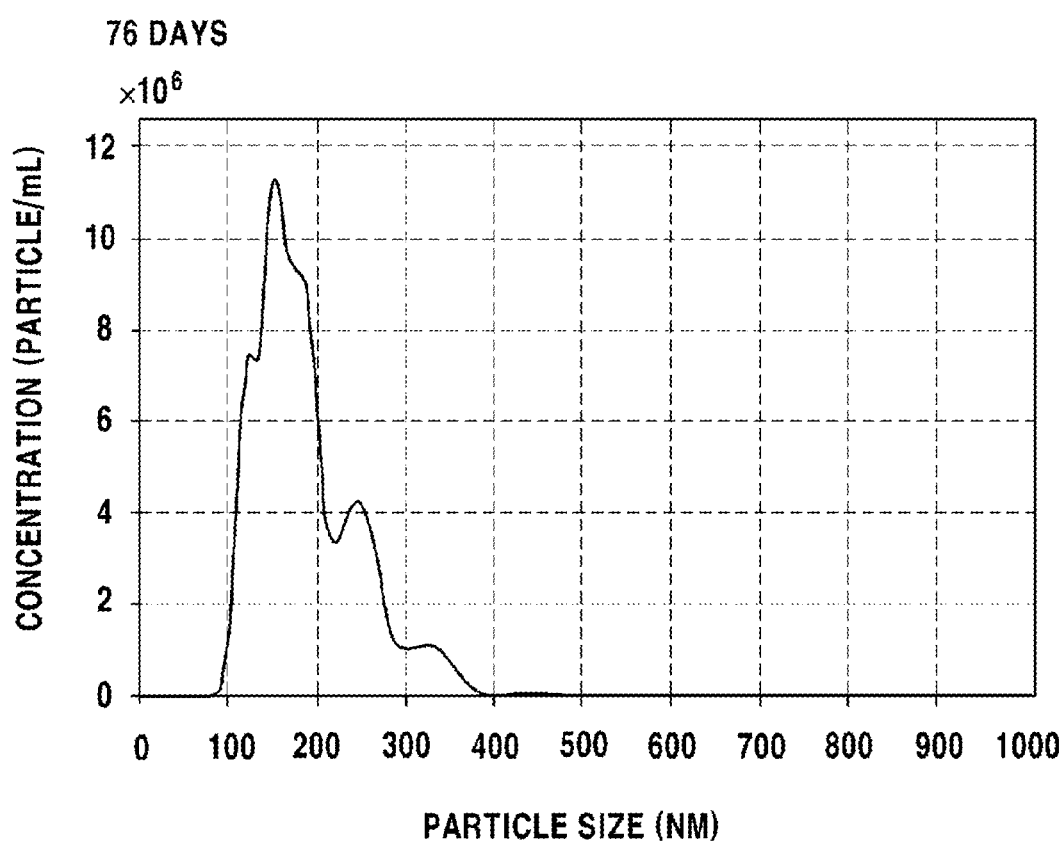
Figure 17D:
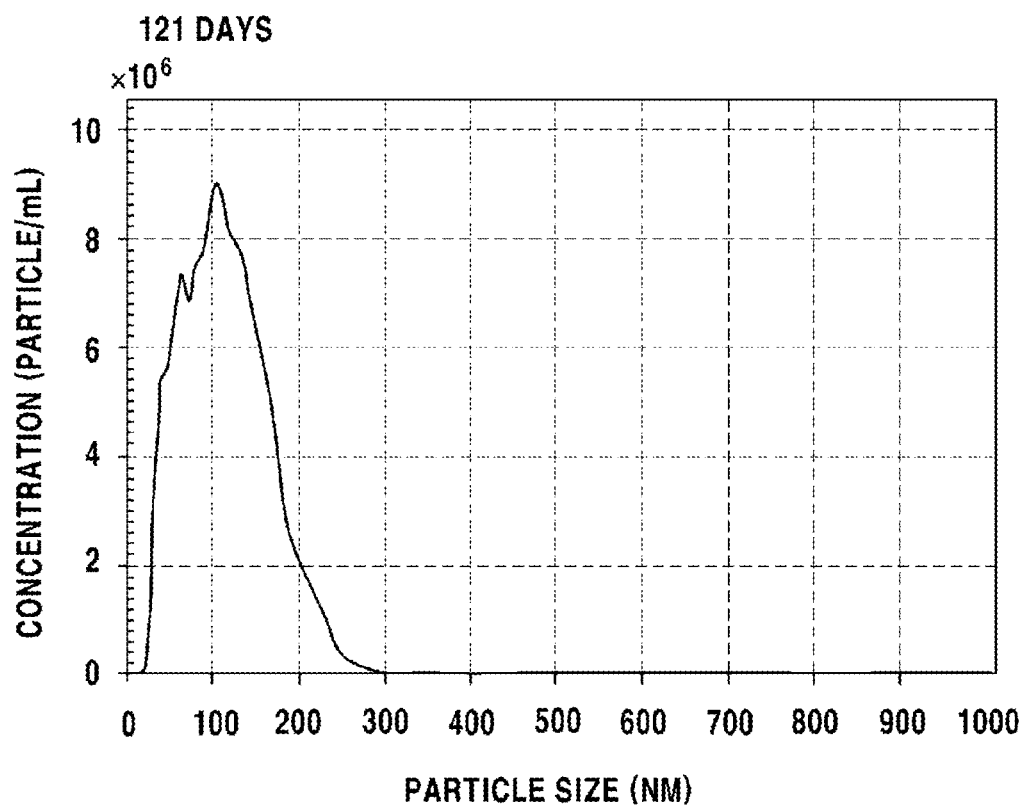

Then, referring to FIG. 17B to FIG. 17D, although the microbubbles do not have a uniform diameter distribution right after formation thereof, the microbubbles become uniform in diameter depending on time, but may not be limited thereto. By way of example, the microbubbles may have a diameter of from about 1 nm to about 1,000 μm, but may not be limited thereto. By way of example, the microbubbles may have a diameter of from about 1 nm to about 1,000 μm, from about 10 nm to about 1,000 μm, from about 100 nm to about 1,000 μm, from about 300 nm to about 1,000 μm, from about 500 nm to about 1,000 μm, from about 700 nm to about 1,000 μm, from about 900 nm to about 1,000 μm, from about 1 μm to about 1,000 μm, from about 10 μm to about 1,000 μm, from about 100 μm to about 1,000 μm, from about 300 μm to about 1,000 μm, from about 500 μm to about 1,000 μm, from about 700 μm to about 1,000 μm, from about 900 μm to about 1,000 μm, from about 1 nm to about 900 μm, from about 10 nm to about 900 μm, from about 100 nm to about 900 μm, from about 300 nm to about 900 μm, from about 500 nm to about 900 μm, from about 700 nm to about 900 μm, from about 900 nm to about 900 μm, from about 1 μm to about 900 μm, from about 10 μm to about 900 μm, from about 100 μm to about 900 μm, from about 300 μm to about 900 μm, from about 500 μm to about 900 μm, from about 700 μm to about 900 μm, from about 1 nm to about 700 μm, from about 10 nm to about 700 μm, from about 100 nm to about 700 μm, from about 300 nm to about 700 μm, from about 500 nm to about 700 μm, from about 700 nm to about 700 μm, from about 900 nm to about 700 μm, from about 1 μm to about 700 μm, from about 10 μm to about 700 μm, from about 100 μm to about 700 μm, from about 300 μm to about 700 μm, from about 500 μm to about 700 μm, from about 1 nm to about 500 μm, from about 10 nm to about 500 μm, from about 100 nm to about 500 μm, from about 300 nm to about 500 μm, from about 500 nm to about 500 μm, from about 700 nm to about 500 μm, from about 900 nm to about 500 μm, from about 1 μm to about 500 μm, from about 10 μm to about 500 μm, from about 100 μm to about 500 μm, from about 300 μm to about 500 μm, from about 1 nm to about 300 μm, from about 10 nm to about 300 μm, from about 100 nm to about 300 μm, from about 300 nm to about 300 μm, from about 500 nm to about 300 μm, from about 700 nm to about 300 μm, from about 900 nm to about 300 μm, from about 1 μm to about 300 μm, from about 10 μm to about 300 μm, from about 100 μm to about 300 μm, from about 1 nm to about 100 μm, from about 10 nm to about 100 μm, from about 100 nm to about 100 μm, from about 300 nm to about 100 μm, from about 500 nm to about 100 μm, from about 700 nm to about 100 μm, from about 900 nm to about 100 μm, from about 1 μm to about 100 μm, from about 10 μm to about 100 μm, from about 1 nm to about 10 μm, from about 10 nm to about 10 μm, from about 100 nm to about 10 μm, from about 300 nm to about 10 μm, from about 500 nm to about 10 μm, from about 700 nm to about 10 μm, from about 900 nm to about 10 μm, from about 1 μm to about 10 μm, from about 1 nm to about 1 μm, from about 10 nm to about 1 μm, from about 100 nm to about 1 μm, from about 300 nm to about 1 μm, from about 500 nm to about 1 μm, from about 700 nm to about 1 μm, from about 900 nm to about 1 μm, from about 1 nm to about 900 nm, from about 10 nm to about 900 nm, from about 100 nm to about 900 nm, from about 300 nm to about 900 nm, from about 500 nm to about 900 nm, from about 700 nm to about 900 nm, from about 1 nm to about 700 nm, from about 10 nm to about 700 nm, from about 100 nm to about 700 nm, from about 300 nm to about 700 nm, from about 500 nm to about 700 nm, from about 1 nm to about 500 nm, from about 10 nm to about 500 nm, from about 100 nm to about 500 nm, from about 300 nm to about 500 nm, from about 1 nm to about 300 nm, from about 10 nm to about 300 nm, from about 100 nm to about 300 nm, from about 1 nm to about 100 nm, from about 10 nm to about 100 nm, or from about 1 nm to about 10 nm, but may not be limited thereto.

Figure 18A:
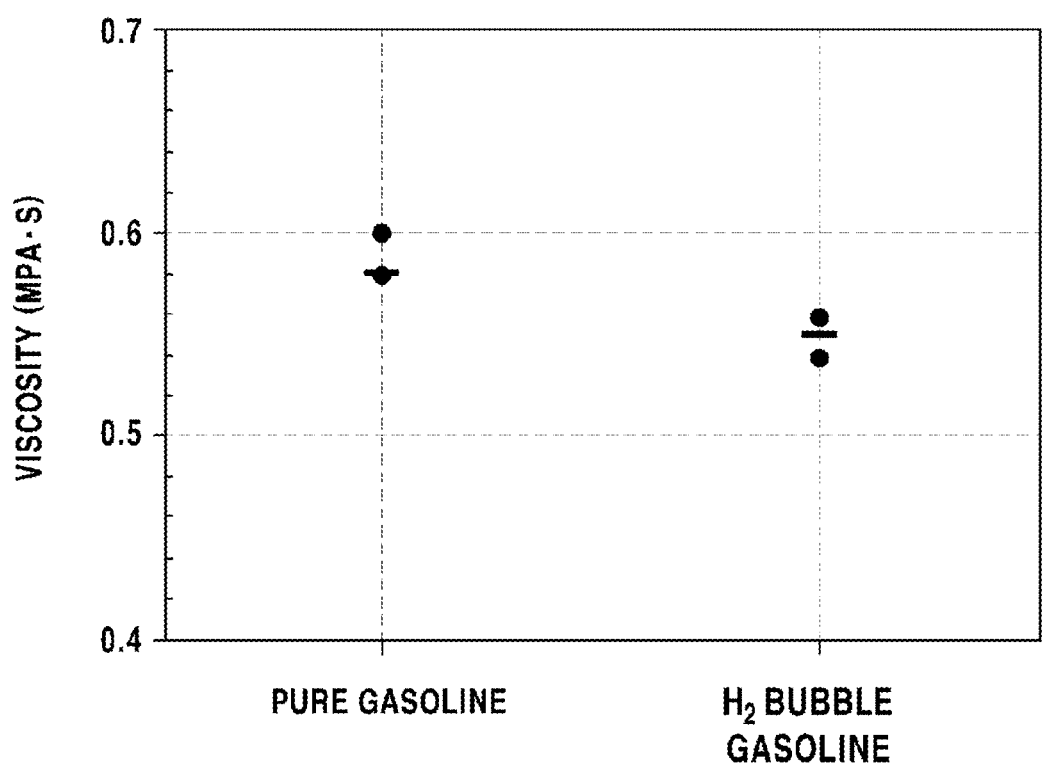
FIG. 18A shows the viscosities of the conventional gasoline and the gasoline in which microbubbles are generated in accordance with an example of the present disclosure.

FIG. 18A shows the viscosity of the fuel, and shows the viscosities of the conventional gasoline and the gasoline in which microbubbles are generated. The gasoline in which microbubbles are generated may have a viscosity of from about 0.4 MPa·s to about 0.7 MPa·s, but may not be limited thereto. By way of example, the gasoline in which microbubbles are generated may have a viscosity of from about 0.4 MPa·s to about 0.7 MPa·s, from about 0.45 MPa·s to about 0.7 MPa·s, from about 0.5 MPa·s to about 0.7 MPa·s, from about 0.55 MPa·s to about 0.7 MPa·s, from about 0.6 MPa·s to about 0.7 MPa·s, from about 0.65 MPa·s to about 0.7 MPa·s, from about 0.4 MPa·s to about 0.65 MPa·s, from about 0.45 MPa·s to about 0.65 MPa·s, from about 0.5 MPa·s to about 0.65 MPa·s, from about 0.55 MPa·s to about 0.65 MPa·s, from about 0.6 MPa·s to about 0.65 MPa·s, from about 0.4 MPa·s to about 0.6 MPa·s, from about 0.45 MPa·s to about 0.6 MPa·s, from about 0.5 MPa·s to about 0.6 MPa·s, from about 0.55 MPa·s to about 0.6 MPa·s, from about 0.4 MPa·s to about 0.55 MPa·s, from about 0.45 MPa·s to about 0.55 MPa·s, from about 0.5 MPa·s to about 0.55 MPa·s, from about 0.4 MPa·s to about 0.5 MPa·s, from about 0.45 MPa·s to about 0.5 MPa·s, or from about 0.4 MPa·s to about 0.45 MPa·s, but may not be limited thereto. The viscosity of the fuel refers to an internal resistance generated when the fuel flows. When the viscosity of the fuel is high, an injection characteristic of the fuel deteriorates, and thus, it is necessary to increase an injection pressure when the fuel is injected, and also, engine performance and a combustion characteristic of the fuel may deteriorate, but may not be limited thereto.

Figure 18B:
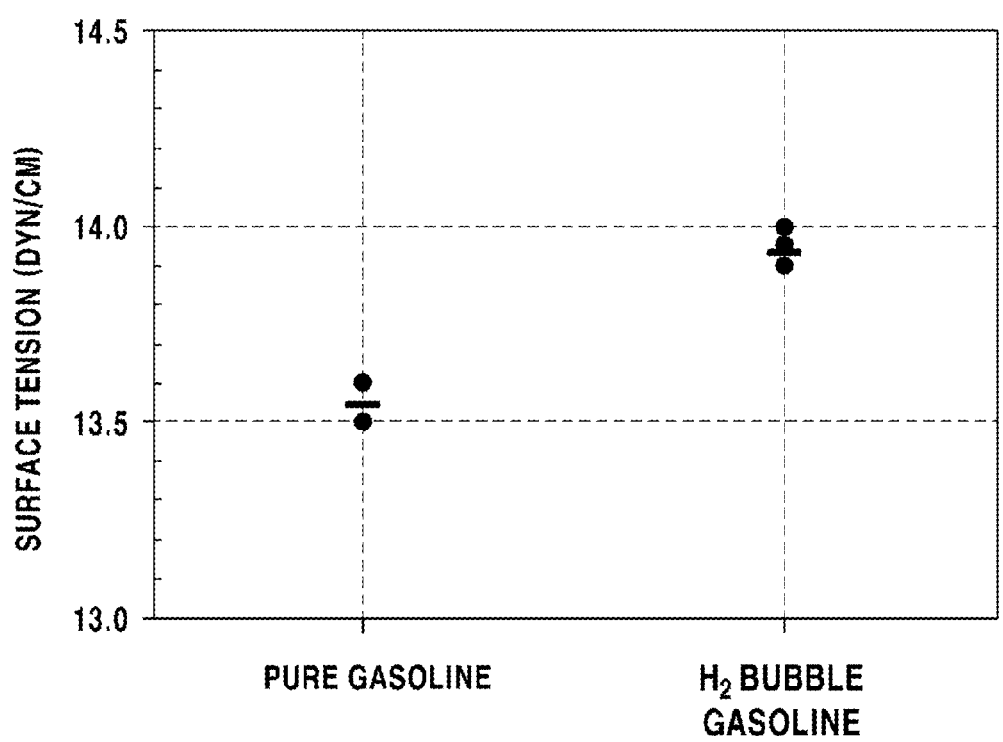
FIG. 18B shows the surface tensions of the conventional gasoline and the gasoline in which microbubbles are generated in accordance with an example of the present disclosure.

Meanwhile, FIG. 18B shows the surface tension of the fuel, and shows the surface tension of the conventional gasoline and the gasoline in which microbubbles are generated. The gasoline in which microbubbles are generated may have a surface tension of from about 12 dyn/cm to about 15 dyn/cm, but may not be limited thereto. By way of example, the gasoline in which microbubbles are generated may have a surface tension of from about 12 dyn/cm to about 15 dyn/cm, from about 12.5 dyn/cm to about 15 dyn/cm, from about 13 dyn/cm to about 15 dyn/cm, from about 13.5 dyn/cm to about 15 dyn/cm, from about 14 dyn/cm to about 15 dyn/cm, from about 14.5 dyn/cm to about 15 dyn/cm, from about 12 dyn/cm to about 14.5 dyn/cm, from about 12.5 dyn/cm to about 14.5 dyn/cm, from about 13 dyn/cm to about 14.5 dyn/cm, from about 13.5 dyn/cm to about 14.5 dyn/cm, from about 14 dyn/cm to about 14.5 dyn/cm, from about 12 dyn/cm to about 14 dyn/cm, from about 12.5 dyn/cm to about 14 dyn/cm, from about 13 dyn/cm to about 14 dyn/cm, from about 13.5 dyn/cm to about 14 dyn/cm, from about 12 dyn/cm to about 13.5 dyn/cm, from about 12.5 dyn/cm to about 13.5 dyn/cm, from about 13 dyn/cm to about 13.5 dyn/cm, from about 12 dyn/cm to about 13 dyn/cm, from about 12.5 dyn/cm to about 13 dyn/cm, or from about 12 dyn/cm to about 12.5 dyn/cm, but may not be limited thereto. The surface tension of the fuel refers to a force applied from the fuel to the surrounding molecules to minimize a surface which the fuel occupies. By regulating the surface tension, the fuel may smoothly flow, but may not be limited thereto.

In a sixth aspect of the present disclosure, there is provided an apparatus for manufacturing a high-efficiency mixed fuel, including: a liquid tank into which a liquid is injected; a gas supply line unit configured to supply a gas into the liquid tank; and a porous pipe body provided in the liquid tank.

Figure 19:
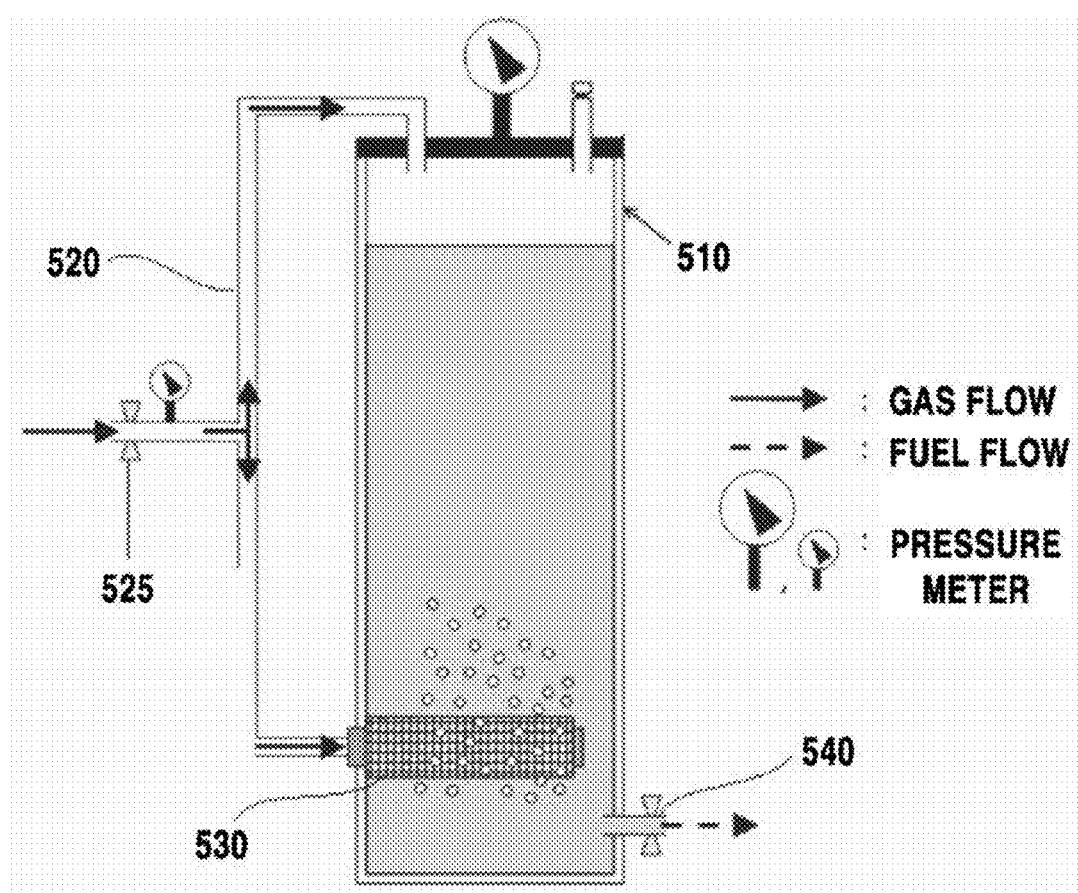
FIG. 19 is a configuration view showing an apparatus for manufacturing a high-efficiency mixed fuel using microbubbles in accordance with an embodiment of the present disclosure.

FIG. 19 shows an apparatus for manufacturing a high-efficiency mixed fuel using microbubbles in accordance with an embodiment of the present disclosure. Firstly, a liquid tank 510 into which a liquid is injected is prepared. Like a typical liquid tank, the liquid tank 510 may have a structure into which a predetermined liquid is injected and of which the injected liquid does not leak out, but may not be limited thereto. An upper part of the liquid tank 510 may be sealed by a sealing lid, but may not be limited thereto. The sealing lid may include a gas supply line unit connected to the sealing lid, a pressure gauge provided at the sealing lid and configured to check a pressure within the liquid tank 510, and a pressure control valve configured to control a pressure within the liquid tank 510, but may not be limited thereto. By way of example, the liquid may include a member selected from the group consisting of water, high-viscosity materials, and combinations thereof, but may not be limited thereto. By way of example, the high-viscosity material may include a member selected from the group consisting of polymers, fuels, and combinations thereof, but may not be limited thereto. By way of example, the high-viscosity material may include a member selected from the group consisting of polymers, fossil fuels, bio fuels, and combinations thereof, and may include, for example, a member selected from the group consisting of lubricating oil, gasoline, diesel, bunker oil, bio ethanol, bio methanol, bio diesel, and combinations thereof, but may not be limited thereto.

In accordance with an embodiment of the present disclosure, the gas supply line unit may include an inlet valve 525 through which a gas is injected, a pressure gauge configured to measure a pressure of the injected gas, and a supply pipe 520 through which the injected gas moves, but may not be limited thereto. By way of example, the gas may include a gas selected from the group consisting of hydrogen, oxygen, carbon dioxide, carbon monoxide, nitrogen, xenon, argon, neon, air, ozone, krypton, helium, a nitrogen-containing compound gas, a carbon-containing compound gas, and combinations thereof, but may not be limited thereto. The gas supply line unit may further include a gas tank connected to the inlet valve 525, but may not be limited thereto. By way of example, a gas included within the gas tank may be injected into the liquid tank 510 through the supply pipe 520 by opening the inlet valve 525, and the gas injected through the supply pipe 520 may be supplied to the porous pipe body 530, but may not be limited thereto.

By way of example, if the gas stored in the gas tank is included in the liquid, after combustion the gas generates only water but does not generate a pollutant, and also has a high combustion rate, and thus, may be efficiently used, but may not be limited thereto.

Figure 20:
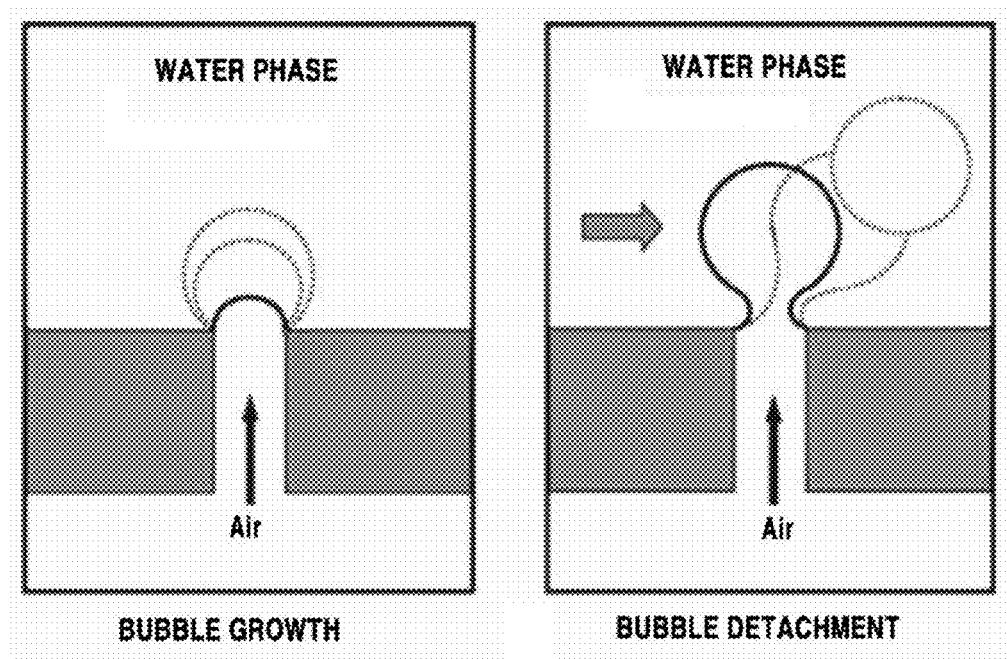
FIG. 20 is a schematic diagram showing generation of microbubbles on a surface of a porous material in accordance with an embodiment of the present disclosure.

In accordance with an embodiment of the present disclosure, the porous pipe body 530 may have holes each having a size of from about 1 nm to about 1 mm, but may not be limited thereto. By way of example, the porous pipe body may have holes each having a size of from about 1 nm to about 1 mm, from about 10 nm to about 1 mm, from about 100 nm to about 1 mm, from about 300 nm to about 1 mm, from about 500 nm to about 1 mm, from about 700 nm to about 1 mm, from about 900 nm to about 1 mm, from about 1 μm to about 1 mm, from about 10 μm to about 1 mm, from about 100 μm to about 1 mm, from about 300 μm to about 1 mm, from about 500 μm to about 1 mm, from about 700 μm to about 1 mm, from about 900 μm to about 1 mm, from about 1 nm to about 900 μm, from about 10 nm to about 900 μm, from about 100 nm to about 900 μm, from about 300 nm to about 900 μm, from about 500 nm to about 900 μm, from about 700 nm to about 900 μm, from about 900 nm to about 900 μm, from about 1 μm to about 900 μm, from about 10 μm to about 900 μm, from about 100 μm to about 900 μm, from about 300 μm to about 900 μm, from about 500 μm to about 900 μm, from about 700 μm to about 900 μm, from about 1 nm to about 700 μm, from about 10 nm to about 700 μm, from about 100 nm to about 700 μm, from about 300 nm to about 700 μm, from about 500 nm to about 700 μm, from about 700 nm to about 700 μm, from about 900 nm to about 700 μm, from about 1 μm to about 700 μm, from about 10 μm to about 700 μm, from about 100 μm to about 700 μm, from about 300 μm to about 700 μm, from about 500 μm to about 700 μm, from about 1 nm to about 500 μm, from about 10 nm to about 500 μm, from about 100 nm to about 500 μm, from about 300 nm to about 500 μm, from about 500 nm to about 500 μm, from about 700 nm to about 500 μm, from about 900 nm to about 500 μm, from about 1 μm to about 500 μm, from about 10 μm to about 500 μm, from about 100 μm to about 500 μm, from about 300 μm to about 500 μm, from about 1 nm to about 300 μm, from about 10 nm to about 300 μm, from about 100 nm to about 300 μm, from about 300 nm to about 300 μm, from about 500 nm to about 300 μm, from about 700 nm to about 300 μm, from about 900 nm to about 300 μm, from about 1 μm to about 300 μm, from about 10 μm to about 300 μm, from about 100 μm to about 300 μm, from about 1 nm to about 100 μm, from about 10 nm to about 100 μm, from about 100 nm to about 100 μm, from about 300 nm to about 100 μm, from about 500 nm to about 100 μm, from about 700 nm to about 100 μm, from about 900 nm to about 100 μm, from about 1 μm to about 100 μm, from about 10 μm to about 100 μm, from about 1 nm to about 10 μm, from about 10 nm to about 10 μm, from about 100 nm to about 10 μm, from about 300 nm to about 10 μm, from about 500 nm to about 10 μm, from about 700 nm to about 10 μm, from about 900 nm to about 10 μm, from about 1 μm to about 10 μm, from about 1 nm to about 1 μm, from about 10 nm to about 1 μm, from about 100 nm to about 1 μm, from about 300 nm to about 1 μm, from about 500 nm to about 1 μm, from about 700 nm to about 1 μm, from about 900 nm to about 1 μm, from about 1 nm to about 900 nm, from about 10 nm to about 900 nm, from about 100 nm to about 900 nm, from about 300 nm to about 900 nm, from about 500 nm to about 900 nm, from about 700 nm to about 900 nm, from about 1 nm to about 700 nm, from about 10 nm to about 700 nm, from about 100 nm to about 700 nm, from about 300 nm to about 700 nm, from about 500 nm to about 700 nm, from about 1 nm to about 500 nm, from about 10 nm to about 500 nm, from about 100 nm to about 500 nm, from about 300 nm to about 500 nm, from about 1 nm to about 300 nm, from about 10 nm to about 300 nm, from about 100 nm to about 300 nm, from about 1 nm to about 100 nm, from about 10 nm to about 100 nm, or from about 1 nm to about 10 nm, but may not be limited thereto. By way of example, as shown in FIG. 20, the porous pipe body may convert the gas into microbubbles while the gas passes through the porous pipe body, but may not be limited thereto. By way of example, if the gas is formed into microbubbles while passing through the holes of the porous pipe body, the micrometer-sized microbubbles may be converted into nanometer-sized nanobubbles due to a self-shrinking effect of the microbubbles, but may not be limited thereto.

OTHER MODE

Hereinafter, the present disclosure will be explained in detail with reference to examples. However, the present disclosure is not limited thereto.

<Example 1> Preparation of Nanobubble Water

In order to produce a cell culture medium in accordance with Example 1, nanobubble water was prepared.

1) Preparation of Hydrogen Nanobubble Water

An apparatus for producing microbubble water using a ultrasonic vibrator illustrated in FIG. 1 was used and a microporous filter was used to inject a gas without applying a ultrasonic wave, so that hydrogen nanobubble water was prepared by a pressure dissolving method.

Figure 4A:
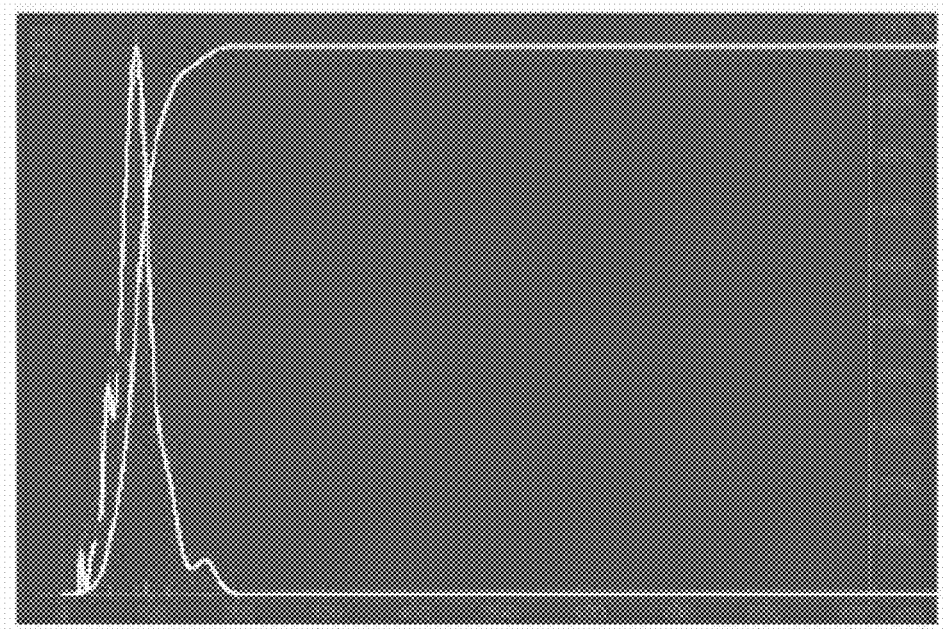
Figure 4A:
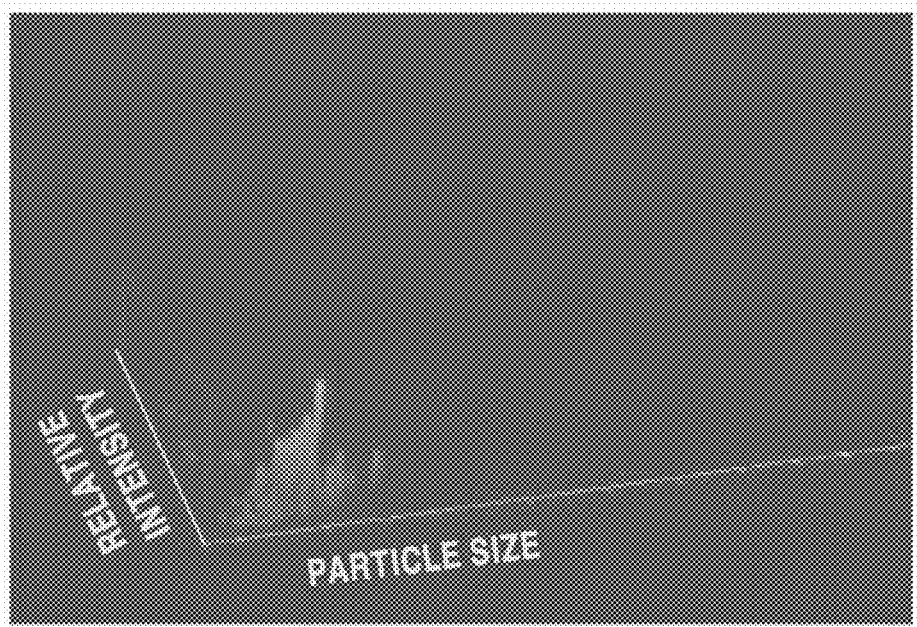

The prepared hydrogen nanobubble water was examined by a nano particle tracking analysis (NTA, LM10-HS-BFT14, UK) method. According to the result thereof, as illustrated in FIG. 4A and FIG. 4B, hydrogen nanobubbles contained in the hydrogen nanobubble water had an average diameter of about 87 nm and a concentration of about $2.12 \times 10^{17}$ per about 1 mL.

2) Preparation of Oxygen Nanobubble Water

An apparatus for producing microbubble water using a ultrasonic vibrator illustrated in FIG. 1 was used and a microporous filter was used to inject a gas without applying a ultrasonic wave, so that oxygen nanobubble water was prepared by a pressure dissolving method.

Figure 5A:
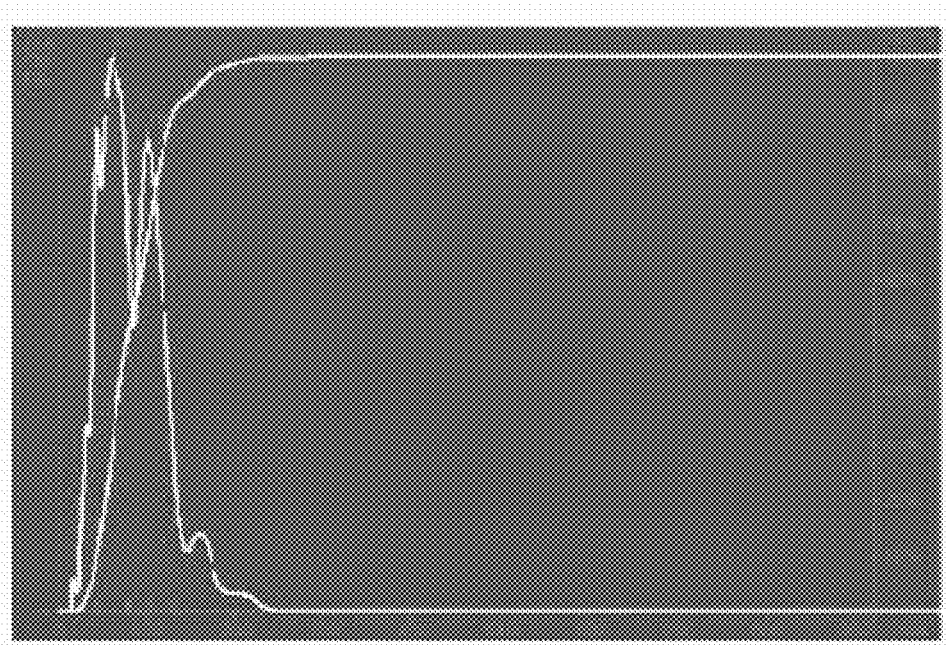
Figure 5A:
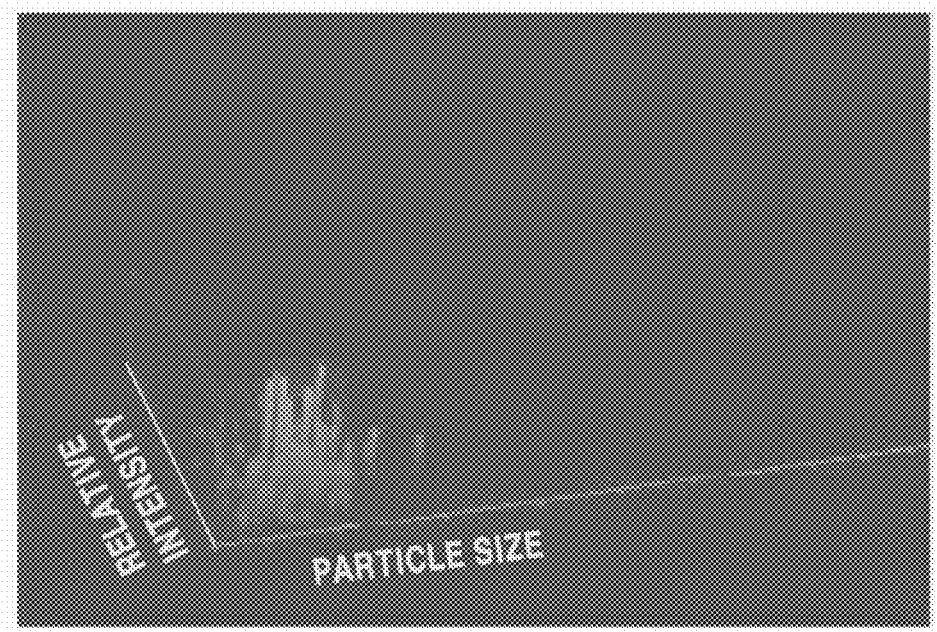
Figure 6:
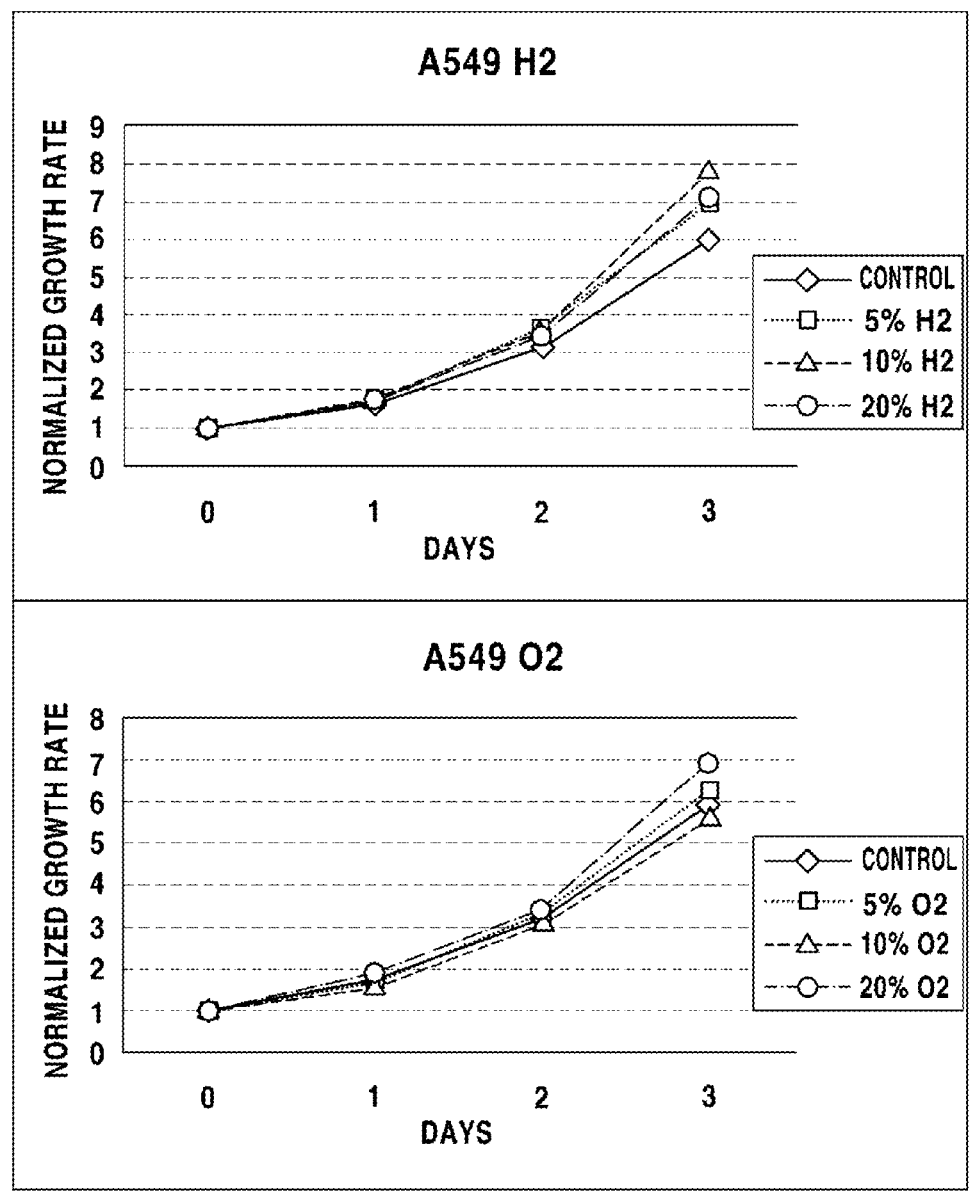
FIG. 6 shows a result of analysis by optical image cell counting on the growth of lung cancer cell A549 cultured for various periods of time in a cell culture medium containing hydrogen microbubble water and oxygen microbubble water in accordance with an example of the present disclosure.
Figure 7:
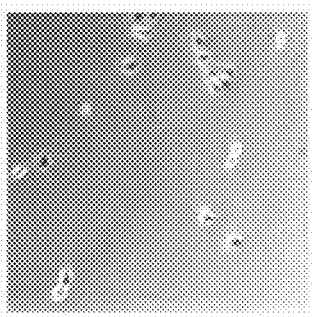
FIG. 7 shows a result of analysis on the cell images of lung cancer cell A549 in accordance with an example of the present disclosure.
Figure 7:
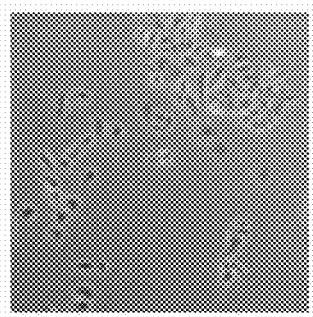
Figure 7:
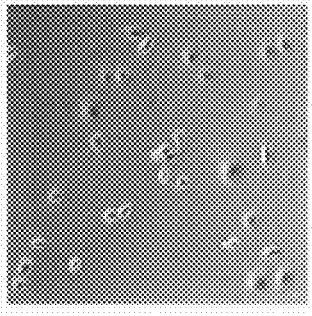
Figure 7:
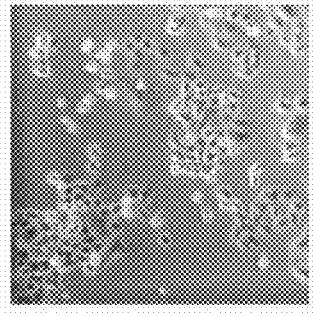
Figure 7:
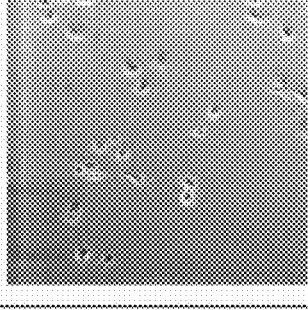
Figure 7:
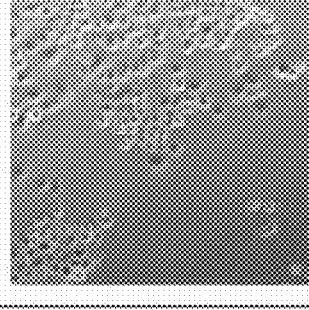
Figure 8:
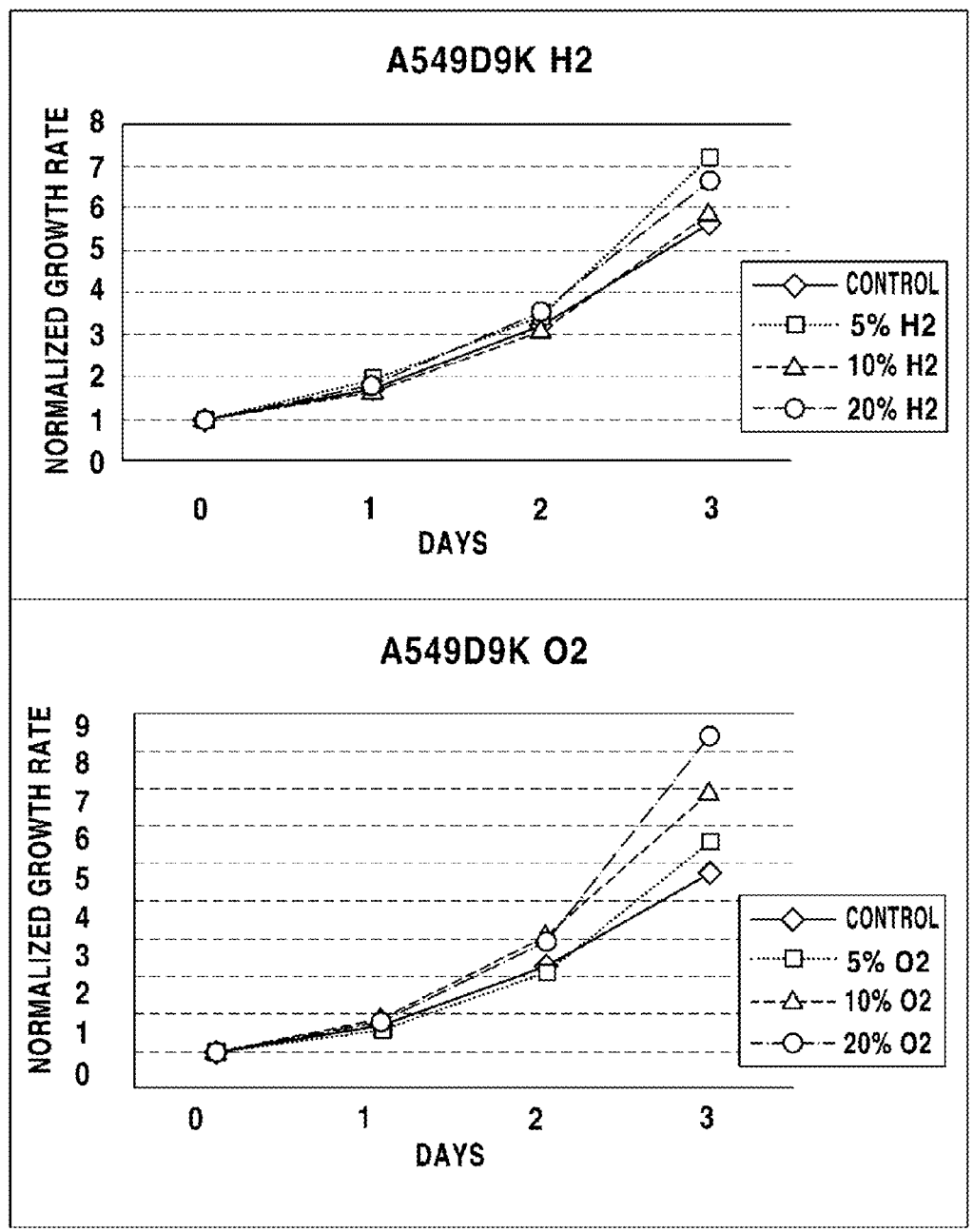
FIG. 8 shows a result of analysis by optical image cell counting on the growth of lung cancer cell A549D9K cultured for various periods of time in a cell culture medium containing hydrogen microbubble water and oxygen microbubble water in accordance with an example of the present disclosure.
Figure 9:
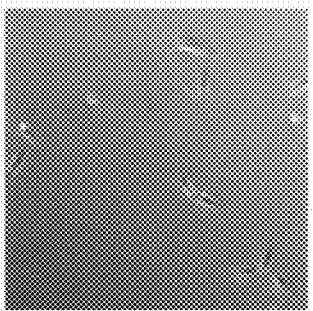
FIG. 9 shows a result of analysis on the cell images of lung cancer cell A549D9K in accordance with an example of the present disclosure.
Figure 9:
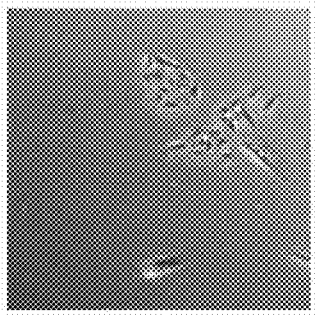
Figure 9:
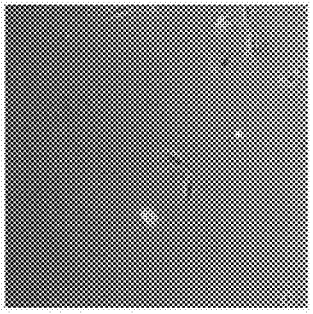
Figure 9:
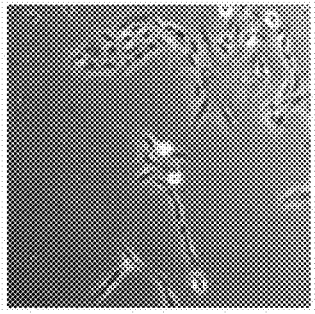
Figure 9:
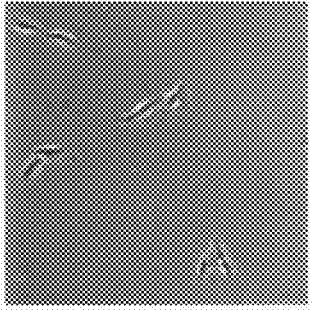
Figure 9:
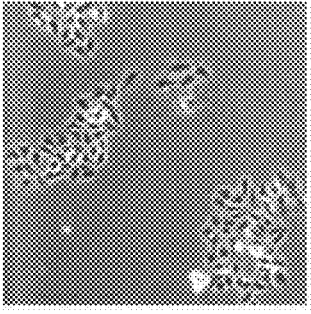
Figure 10:
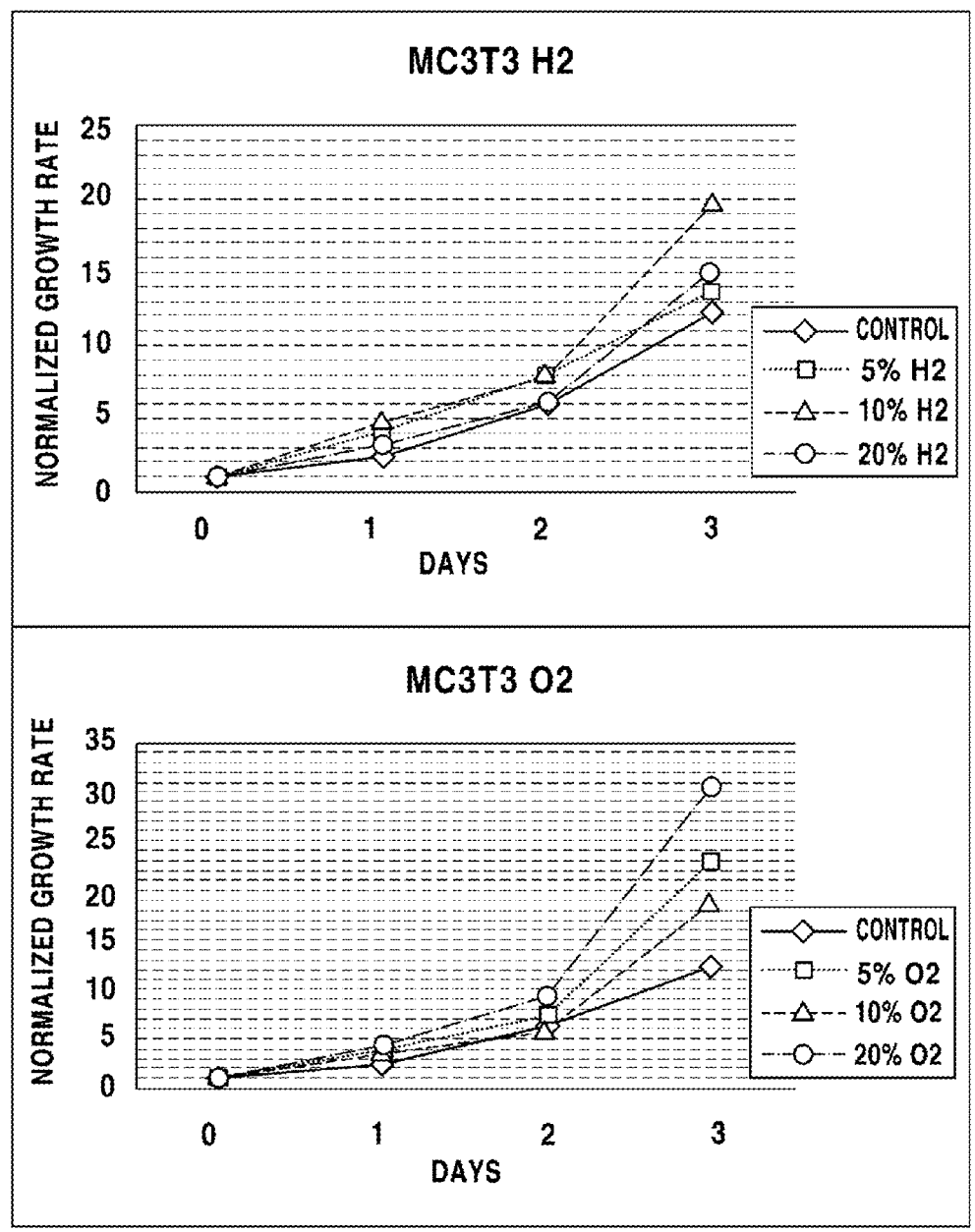
FIG. 10 shows a result of analysis by optical image cell counting on the growth of osteoblast MC3T3 cultured in a cell culture medium containing hydrogen microbubble water and oxygen microbubble water in accordance with an example of the present disclosure.
Figure 11:
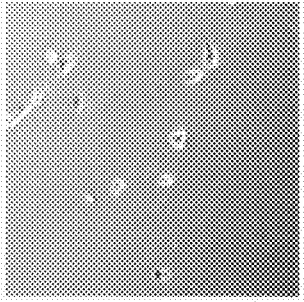
FIG. 11 shows a result of analysis on the cell images of osteoblast MC3T3 in accordance with an example of the present disclosure.
Figure 11:
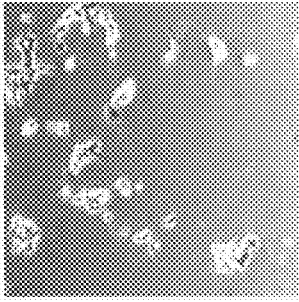
Figure 11:
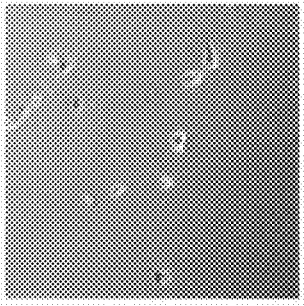
Figure 11:
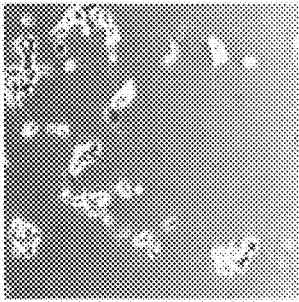
Figure 11:
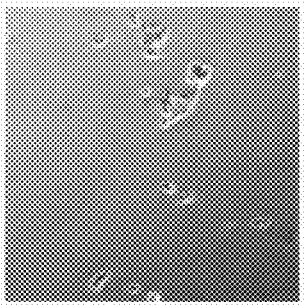
Figure 11:
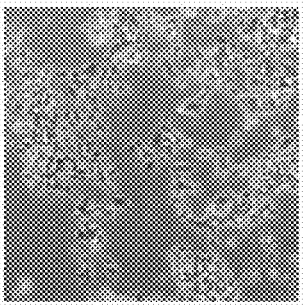
Figure 12:
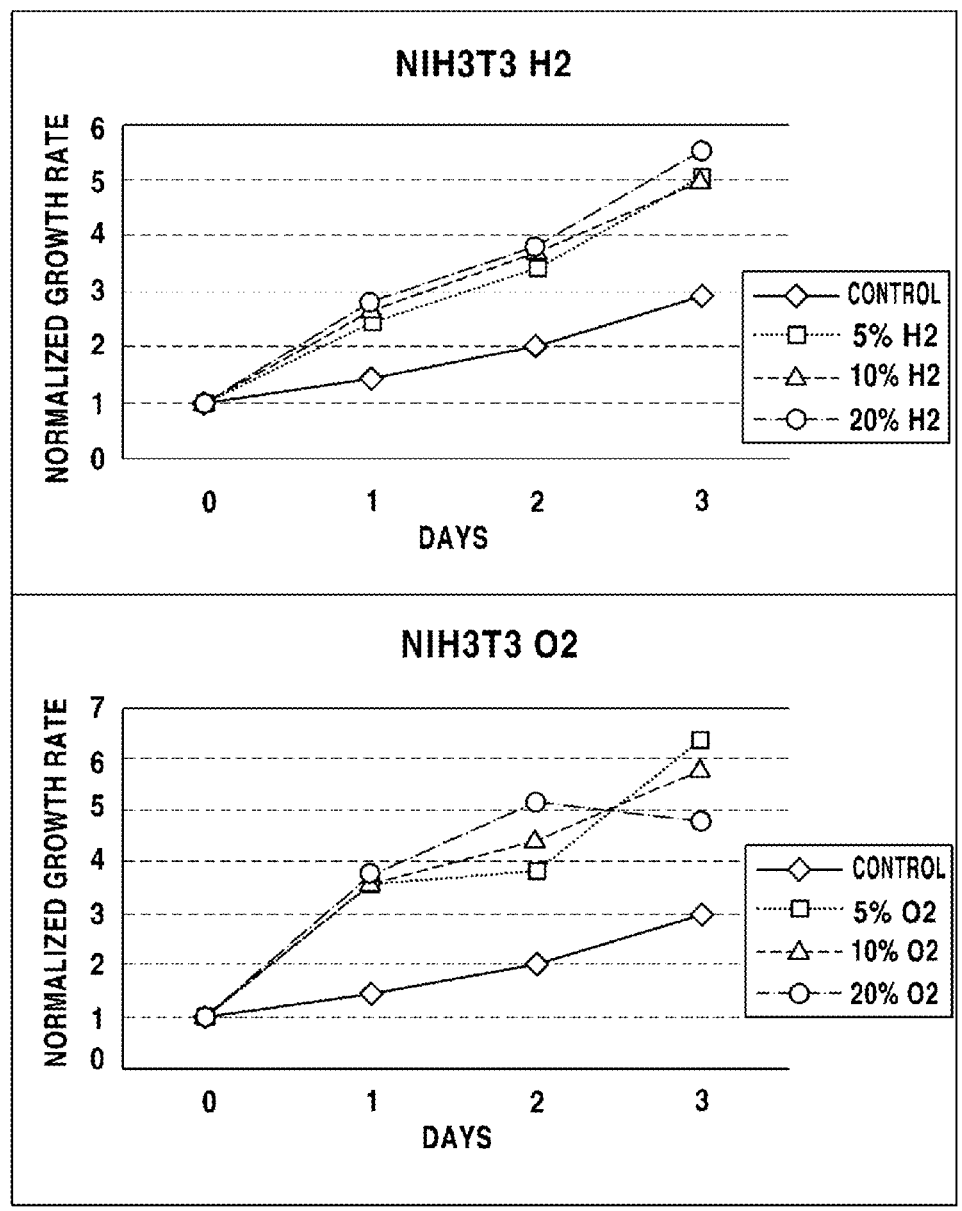
FIG. 12 shows a result of analysis by optical image cell counting on the growth of fibroblast NIH3T3 cultured for various periods of time in a cell culture medium containing hydrogen microbubble water and oxygen microbubble water in accordance with an example of the present disclosure.
Figure 13:
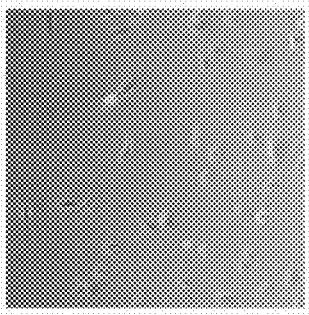
FIG. 13 shows a result of analysis on the cell images of fibroblast NIH3T3 in accordance with an example of the present disclosure.
Figure 13:
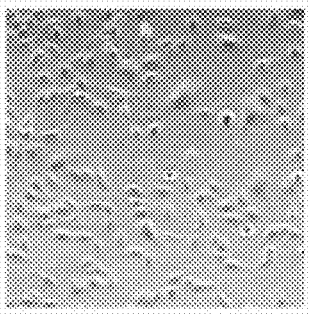
Figure 13:
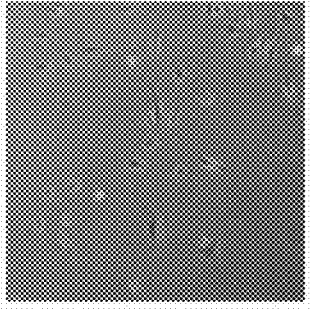
Figure 13:
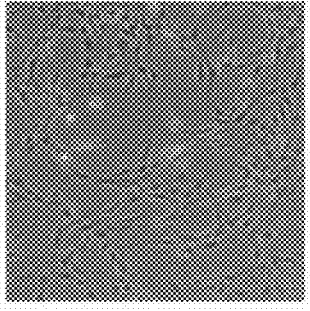
Figure 13:
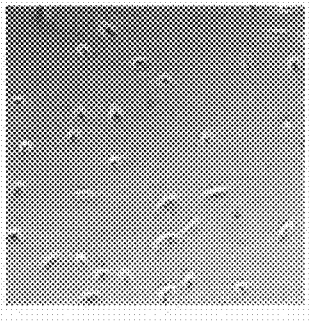
Figure 13:
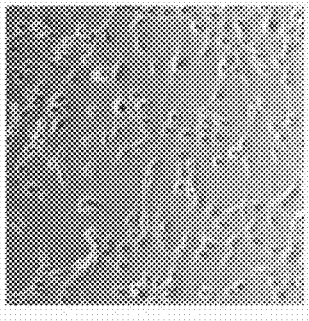
Figure 14:
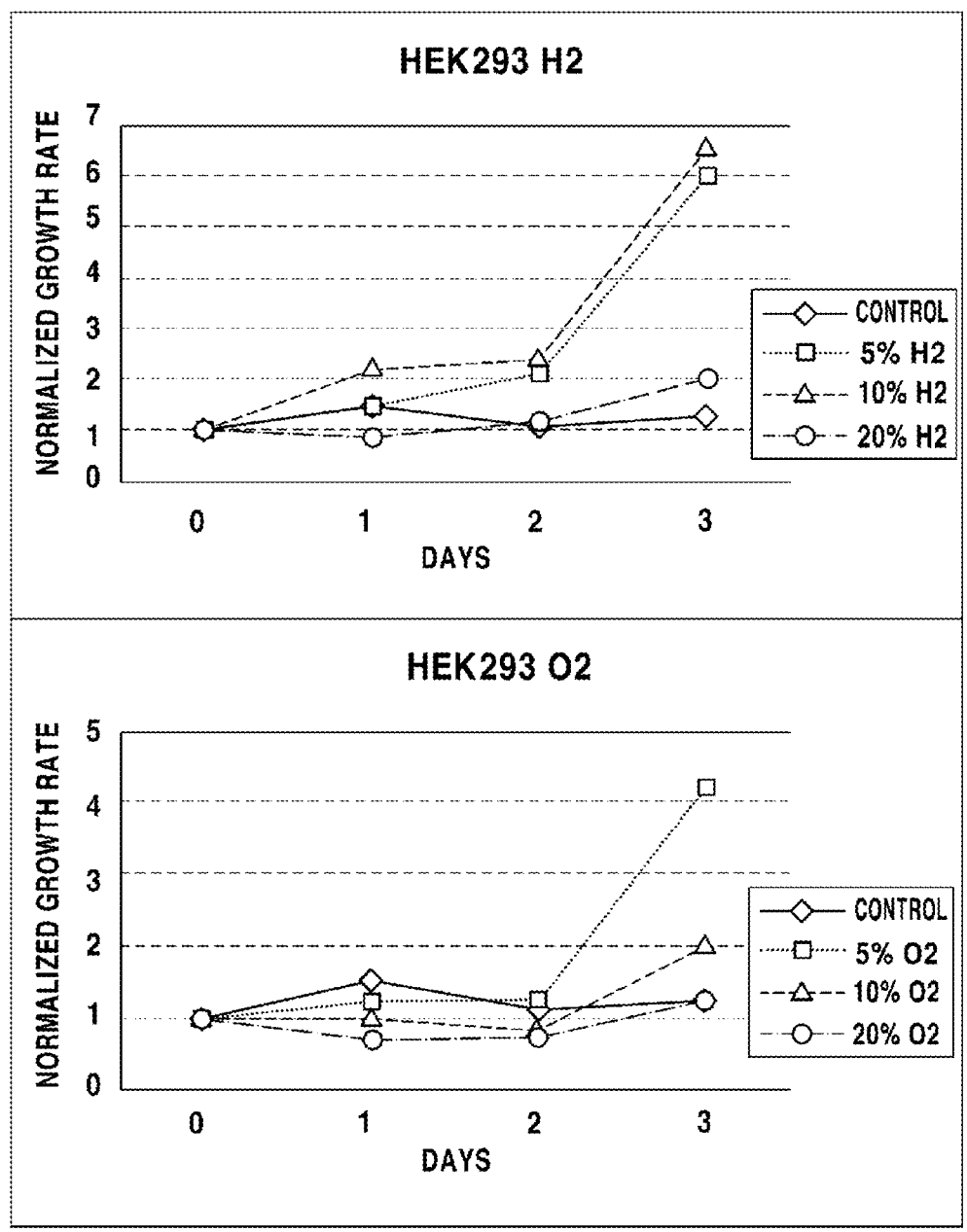
FIG. 14 shows a result of analysis by optical image cell counting on the growth of kidney cell HEK293 cultured for various periods of time in a cell culture medium containing hydrogen microbubble water and oxygen microbubble water in accordance with an example of the present disclosure.
Figure 15:
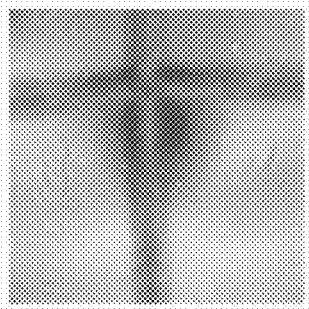
FIG. 15 shows a result of analysis on the cell images of kidney cell HEK293 in accordance with an example of the present disclosure.
Figure 15:
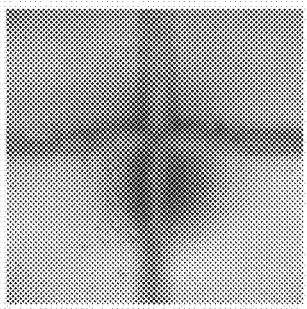
Figure 15:
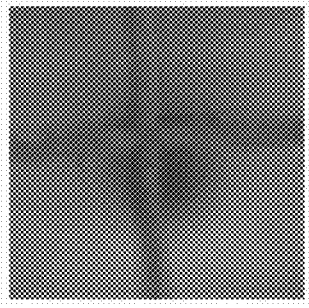
Figure 15:
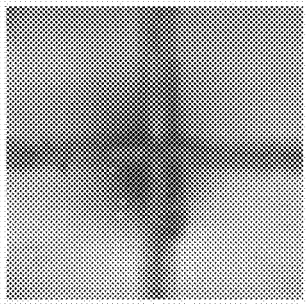
Figure 15:
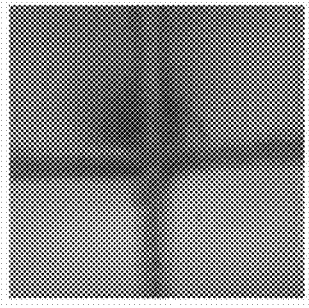
Figure 15:
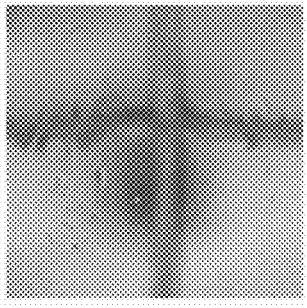

Water analysis of the prepared oxygen nanobubble water was examined by a nano particle tracking analysis (NTA, LM10-HSBFT14, UK) method. According to the result thereof, as illustrated in FIG. 5A and FIG. 5B, oxygen nanobubbles contained in the oxygen nanobubble water had an average diameter of about 87 nm and a concentration of about $2.62 \times 10^{17}$ per about 1 mL.

<Example 2> Cell Culture

In a cell culture method in accordance with Example 2, four kinds of cell lines were divided to respective media and then cultured in a confluent manner in a 5% $CO_2$ incubator at 37° C. In this case, lung cancer cell A549 (purchased from ATCC) contained 10% FetalClone III (Lonza) and 1% penicillin-streptomycin (MP) in DMEM (Cellgro); lung cancer cell A549D9K (D9K mutated CXCR2 expressed in A549) contained 10% FetalClone III (Lonza), 1% penicillin-streptomycin (MP), and 600 μg/mL of G418 (Cellgro) in DMEM (Cellgro); osteoblast MC3T3 (purchased from ATCC) contained 10% fetal bovine serum (FBS, Lonza) and 1% penicillin-streptomycin (MP) in MEM Alpha Modification (HyClone); and fibroblast NIH3T3 (purchased from ATCC) and kidney cell HEK293 (purchased from ATCC) contained 10% fetal bovine serum (FBS, Lonza) and 1% penicillin-streptomycin (MP) in DMEM (Cellgro).

<Example 3> Cell Growth and Survival Analysis

1. Cell Growth Analysis

The cells were separated and subcultured by using trypsin-EDTA (1×, GibcoBRL). In order to check a cell survival rate, the cells were seeded into a 24-well culture plate and a 96-well culture plate at a cell density of about $4 \times 10^4$ cells/mL and optical image cell counting was carried out. In this case, an Image-J (Wayne Rasband) was used for cell counting. One day after cell seeding, the cell media were replaced with media containing nanobubble water of 5 volume %, 10 volume %, and 20 volume %, respectively, and the cells were cultured for various periods of time. In this case, the nanobubble water was sterilized under UV light before being mixed into the media. Meanwhile, a cell including a medium only was used as a negative control.

As a result thereof, as illustrated in FIG. 6, FIG. 8, FIG. 10, FIG. 12, and FIG. 14, it was confirmed that there was an increase in cell growth of lung cancer cells A549, A549D9K, osteoblast MC3T3, fibroblast NIH3T3, and kidney cell HEK293, respectively.

2. Optical Analysis of Growth Rate

An optical measurement system including a phase-contrast microscope (Nikon TiU), a camera (Quantiem: 512SC), and an NIS-element software (Nikon Instruments Inc.) was used. After replacement with the media containing nanobubble water, an image (15×) of each cell in each well was analyzed regularly in time.

The respective images of lung cancer cells A549, A549D9K, osteoblast MC3T3, fibroblast NIH3T3, and kidney cell HEK293 were as shown in FIG. 7, FIG. 9, FIG. 11, FIG. 13, and FIG. 15, and it was confirmed that there was a remarkable increase in cell growth in the case of being treated for 72 hours in the media using nanobubble water as compared with the control group.

<Example 4> Preparation of Hydrogen Nanobubble Gasoline

In order to prepare a high-efficiency mixed fuel in accordance with Example 4, hydrogen nanobubble gasoline was prepared. In order to prepare the hydrogen nanobubble gasoline, a hydrogen gas having a purity of 99.995% (Shinyoung Special Gas) and gasoline having an octane number of from 91 to 94 (Hyundai Oilbank) were used, and an additional purification process was not performed. In order to generate hydrogen nanobubbles in the gasoline, a device for producing microbubbles having the same structure as the producing device according to an embodiment of the present disclosure was used (FIG. 19). The device for producing microbubbles included the liquid tank 510 injected with gasoline and the porous pipe body 530. The hydrogen gas flowing from the hydrogen gas tank through the hydrogen gas supply line unit was injected into the porous pipe body 530. The porous pipe body 530 included a porous material and was provided at a lower part of the liquid tank 510 to be submerged in the gasoline. The hydrogen gas injected into the porous pipe body 530 generated hydrogen nanobubbles on a surface of the porous pipe body 530. The hydrogen nanobubbles generated on the surface of the porous pipe body 530 were applied with a holding force for holding the hydrogen nanobubbles on a solid surface and a detaching force for detaching the hydrogen nanobubbles from the solid surface. As illustrated in FIG. 20, when the hydrogen nanobubbles were grown, the detaching force became greater than the holding force, and thus, the hydrogen nanobubbles could be detached from the surface of the porous pipe body 530. In Example 4, there was prepared gasoline in which hydrogen nanobubbles were generated at normal temperature and normal pressure. An amount of gasoline evaporated due to its high volatility during the process for generating hydrogen nanobubbles was charged. Finally, after the device for producing microbubbles was stopped, the gasoline in which the hydrogen nanobubbles were generated in the liquid tank 510 was obtained through an outlet valve 540, and the obtained gasoline in which the hydrogen nanobubbles were generated was kept in a general plastic bottle at normal temperature and normal pressure.

As an engine used for an experiment, an EF Sonata manufactured by Hyundai Motors and using an electronically controlled in-line 4-cylinder engine with a displacement of about 2,000 cc was used.

TABLE 1

| Test Item | | Unit | Gasoline | Hydrogen Nanobubble Gasoline | Test Method |
|---|---|---|---|---|---|
| Density (15° C.) | | kg/m$^3$ | 738.2 | 772 | KS M ISO 12185:2003 |
| True Calorific Value | | J/g | 43 230 | 43 310 | KS M 2057:2006 |
| Total Calorific Value | | J/g | 46 430 | 46 300 | KS M 2057:2006 |
| Water (K-F Coulometric Titration Method) | | mg/kg | 73 | 81 | KS M ISO 12937:2003 |
| Sulfur content (UV fluorescence spectrometry) | | mg/kg | 6 | 17 | KS M 2027:2010 |
| Hydrocarbon Component Analysis | Total Aromatic Compound Content | Volume % | 15.5 | 32.5 | JIS K 2536-2:2003 |
| | Benzene Content | Volume % | 0.13 | 0.01 | |
| | Hydrogen (H) Content | Volume % | 14.16 | 13.23 | |

As shown in Table 1, the gasoline (Hyundai Oilbank) as commercialized and sold in Korea and the gasoline including hydrogen nanobubbles were used in Example 4. An effect of the hydrogen nanobubbles on a calorific value of gasoline was checked by measuring calorific values of the respective gasolines. According to a result of the present experiment, it was confirmed that even when hydrogen nanobubbles were generated in conventional gasoline, there was no big difference in calorific value.

TABLE 2

| Viscosity (MPa · s) | 1 | 2 | 3 | 4 | 5 | Average |
|---|---|---|---|---|---|---|
| Gasoline | 0.58 | 0.58 | 0.58 | 0.6 | 0.58 | 0.58 |
| Hydrogen Nanobubble Gasoline | 0.54 | 0.54 | 0.54 | 0.56 | 0.56 | 0.55 |

Table 2 shows the viscosities of the conventional gasoline and the gasoline including hydrogen nanobubbles. As shown in Table 2, an average viscosity of the conventional gasoline was about 0.58 MPa·s and an average viscosity of the gasoline including hydrogen nanobubbles was about 0.55 MPa·s, and thus, it could be seen that the viscosity of the gasoline including hydrogen nanobubbles was lower by about 0.03 MPa·s. In order to measure the viscosities of the gasoline, a LVT viscometer (Brookfield Engineering Laboratories INC., U.S.A.) was used. The viscometer used for measurement included a main body including an indicator needle, a spindle, a support, and a circular inclinometer, and was configured to measure a viscosity of from about 1.0 MPa·s to about 2.0×10$^6$ MPa·s at a spindle rate of from about 0.3 rpm to about 60 rpm. After the indicator needle was stabilized at a predetermined spindle rate, a result was obtained. Finally, when a value indicated by the indicator needle was determined, a dynamic viscosity was calculated by using a conversion factor. The viscosity of the gasoline refers to an internal resistance generated when the gasoline flows. When the viscosity of the gasoline is high, an injection characteristic deteriorates, and thus, it is necessary to increase an injection pressure when the fuel is injected, and also, engine performance and a combustion characteristic may deteriorate.

TABLE 3

| Surface Tension (dyn/cm) | 1 | 2 | 3 | 4 | 5 | Average |
|---|---|---|---|---|---|---|
| Gasoline | 13.5 | 13.6 | 13.6 | 13.5 | 13.5 | 13.5 |
| Hydrogen Nanobubble Gasoline | 14 | 14 | 13.9 | 13.9 | 13.9 | 13.9 |

Table 3 shows the surface tensions of the conventional gasoline and the gasoline including hydrogen nanobubbles. The surface tensions of the gasoline was measured by using a Du Nouy tension meter (No. 3179, Itoh Seisakusho, Japan) using a Du Nouy ring method that measured to surface tension of the liquid. As shown in Table 3, an average surface tension of the conventional gasoline was about 13.54 dyn/cm and an average surface tension of the gasoline including hydrogen nanobubbles was about 13.93 dyn/cm, and thus, it could be seen that the surface tension of the gasoline including hydrogen nanobubbles was higher than about 0.39 dyn/cm.

TABLE 4

| Type | Right After Generation | After 76 Days | After 121 Days |
|---|---|---|---|
| Concentration (×10$^8$ particles/mL) | 11.35 | 10.51 | 10.6 |

Referring to Table 4, an average value of hydrogen nanobubbles in the gasoline including the hydrogen nanobubbles according to time and a change in number of hydrogen nanobubbles with time could be seen. In order to measure the number of hydrogen nanobubbles, a nano particle tracking analysis (NTA) system was used. The system is configured to irradiate a laser beam to record a video of hydrogen nanobubbles moved according to Brawnian motion in a liquid. The laser irradiation system was placed under the lens of a microscope, and a hydrogen nanobubble within a liquid specimen passing through a laser beam path was expressed by the system as a small white dot being moved or vibrated. When a video was recorded, the NTA 2.3 analytic software tracked each hydrogen nanobubble and measured a diffusion coefficient D$_t$ of the hydrogen nanobubble. As a result, the number of hydrogen nanobubbles was determined by the measured diffusion coefficient with a radius (r) of the hydrogen nanobubble and a Stokes-Einstein equation as shown below.

$$D_t = (K_B \cdot T)/(6 \cdot \pi \cdot \eta \cdot r)$$

Herein, $K_B$ is the Boltzmann constant, T is a temperature, and η is a viscosity of a liquid.

According to the concentration of the gasoline including hydrogen nanobubbles as calculated by the above-described method, there was no big change in number of hydrogen nanobubbles even after time passed, which means the stability of hydrogen nanobubbles in gasoline.

Figure 21A:
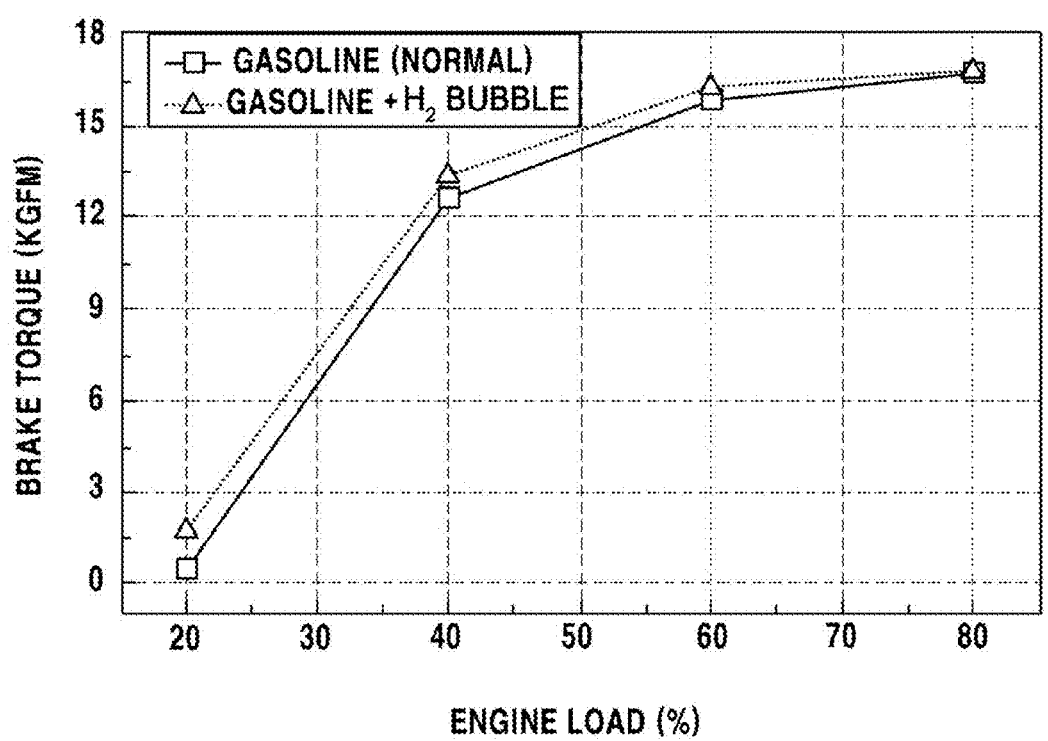
FIG. 21A to FIG. 21C show the power characteristics of the conventional gasoline and the gasoline in which microbubbles are generated in accordance with an example of the present disclosure.
Figure 21B:
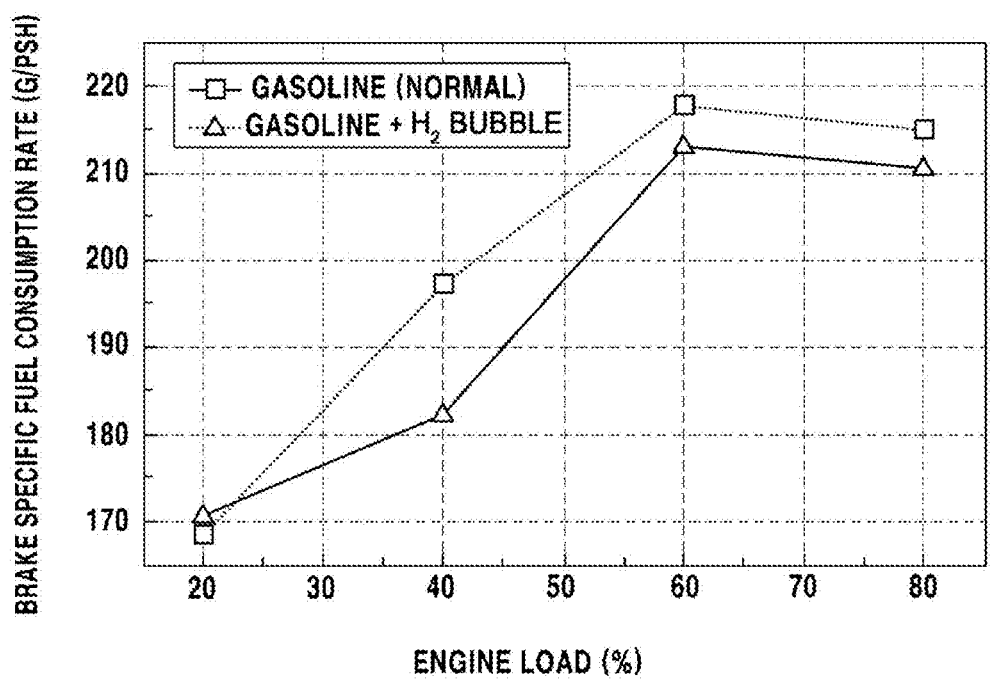
Figure 21C:
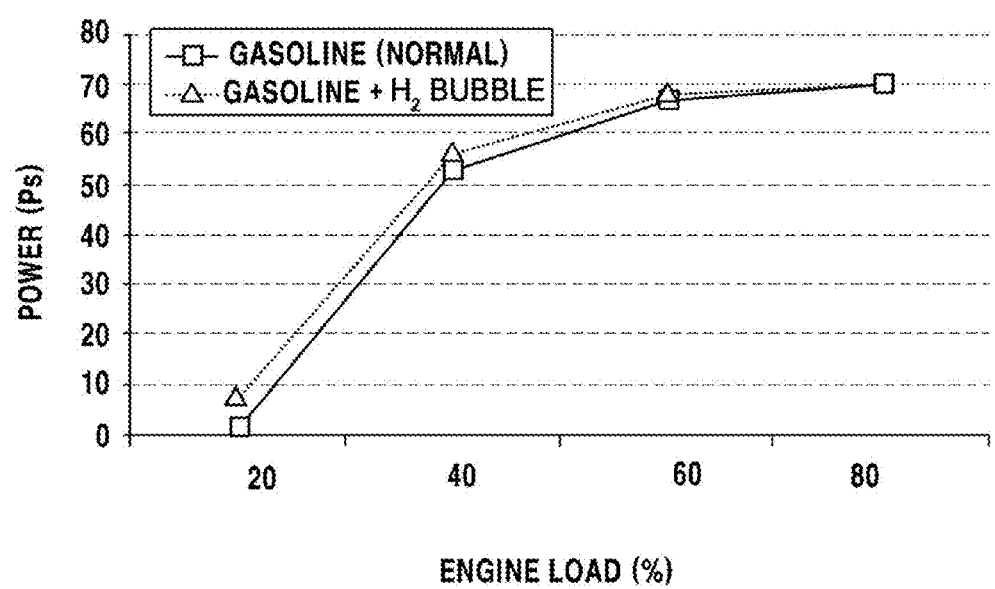

FIG. 21A to FIG. 21C are graphs showing the power characteristics of the conventional gasoline and the gasoline in which microbubbles are generated in accordance with Example 4. FIG. 21A to FIG. 21C show variations in torque value, fuel consumption rate, and power value measured while a variation of an accelerator was increased in a state where an engine speed was fixed at about 3,000 rpm. FIG. 21A shows brake torque values depending on an engine load in accordance with Example 4, FIG. 21B shows brake specific fuel consumption rates depending on an engine load in accordance with Example 4, and FIG. 21C shows power values depending on an engine load in accordance with Example 4. As shown in FIG. 21A, the torque (output) value is a representative value with which an output characteristic can be evaluated. It could be seen that the gasoline including hydrogen nanobubbles was increased in torque value at a low load and an intermediate load, as compared with the conventional gasoline. Particularly, according to the fuel consumption rates characteristic as shown in FIG. 21B, the gasoline including hydrogen nanobubbles had an improved output value while consuming a smaller amount of fuel. It was assumed that a high explosion pressure property of the hydrogen component contained in the gasoline including hydrogen nanobubbles had an influence on combustion performance and thus a higher combustion pressure was generated. As shown in FIG. 21C, the gasoline including hydrogen nanobubbles in accordance with Example 4 had an improved power while consuming a smaller amount of fuel, as compared with the conventional gasoline.

Figure 22A:
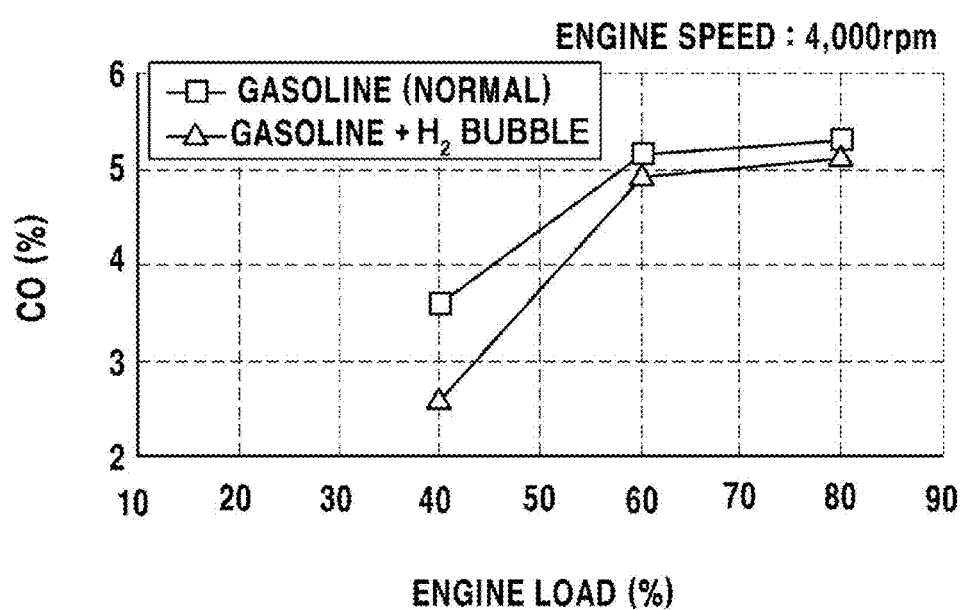
FIG. 22A to FIG. 22D show the generation rates of harmful exhaust emissions depending on an engine load of the conventional gasoline and the gasoline in which microbubbles are generated in accordance with an example of the present disclosure.
Figure 22B:
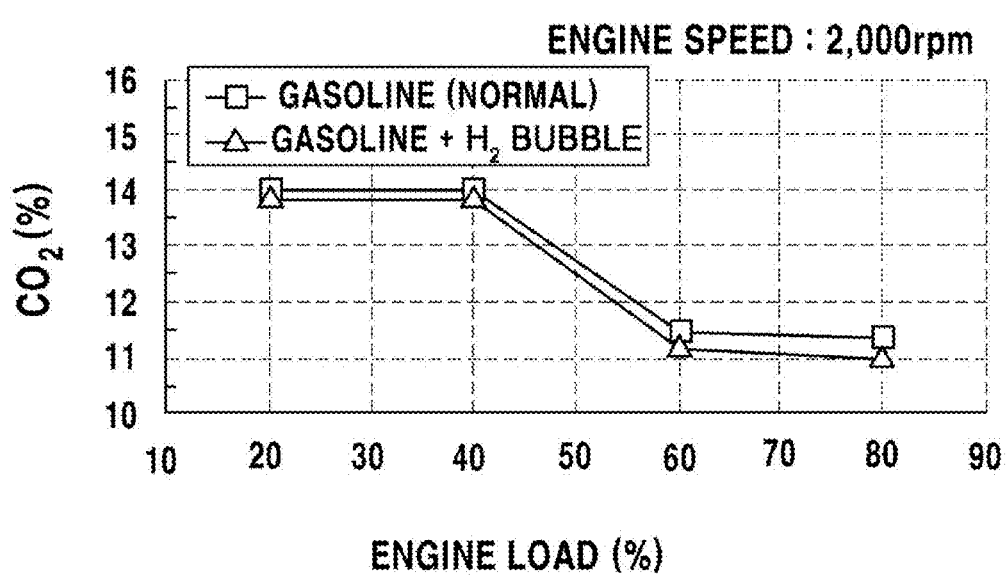
Figure 22C:
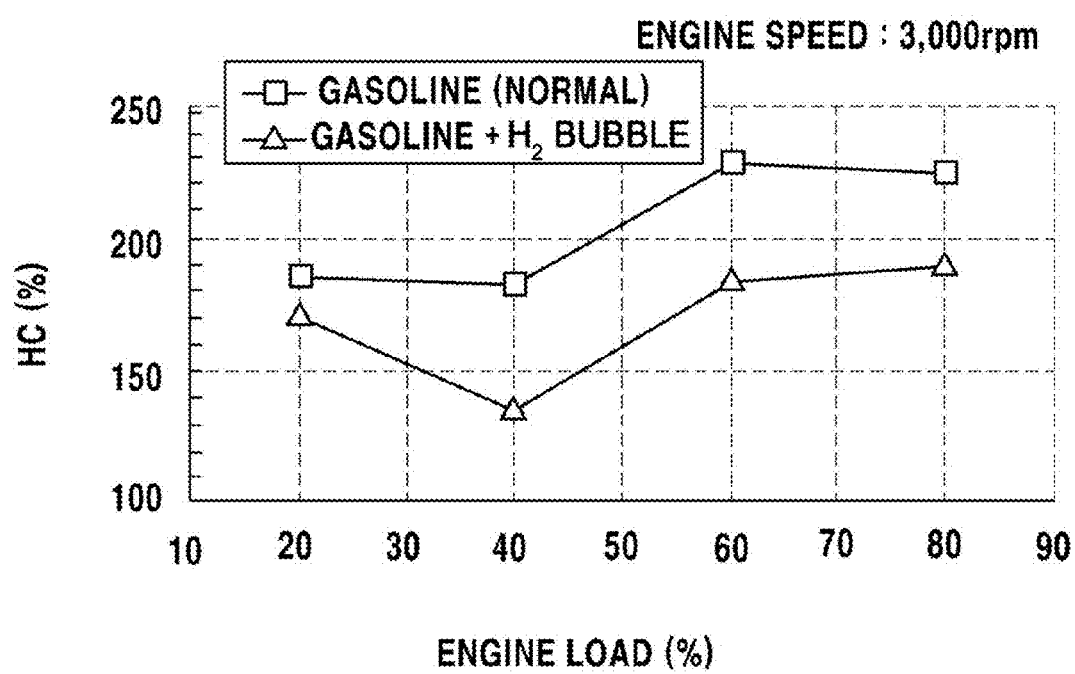
Figure 22D:
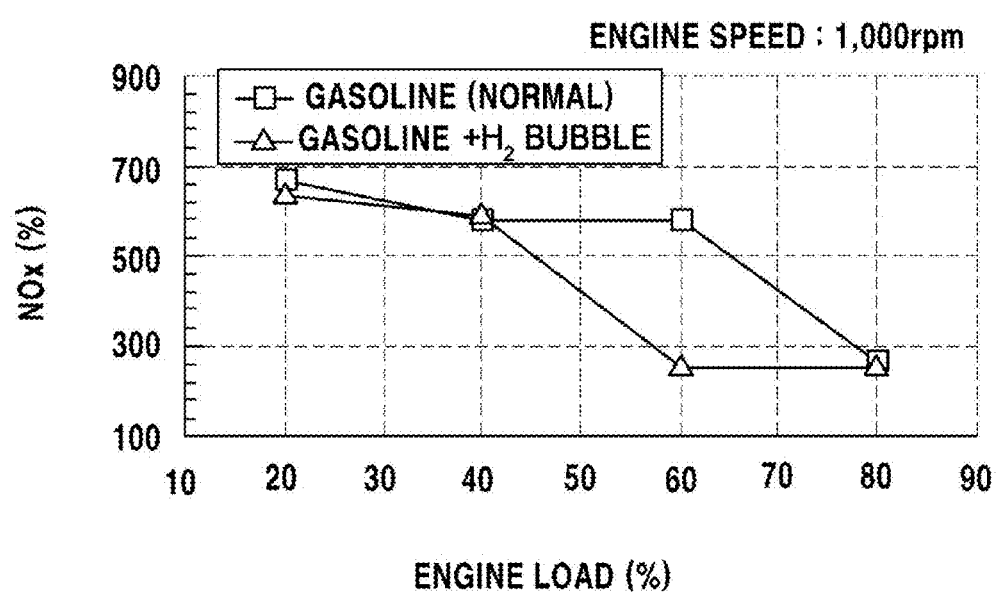

FIG. 22A to FIG. 22D show the characteristics of harmful exhaust emissions depending on an engine load of conventional gasoline and the gasoline in which microbubbles are generated in accordance with Example 4, and show the generation rates of carbon monoxide, carbon dioxide, hydrocarbon, and a nitrogen compound. The harmful exhaust emissions have been known as major greenhouse gases and gases related to respiratory diseases. The harmful exhaust emissions are closely related with combustion performance. It could be seen that as for carbon monoxide and carbon dioxide shown in FIG. 22A and FIG. 22B, the gasoline including hydrogen nanobubbles had lower generation rates than the general gasoline in the entire range of engine load. Further, it could be seen that as for hydrocarbon shown in FIG. 22C, the gasoline including hydrogen nanobubbles had a remarkably lower generation rate than the conventional gasoline in the entire range of engine load. Hydrocarbon is generated according to a principle in which carbon and hydrogen as major components of fuel are not combusted but discharged during a combustion process. As can be seen from FIG. 22C, it was assumed that the gasoline including hydrogen nanobubbles was more combusted perfectly than gasoline and thus an amount of hydrocarbon was reduced. As for a nitrogen compound as shown in FIG. 22D, it could be seen that the generation rates of the compound was reduced in the entire range of engine load. A nitrogen oxide is directly related to a combustion temperature, and thus, when a combustion pressure is increased, a combustion temperature is increased, resulting in an increase in the nitrogen oxide. That is, as a flame temperature is increased, an amount of the nitrogen oxide is also increased. As can be seen from the above-described output characteristic, it was assumed that a flame temperature was high within a combustion chamber due to a high output, and thus, an amount of the nitrogen oxide was increased. However, in the engine used for the present experiment, an exhaust aftertreatment device was removed. Generally, since the nitrogen oxide can be easily reduced by a three-way catalytic aftertreatment purifier, it was assumed that it is possible to decrease sufficiently by using an aftertreatment device or adjusting a time for ignition or an air-fuel ratio (amount of injected fuel).

That is, if an optimum air-fuel ratio of a mixed fuel including gasoline and hydrogen nanobubbles is found and a time for ignition and an amount of injected fuel are precisely adjusted, it is possible to obtain a high output, a high fuel consumption rate, and less generation of harmful exhaust emissions.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

100: Liquid tank; 101: Discharge port; 102: Inlet port; 200: Liquid circulation line unit; 210: Circulation pipe; 220: Circulation motor; 300: Gas supply line unit; 310: Gas bomb; 320: Supply pipe; 330: Pressure control valve; 340: Distribution pipe; 400: Microbubble discharge unit; 410: Porous pipe body; 420: Body unit; 421: Main body pipe; 422: Elastic fixing ring; 423: Connection pipe body; 424: Curved coupling groove; 425: Gas inlet hole; 426: Ultrasonic vibrator; 430: Vibration transfer unit; 440: Front closing cap; 441: Coupling nut unit; 450: Rear closing cap; 451: Bolt unit; 452: Gas through-hole; 453: Curved recess groove; 510: Liquid tank; 520: Supply pipe; 525: Inlet valve; 530: Porous pipe body; 540: Outlet valve

We claim:
1. A high-efficiency mixed fuel comprising:
a fuel; and
hydrogen nanobubbles formed in the fuel,
wherein 1 mL of the fuel includes from $10^3$ to $10^{18}$ hydrogen nanobubbles, and
wherein the hydrogen nanobubbles are generated by passing hydrogen gas through a porous pipe body in the fuel, the porous pipe body including multiple holes each having a respective diameter of from 1 nm to 900 nm, and the hydrogen nanobubbles having an average diameter of from 1 nm to 900 nm.

2. The high-efficiency mixed fuel of claim 1, wherein the fuel includes a member selected from the group consisting of fossil fuels, bio fuels, and combinations thereof.

3. The high-efficiency mixed fuel of claim 1, wherein the high-efficiency mixed fuel has a viscosity of from 0.4 MPa·s to 0.7 MPa·s.

4. The high-efficiency mixed fuel of claim 1, wherein the high-efficiency mixed fuel has a surface tension of from 12 dyn/cm to 15 dyn/cm.

* * * * *